United States Patent
Otomo et al.

(10) Patent No.: US 12,319,673 B2
(45) Date of Patent: Jun. 3, 2025

(54) ELECTRO-OPTIC POLYMER

(71) Applicant: NATIONAL INSTITUTE OF INFORMATION AND COMMUNICATIONS TECHNOLOGY, Tokyo (JP)

(72) Inventors: Akira Otomo, Tokyo (JP); Isao Aoki, Tokyo (JP); Toshiki Yamada, Tokyo (JP); Chiyumi Yamada, Tokyo (JP)

(73) Assignee: NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 1250 days.

(21) Appl. No.: 16/965,745

(22) PCT Filed: Jan. 30, 2019

(86) PCT No.: PCT/JP2019/003148
§ 371 (c)(1),
(2) Date: Jul. 29, 2020

(87) PCT Pub. No.: WO2019/151318
PCT Pub. Date: Aug. 8, 2019

(65) Prior Publication Data
US 2021/0032228 A1    Feb. 4, 2021

(30) Foreign Application Priority Data
Jan. 30, 2018   (JP) .................. 2018-013469

(51) Int. Cl.
*C07D 409/06*    (2006.01)
*C08F 220/14*    (2006.01)
(Continued)

(52) U.S. Cl.
CPC .......... *C07D 409/06* (2013.01); *C08F 220/14* (2013.01); *C08F 220/36* (2013.01);
(Continued)

(58) Field of Classification Search
CPC ..... C07D 409/06; G02F 1/061; G02F 1/3614; G02F 2202/022; C08F 220/14; C08F 220/36
See application file for complete search history.

(56) References Cited

U.S. PATENT DOCUMENTS

| 6,067,186 A | 5/2000 | Dalton et al. |
| 6,348,992 B1 | 2/2002 | Zhang et al. |

(Continued)

FOREIGN PATENT DOCUMENTS

| CN | 107216320 | 9/2017 |
| JP | 2004-501159 | 1/2004 |

(Continued)

OTHER PUBLICATIONS

Mingqian He, Thomas M. Leslie, and John A. Sinicropi, Synthesis of Chromophores with Extremely High Electro-optic Activity. 1. Thiophene-Bridge-Based Chromophores, Chem. Mater. 2002, 14, 4662-4668. (Year: 2002).*

(Continued)

*Primary Examiner* — Bijan Ahvazi
(74) *Attorney, Agent, or Firm* — WENDEROTH, LIND & PONACK, L.L.P.

(57) ABSTRACT

The present invention provides an electro-optic polymer (EO polymer) comprising an electro-optic molecule (EO molecule) and a base polymer. The EO polymer of the present invention has good performance over the entire optical communication wavelength range and therefore can preferably be used for the production of optical modulators, optical switches, optical transceivers, optical phased arrays, (Continued)

LiDAR (light detection and ranging) devices, electric field sensors, terahertz wave generators and detectors, etc.

15 Claims, 6 Drawing Sheets

(51) Int. Cl.
    *C08F 220/36*   (2006.01)
    *G02F 1/061*   (2006.01)
    *G02F 1/361*   (2006.01)

(52) U.S. Cl.
    CPC ............ *G02F 1/061* (2013.01); *G02F 1/3614* (2013.01); *G02F 2202/022* (2013.01)

(56) References Cited

U.S. PATENT DOCUMENTS

| | | | |
|---|---|---|---|
| 6,361,717 | B1 | 3/2002 | Dalton et al. |
| 6,393,190 | B1 | 5/2002 | He et al. |
| 6,555,027 | B2 | 4/2003 | Wang et al. |
| 6,584,266 | B1 | 6/2003 | He et al. |
| 6,616,865 | B1 | 9/2003 | Zhang et al. |
| 6,652,779 | B1 | 11/2003 | Zhang et al. |
| 7,144,679 | B2 | 12/2006 | Izumida et al. |
| 8,846,955 | B2 | 9/2014 | Otomo et al. |
| 9,488,755 | B2 | 11/2016 | Otomo et al. |
| 9,977,150 | B2 | 5/2018 | Otomo et al. |
| 10,253,124 | B2 | 4/2019 | Otomo et al. |
| 11,661,428 | B1 * | 5/2023 | Ashton ................ G02F 1/3611 252/582 |
| 2003/0096065 | A1 | 5/2003 | Berneth et al. |
| 2007/0267606 | A1 | 11/2007 | Huang |
| 2009/0268999 | A1 | 10/2009 | Huang |
| 2012/0172599 | A1 * | 7/2012 | Otomo ................ G02F 1/0063 549/60 |
| 2017/0088654 | A1 * | 3/2017 | Otomo ................ G02F 1/3617 |
| 2018/0224577 | A1 | 8/2018 | Otomo et al. |
| 2019/0225728 | A1 | 7/2019 | Otomo et al. |

FOREIGN PATENT DOCUMENTS

| | | |
|---|---|---|
| JP | 2005-504170 | 2/2005 |
| JP | 2012-042899 | 3/2012 |
| JP | 5376359 | 12/2013 |
| JP | 5945905 | 6/2016 |
| JP | 6137694 | 5/2017 |
| WO | 2018/003842 | 1/2018 |

OTHER PUBLICATIONS

Feng Qiu, Hiromu Sato, Andrew M. Spring, 1 Daisuke Maeda, Masa-aki Ozawa, Keisuke Odoi, Isao Aoki, Akira Otomo, and Shiyoshi Yokoyama, Ultra-thin silicon/electro-optic polymer hybrid waveguide modulators, Applied Physics Letters 107, 123302 (2015). (Year: 2015).*
Toshiki Yamada, Takahiro Kaji, Isao Aoki, Chiyumi Yamada, Maya Mizuno, Shingo Saito, Yukihiro Tominari, Shukichi Tanaka, and Akira Otomo,Terahertz time domain and far-infrared spectroscopies of side-chain electro-optic polymers, Japanese Journal of Applied Physics 55, 03DC11 (2016). (Year: 2016).*
Mingqian He et al., "Synthesis of Chromophores with Extremely High Electro-optic Activities. 2. Isophorone- and Combined Isophorone-Thiophene-Based Chromophores", pp. 4669-4675, vol. 14, No. 11, Chemistry of Materials, 2002.
International Search Report (ISR) issued Apr. 23, 2019 in International (PCT) Application No. PCT/JP2019/003148.
Mingqian He, et al., "Synthesis of Chromophores with Extremely High Electro-optic Activity. 1. Thiophene-Bridge-Based Chromophores", Chemistry of Materials, vol. 14, No. 11, pp. 4662-4668, 2002, cited in both the specification & CA.

* cited by examiner

ELECTRO-OPTIC POLYMER

TECHNICAL FIELD

The present invention relates to a polymer that is useful as an electro-optic polymer.

BACKGROUND ART

Electro-optic (EO) materials are used in optical control elements (optical elements) of various optical devices, such as optical modulators, optical switches, optical interconnect modules, optoelectronic circuits, wavelength converters, electric field sensors, terahertz (THz) wave generators and detectors, optical phased arrays, etc. The most commonly used EO materials for such applications are inorganic ferroelectric materials. However, inorganic ferroelectric materials have limitations in speed performance, further miniaturization and higher integration. In order to realize next-generation ultra-high-speed optical communications, there is a need to explore new materials that offer high-speed performance and are compatible for hybrid integration with silicon photonic structures.

Organic electro-optic polymers (organic EO polymers) are promising materials that would play a vital role in next-generation optical communications because they have higher electro-optic effect as compared with inorganic ferroelectric materials, offer high-speed performance, and enable further miniaturization and higher integration because of their compatibility with hybrid integration with silicon photonic structures. Until now, EO molecules have been developed to meet the applications in the C-band (wavelength of 1530 nm to 1565 nm), which is used for long-distance optical communications, and EO molecules having a high EO coefficient in the C-band have been intensively explored.

The basic structure of EO molecules is composed of a donor, a π-conjugation bridge, and an acceptor. A known approach for increasing the EO coefficient of EO molecules is using a strong electron acceptor and a strong electron donor and extending a π-conjugation bridge. Various EO molecules having such a structure are already known (for example, see Patent Literature 1 to 4 and Non Patent Literature 1).

Patent Literature 5 reports that EO polymers having an EO molecule bound to a polymer composed of a specific ratio of specific monomers have long-term stable EO effect.

CITATION LIST

Patent Literature

Patent Literature 1: U.S. Pat. No. 6,067,186A
Patent Literature 2: JP-W 2004-501159
Patent Literature 3: Japanese Patent No. 5376359
Patent Literature 4: Japanese Patent No. 5945905
Patent Literature 5: Japanese Patent No. 6137694

Non Patent Literature

Non Patent Literature 1: Chem. Mater. 2002, 14, 4662-4668

SUMMARY OF INVENTION

Technical Problem

In recent years, there is a demand for increasing the speed of short- and medium-distance optical interconnects, and novel EO polymers have been desired to be developed. In short- and medium-distance optical interconnects, the O-band (wavelength of 1260 nm to 1360 nm) is usually used, and EO polymers using an EO molecule designed for the C-band are unsuitable due to their absorption coefficient being too high in the O-band. To solve the problem, there is a need for EO polymers that have a low absorption coefficient and use an EO molecule having a sufficiently high EO coefficient.

In optical communication systems, wavelength division multiplexing (WDM) communication is used for increased transmission capacity. WDM is a technology of transmitting multiple signals of different wavelengths in a specific wavelength range, such as the C-band and the O-band, along a single fiber. Optical modulators for optical communication systems are intended for use in the entire specific wavelength range used for WDM and have to be designed to work across different wavelength bands.

The present invention relates to a novel electro-optic (EO) polymer. In particular, the present invention relates to an EO polymer that is useful in a desired optical communication wavelength range including the O-band.

Solution to Problem

Conventional EO molecules having a high EO coefficient are characterized in that, as the EO coefficient increases, the absorption spectrum shifts to long wavelengths. The absorption spectrum is usually measured using a thin-film sample of a few hundred nanometers in thickness. In the measured spectrum, the absorption peaks at around 800 nm and decreases to almost zero at wavelengths of 1100 nm or more. Based on this premise, conventional EO molecules have been considered not to cause the problem of absorption in the communication wavelength range including the C-band and the O-band.

In the device application of EO materials, waveguides have to be configured to allow light to propagate a distance of a few centimeters. To this end, the absorption coefficient should be about 3 dB/cm or less (preferably 1 dB/cm or less). However, the optical density (OD) of a 1-μm-thick thin-film of an EO material having an absorption coefficient of 3 dB/cm is about 0.00003, which is a level below the limit of measurement even with a high-performance spectrophotometer, so that proper evaluation cannot be made. This problem might be overcome by increasing the film thickness, but thick-film production of an EO polymeric material is difficult, and the film thickness can be increased to at most a few hundred micrometers even by a special method. Even if a film of 200-μm thickness can be obtained, the OD is still as low as 0.006, which is lower than the reflection loss of 0.035, so that accurate evaluation is difficult. For this reason, precise comparison of EO materials with regard to the absorption coefficient has never been made, and the high level of the EO coefficient has been highlighted so far.

In the present study, the present inventors evaluated conventional EO polymeric materials with regard to the absorption coefficient. As a result, the absorption coefficient of EO polymeric materials having a high EO coefficient, which are designed for the C-band, was about 3 dB/cm and an adequate level in the C-band, but was as high as 20 dB/cm or more and an unsatisfactory level in the O-band. On the other hand, the EO coefficient of EO polymers having an absorption coefficient of 3 dB/cm or less in the O-band was as low as less than 30 pm/V and an unsatisfactory level.

To address this problem, the present inventors conducted intensive research focused on both the absorption coefficient and the EO coefficient of EO polymers. As a result, the present inventors found that EO polymers suitable for use in a desired optical communication wavelength range are characterized in that the EO coefficient and the figure of merit (FOM), as defined by a specific equation using the absorption coefficient, both of which are calculated for the desired optical communication wavelength range, meet their respective thresholds. Based on this finding, the present inventors completed the present invention.

That is, the present invention relates to the following [1] to [20].

[1] An electro-optic polymer (EO polymer) comprising an electro-optic molecule (EO molecule) and a base polymer, the EO molecule having a structure in which a π-electron donor and a π-electron acceptor are conjugated via a π-conjugation bridge, the EO polymer having an electro-optic coefficient (EO coefficient) of 30 pm/V or more and a figure of merit (FOM) of $10 \times 10^{-6}$ cm/dBV or more in an entire optical communication wavelength range of 1260 nm to 1625 nm, the FOM being defined by the following formula:

$$FOM = \frac{n^3 r}{a_{max} \lambda} [10^{-6} \text{ cm/dBV}] \quad [\text{Math. 1}]$$

wherein n indicates a refractive index, r indicates an EO coefficient, $a_{max}$ indicates a maximum absorption coefficient in a wavelength range of interest, and λ indicates a wavelength.

[2] The EO polymer according to the above [1], wherein the EO polymer has an EO coefficient of 35 pm/V or more and an FOM of $13 \times 10^{-6}$ cm/dBV or more in O-band ranging in wavelength from 1260 nm to 1360 nm.

[3] The EO polymer according to the above [1], wherein the EO polymer has an EO coefficient of 32 pm/V or more and an FOM of $11 \times 10^{-6}$ cm/dBV or more in OE-band ranging in wavelength from 1260 nm to 1460 nm.

[4] The EO polymer according to the above [1], wherein the EO polymer has an EO coefficient of 32 pm/V or more and an FOM of $20 \times 10^{-6}$ cm/dBV or more in E-band ranging in wavelength from 1360 nm to 1460 nm.

[5] The EO polymer according to the above [1], wherein the EO polymer has an EO coefficient of 32 pm/V or more and an FOM of $25 \times 10^{-6}$ cm/dBV or more in S-band ranging in wavelength from 1460 nm to 1530 nm.

[6] The EO polymer according to the above [1], wherein the EO polymer has an EO coefficient of 31 pm/V or more and an FOM of $30 \times 10^{-6}$ cm/dBV or more in C-band ranging in wavelength from 1530 nm to 1565 nm.

[7] The EO polymer according to the above [1], wherein the EO polymer has an EO coefficient of 30 pm/V or more and an FOM of $20 \times 10^{-6}$ cm/dBV or more in SCL-band ranging in wavelength from 1460 nm to 1625 nm.

[8] The EO polymer according to any one of the above [1] to [7], wherein the EO molecule is a compound represented by the following formula (1):

[Chem. 1]

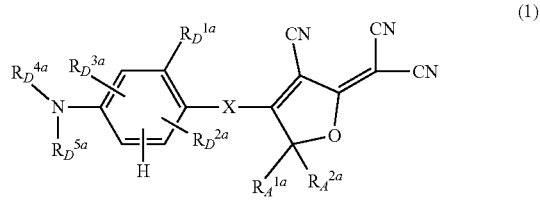

(1)

wherein $R_D^{1a}$, $R_D^{2a}$, and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, $-R^1-OH$ (wherein $R^1$ is a hydrocarbon group), $-OR^2-OH$ (wherein $R^2$ is a hydrocarbon group), $-OC(=O)R^3$ (wherein $R^3$ is a hydrocarbon group), an amino group, $-R^4-NH_2$ (wherein $R^4$ is a hydrocarbon group), a thiol group, $-R^5-SH$ (wherein $R^5$ is a hydrocarbon group), $-NCO$, or $-R^6-NCO$ (wherein $R^6$ is a hydrocarbon group), and $R_D^{1a}$, $R_D^{2a}$, and $R_D^{3a}$ each may have one or more identical or different substituents;

$R_D^{4a}$ and $R_D^{5a}$ independently represent a hydrogen atom, an alkyl group, a haloalkyl group, an acyloxyalkyl group, a silyloxyalkyl group, $-R^1-OH$ (wherein $R^1$ is a hydrocarbon group), $-R^4-NH_2$ (wherein $R^4$ is a hydrocarbon group), an aryl group, $-R^5-SH$ (wherein $R^5$ is a hydrocarbon group), or $-R^6-NCO$ (wherein $R^6$ is a hydrocarbon group), and $R_D^{4a}$ and $R_D^{5a}$ each may have one or more identical or different substituents;

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, an aryl group, a hydroxy group, $-R^1-OH$ (wherein $R^1$ is a hydrocarbon group), $-OR^2-OH$ (wherein $R^2$ is a hydrocarbon group), an amino group, $-R^4-NH_2$ (wherein $R^4$ is a hydrocarbon group), a thiol group, $-R^5-SH$ (wherein $R^5$ is a hydrocarbon group), $-NCO$, or $-R^6-NCO$ (wherein $R^6$ is a hydrocarbon group), and $R_A^{1a}$ and $R_A^{2a}$ each may have one or more identical or different substituents.

[9] The EO polymer according to the above [8], wherein at least one of $R_A^{1a}$ and $R_A^{2a}$ is a substituent selected from the group consisting of an aryl group having a halogen atom, an aryl group having a haloalkyl group, and an aryl group having an aryl group optionally having a halogen atom.

[10] The EO polymer according to the above [9], wherein the number of the halogen atom is 1 to 5.

[11] The EO polymer according to the above [9] or [10], wherein the halogen atom is one or more kinds selected from the group consisting of fluorine, chlorine, and bromine.

[12] The EO polymer according to any one of the above [8] to [11], wherein X in formula (1) is represented by the following formula (B-I):

[Chem. 2]

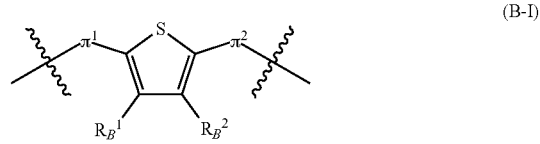

(B-I)

wherein
π¹ and π², which may be the same or different, independently represent a carbon-carbon conjugated π-bond, and π¹ and π² each may have one or more identical or different substituents; and $R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, —R¹—OH (wherein R¹ is a hydrocarbon group), —OR²—OH (wherein R² is a hydrocarbon group), an amino group, —R⁴—NH₂ (wherein R⁴ is a hydrocarbon group), a thiol group, —R⁵—SH (wherein R⁵ is a hydrocarbon group), —NCO, or —R⁶—NCO (wherein R⁶ is a hydrocarbon group), $R_B^1$ and $R_B^2$ each may have one or more identical or different substituents, and $R_B^1$ and $R_B^2$ may form a ring together with the two carbon atoms to which they are bound.

[13] The EO polymer according to any one of the above [8] to [12], wherein the EO molecule is bound to the base polymer via $R_D^{4a}$ and/or $R_D^{5a}$ in formula (1).

[14] A compound represented by the following formula (1):

[Chem. 3]

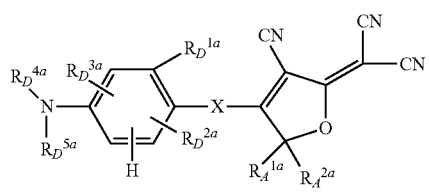

(1)

wherein
$R_D^{1a}$, $R_D^{2a}$, and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, —R¹—OH (wherein R¹ is a hydrocarbon group), —OR²—OH (wherein R² is a hydrocarbon group), —OC(=O)R³ (wherein R³ is a hydrocarbon group), an amino group, —R⁴—NH₂ (wherein R⁴ is a hydrocarbon group), a thiol group, —R⁵—SH (wherein R⁵ is a hydrocarbon group), —NCO, or —R⁶—NCO (wherein R⁶ is a hydrocarbon group), and $R_D^{1a}$, $R_D^{2a}$, and $R_D^{3a}$ each may have one or more identical or different substituents;

$R_D^{4a}$ and $R_D^{5a}$ independently represent a hydrogen atom, an alkyl group, a haloalkyl group, an acyloxyalkyl group, a silyloxyalkyl group, —R¹—OH (wherein R¹ is a hydrocarbon group), —R⁴—NH₂ (wherein R⁴ is a hydrocarbon group), an aryl group, —R⁵—SH (wherein R⁵ is a hydrocarbon group), or —R⁶—NCO (wherein R⁶ is a hydrocarbon group), and $R_D^{4a}$ and $R_D^{5a}$ each may have one or more identical or different substituents;

X is represented by the following formula (B-I):

[Chem. 4]

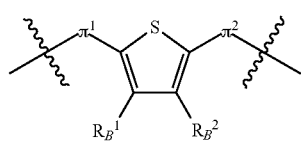

(B-I)

{wherein
π¹ and π², which may be the same or different, independently represent a carbon-carbon conjugated π-bond, and π¹ and π² each may have one or more identical or different substituents; and $R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, —R¹—OH (wherein R¹ is a hydrocarbon group), —OR²—OH (wherein R² is a hydrocarbon group), an amino group, —R⁴—NH₂ (wherein R⁴ is a hydrocarbon group), a thiol group, —R⁵—SH (wherein R⁵ is a hydrocarbon group), —NCO, or —R⁶—NCO (wherein R⁶ is a hydrocarbon group), $R_B^1$ and $R_B^2$ each may have one or more identical or different substituents, and $R_B^1$ and $R_B^2$ may form a ring together with the two carbon atoms to which they are bound}; and $R_A^{1a}$ and $R_A^{2a}$ independently represent an alkyl group, a haloalkyl group, a haloaryl group, or an aryl group having a haloalkyl group.

[15] A figure of merit (FOM) improving material for EO polymers, the FOM improving material comprising a compound represented by the following formula (1):

[Chem. 5]

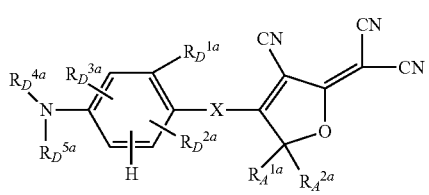

(1)

wherein
$R_D^{1a}$, $R_D^{2a}$, and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, —R¹—OH (wherein R¹ is a hydrocarbon group), —OR²—OH (wherein R² is a hydrocarbon group), —OC(=O) R³ (wherein R³ is a hydrocarbon group), an amino group, —R⁴—NH₂ (wherein R⁴ is a hydrocarbon group), a thiol group, —R⁵—SH (wherein R⁵ is a hydrocarbon group), —NCO, or —R⁶—NCO (wherein R⁶ is a hydrocarbon group), and $R_D^{1a}$, $R_D^{2a}$, and $R_D^{3a}$ each may have one or more identical or different substituents;

$R_D^{4a}$ and $R_D^{5a}$ independently represent a hydrogen atom, an alkyl group, a haloalkyl group, an acyloxyalkyl group, a silyloxyalkyl group, —R¹—OH (wherein R¹ is a hydrocarbon group), —$R^4$—$NH_2$ (wherein $R^4$ is a hydrocarbon group), an aryl group, —$R^5$—SH (wherein $R^5$ is a hydrocarbon group), or —$R^6$—NCO (wherein $R^6$ is a hydrocarbon group), and $R_D^{4a}$ and $R_D^{5a}$ each may have one or more identical or different substituents;

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, an aryl group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), and $R_A^{1a}$ and $R_A^{2a}$ each may have one or more identical or different substituents.

[16] The EO polymer according to any one of the above [1] to [13], wherein the EO polymer is for use in an optical control device.

[17] The EO polymer according to the above [16], wherein the optical control device is an optical modulator, an optical switch, an optical transceiver, an optical phased array, a LiDAR (light detection and ranging) device, an electric field sensor, or a terahertz wave generator and detector.

[18] The EO polymer, the compound, or the FOM improving material according to any one of the above [8] to [17], wherein a combination of $R_A^{1a}$ and $R_A^{2a}$ is such that $R_A^1$ is an alkyl group and $R_A^2$ is an aryl group having a halogen atom, an aryl group having a haloalkyl group, an aryl group having a cycloalkyl group, or an aryl group having an aryl group optionally having a halogen atom.

[19] An optical element formed from the EO polymer according to any one of the above [1] to [13], [16], [17], and [18].

[20] An optical control device comprising the optical element according to the above [19].

Advantageous Effects of Invention

The EO polymer of the present invention is advantageous in that it can be used for applications over the entire optical communication wavelength range, is an optimal EO material for waveguide devices of optical modulators etc., and contributes to enabling ultra-high-speed and low-power data communications.

In addition, the EO polymer of the present invention enables higher integration of optical control devices, which makes it possible to produce ultra-high-speed optical phased arrays. Based on such ultra-high-speed optical phased arrays, miniaturized, high-speed, and high-definition laser radars can be produced, thus enabling completely automatic operation of cars and robots.

Moreover, the EO polymer of the present invention, which is a second-order non-linear optical material, has the advantage of enabling the production of small and highly efficient terahertz wave generators and detectors adapted for external environments.

Furthermore, the EO polymer of the present invention is useful in digital coherent communication systems, which require cascaded modulators for polarization division multiplexing, because the EO polymer has a higher FOM as compared with conventional EO polymers.

DESCRIPTION OF EMBODIMENTS

Figure 1:
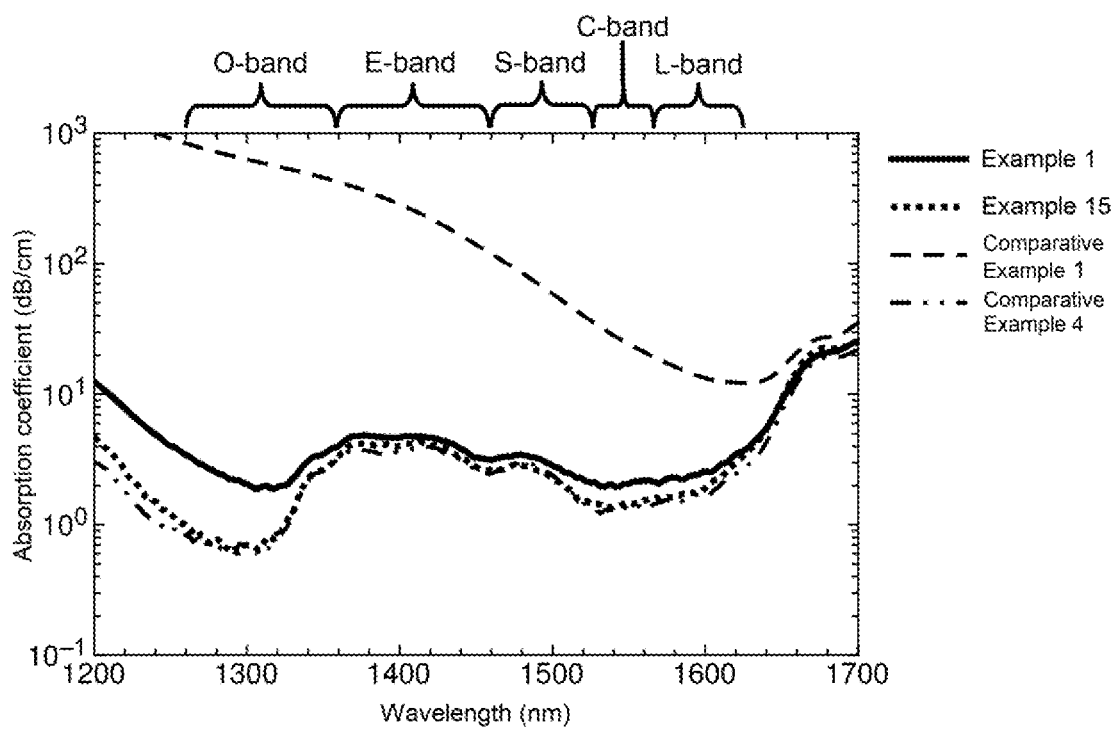
FIG. 1 shows a plot of the measured absorption coefficient versus wavelength in the entire wavelength range for optical communications.

The electro-optic polymer (EO polymer) of the present invention comprises an electro-optic molecule (EO molecule) and a base polymer, and the EO molecule has a structure in which a π-electron donor and a π-electron acceptor are conjugated via a π-conjugation bridge. The EO polymer is also characterized in that the electro-optic coefficient (EO coefficient) and the figure of merit (FOM), as defined by the formula given below, in a desired optical communication wavelength range meet their respective thresholds. The thresholds of the EO coefficient and FOM herein are defined as the minimum values in the wavelength range of interest.

$$FOM = \frac{n^3 r}{a_{max}\lambda}[10^{-6}\ cm/dBV] \qquad \text{[Math. 2]}$$

(In the formula, n indicates a refractive index, r indicates an EO coefficient, $a_{max}$ indicates a maximum absorption coefficient in a wavelength range of interest, and λ indicates a wavelength.)

Conventional EO polymers are difficult to use across different wavelength bands in the entire optical communication wavelength range. For example, certain kinds of EO molecules have a high EO coefficient, but have an absorption coefficient of as high as 3 dB/cm or more in the O-band, ranging in wavelength from 1260 nm to 1360 nm. Other kinds of EO polymers have an absorption coefficient of less than 3 dB/cm in the O-band, but have an EO coefficient of as low as less than 30 pm/V. In contrast, the EO polymer of the present invention is characterized in that the EO coefficient and the FOM, as calculated by the formula given above, in a desired wavelength range meet their respective specific requirements, and the EO polymer can be used for applications over the desired optical communication wavelength range. In general, the phase shift in EO phase modulators is proportional to the device length, but the actual device length is determined based on the propagation loss (absorption loss+scattering loss) acceptable for users. In the present invention, in order to evaluate the FOM of the EO polymer regardless of material, the aforementioned formula for calculating the FOM is used. For example, in order that optical modulators used for WDM work over the entire wavelength range used for WDM, the device length is determined based on the maximum absorption coefficient in the wavelength range of interest, which is designated as $a_{max}$, and accordingly, the FOM calculation uses $a_{max}$.

The EO polymer of the present invention can be defined by the FOM calculated as above and the EO coefficient. More specifically, in the case where the EO polymer of the present invention is intended for use over the entire optical communication wavelength range of 1260 nm to 1625 nm, the EO polymer has an electro-optic coefficient (EO coefficient) of 30 pm/V or more, preferably 35 pm/V or more, and an FOM of $10 \times 10^{-6}$ cm/dBV or more, preferably $15 \times 10^{-6}$ cm/dBV or more.

In a preferable embodiment of the EO polymer of the present invention, the EO coefficient in the O-band, ranging in wavelength from 1260 nm to 1360 nm, is for example 35 pm/V or more, preferably 40 pm/V or more, and the FOM in the O-band is for example $13 \times 10^{-6}$ cm/dBV or more, preferably $15 \times 10^{-6}$ cm/dBV or more.

In another preferable embodiment of the EO polymer of the present invention, the EO coefficient in the OE-band, ranging in wavelength from 1260 nm to 1460 nm, is for example 32 pm/V or more, preferably 40 pm/V or more, and the FOM in the OE-band is for example $11 \times 10^{-6}$ cm/dBV or more, preferably $20 \times 10^{-6}$ cm/dBV or more.

In yet another preferable embodiment of the EO polymer of the present invention, the EO coefficient in the E-band, ranging in wavelength from 1360 nm to 1460 nm, is for example 32 pm/V or more, preferably 40 pm/V or more, and the FOM in the E-band is for example $20 \times 10^{-6}$ cm/dBV or more, preferably $25 \times 10^{-6}$ cm/dBV or more.

In yet another preferable embodiment of the EO polymer of the present invention, the EO coefficient in the S-band, ranging in wavelength from 1460 nm to 1530 nm, is for example 32 pm/V or more, preferably 40 pm/V or more, and the FOM in the S-band is for example $25 \times 10^{-6}$ cm/dBV or more, preferably $30 \times 10^{-6}$ cm/dBV or more.

In yet another preferable embodiment of the EO polymer of the present invention, the EO coefficient in the C-band, ranging in wavelength from 1530 nm to 1565 nm, is for example 31 pm/V or more, preferably 35 pm/V or more, and the FOM in the C-band is for example $30 \times 10^{-6}$ cm/dBV or more, preferably $35 \times 10^{-6}$ cm/dBV or more.

In yet another preferable embodiment of the EO polymer of the present invention, the EO coefficient in the SCL-band, ranging in wavelength from 1460 nm to 1625 nm, is for example 30 pm/V or more, preferably 35 pm/V or more, and the FOM in the SCL-band is for example $20 \times 10^{-6}$ cm/dBV or more, preferably $25 \times 10^{-6}$ cm/dBV or more.

Next, the specific structure of the EO polymer of the present invention will be described. In embodiments of the EO polymer of the present invention, which contains an EO molecule and a base polymer, the EO molecule may be dispersed in or bound to the base polymer.

Electro-Optic Molecule (EO Molecule)

The EO molecule used in the present invention has a structure in which a π-electron donor (donor moiety: D) and a π-electron acceptor (acceptor moiety: A) are conjugated via a π-conjugation bridge (bridge moiety: B). The EO molecule is also characterized in that the FOM and EO coefficient of an EO polymer containing the EO molecule satisfies the above equation.

The donor moiety D is, for example, a structure represented by the following formula (D-1):

[Chem. 6]

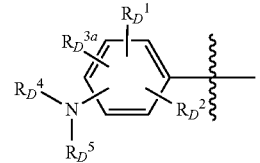

(D-1)

wherein $R_D^1$, $R_D^2$, and $R_D^3$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(=O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), and $R_D^1$, $R_D^2$, and $R_D^3$ each may have one or more identical or different substituents;

$R_D^4$ and $R_D^5$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group), or —$R^6$—NCO (wherein $R^6$ is a hydrocarbon group), and $R_D^4$ and $R_D^5$ each may have one or more identical or different substituents.

In the structure represented by the above formula (D-1), a substituent other than —$R_D^1$, —$R_D^2$, —$R_D^3$, and —$NR_D^4 R_D^5$ in the benzene ring is a hydrogen atom.

The bridge moiety B is not particularly limited as long as the bridge moiety B has a conjugated system. For example, the bridge moiety B may be a group represented by the formula (B-I) or (B-IV) given later.

The acceptor moiety A is, for example, a structure represented by the following formula (A-1):

[Chem. 7]

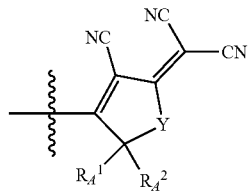

(A-I)

wherein $R_A^1$ and $R_A^2$ independently represent a hydrogen atom, an alkyl group, an alkenyl group, a cycloalkyl group, a cycloalkenyl group, an alkoxy group, an aryl group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), and $R_A{}^1$ and $R_A{}^2$ each may have one or more identical or different substituents; and Y represents —$CR_A{}^1R_A{}^2$—, —O—, —S—, —SO—, —$SiR_A{}^1R_A{}^2$—, —$NR_A{}^1$—, or —$C(=CH_2)$—.

The EO molecule used in the present invention may be any EO molecule that has the donor moiety D, the bridge moiety B, and the acceptor moiety A. Preferred are EO molecules at least having the acceptor moiety A. A specific example of the EO molecule used in the present invention is a compound represented by the following formula (1):

[Chem. 8]

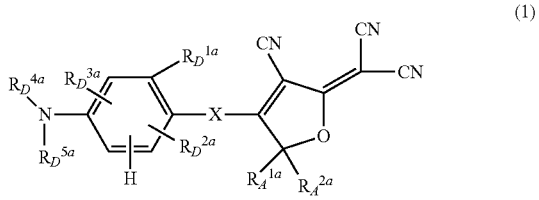

(1)

wherein
$R_D{}^{1a}$, $R_D{}^{2a}$, and $R_D{}^{3a}$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —$OC(=O)R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), and $R_D{}^{1a}$, $R_D{}^{2a}$, and $R_D{}^{3a}$ each may have one or more identical or different substituents;

$R_D{}^{4a}$ and $R_D{}^{5a}$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group), or —$R^6$—NCO (wherein $R^6$ is a hydrocarbon group), and $R_D{}^{4a}$ and $R_D{}^{5a}$ each may have one or more identical or different substituents;

X represents a linking group; and $R_A{}^{1a}$ and $R_A{}^{2a}$ independently represent a hydrogen atom, an alkyl group, an alkenyl group, a cycloalkyl group, a cycloalkenyl group, an alkoxy group, an aryl group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), and $R_A{}^{1a}$ and $R_A{}^{2a}$ each may have one or more identical or different substituents.

$R_D{}^{1a}$, $R_D{}^{2a}$, and $R_D{}^{3a}$ in the formula (1) correspond to $R_D{}^1$, $R_D{}^2$, and $R_D{}^3$ in the formula (D-1), respectively, and independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —$OC(=O)R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group). In addition, $R_D{}^{1a}$, $R_D{}^{2a}$, and $R_D{}^{3a}$ each may have one or more identical or different substituents.

The alkyl group represented by $R_D{}^1$ or $R_D{}^{1a}$, $R_D{}^2$ or $R_D{}^{2a}$, and $R_D{}^3$ or $R_D{}^{3a}$ is, for example, a $C_{1-20}$ a straight- or branched-chain saturated hydrocarbon. Specific examples include a methyl group, an ethyl group, a n-propyl group, an isopropyl group, a n-butyl group, an isobutyl group, a sec-butyl group, a tert-butyl group, a pentyl group, an isopentyl group, a hexyl group, an isohexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. Preferable examples include $C_{1-6}$ alkyl groups, and more preferable examples include a methyl group, an ethyl group, a propyl group, an isopropyl group, a butyl group, an isobutyl group, a sec-butyl group, and a tert-butyl group.

The alkoxy group represented by $R_D{}^1$ or $R_D{}^{1a}$, $R_D{}^2$ or $R_D{}^{2a}$, and $R_D{}^3$ or $R_D{}^{3a}$ is defined as an alkyloxy group in which an oxygen atom is substituted with one "alkyl group" as described above. Examples of the alkoxy group include $C_{1-20}$ straight- or branched-chain alkoxy groups. Specific examples include a methoxy group, an ethoxy group, a n-propoxy group, an isopropoxy group, a n-butoxy group, an isobutoxy group, a sec-butoxy group, a tert-butoxy group, a pentyloxy group, an isopentyloxy group, a hexyloxy group, an isohexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, and an icosyloxy group. Preferable examples include $C_{1-6}$ alkoxy groups, and more preferable examples include a methoxy group, an ethoxy group, a n-propoxy group, an isopropoxy group, a butoxy group, an isobutoxy group, a sec-butoxy group, and a tert-butoxy group.

The aryloxy group represented by $R_D{}^1$ or $R_D{}^{1a}$, $R_D{}^2$ or $R_D{}^{2a}$, and $R_D{}^3$ or $R_D{}^{3a}$ is defined as a group in which an oxygen atom is substituted with one $C_{6-20}$ monocyclic or condensed polycyclic aryl group. The "monocyclic aryl group (monocyclic aromatic hydrocarbon group)" has preferably 5 to 10 carbon atoms, more preferably 5 to 7 carbon atoms, still more preferably 5 or 6 carbon atoms, yet still more preferably 6 carbon atoms. For example, a monocyclicaryl group having 5 to 10 carbon atom means an aryl group in which the 5 to 10 carbon atoms form a ring. More specifically, a monocyclic aryl group having 6 carbon atoms is a phenyl group. The "polycyclic aryl group (polycyclic aromatic hydrocarbon group)" is, for example, a bicyclic or tricyclic condensed aryl group. The bicyclic condensed aryl group has preferably 8 to 12 carbon atoms, more preferably 9 or 10 carbon atoms, still more preferably 10 carbon atoms. For example, a polycyclic aryl group having 10 carbon atoms is a naphthyl group. Preferable examples of the aryloxy group include a phenoxy group and a naphthyloxy group, and more preferable examples include a phenoxy group.

The aralkyloxy group represented by $R_D{}^1$ or $R_D{}^{1a}$, $R_D{}^2$ or $R_D{}^{2a}$, and $R_D{}^3$ or $R_D{}^{3a}$ is defined as a group in which an "alkoxy group" as described above is substituted with at least one "monocyclic or polycyclic aryl group". Specific examples of the aralkyloxy group include a benzyloxy group, a 1-phenylethyloxy group, a phenethyloxy group, a 1-naphthylmethyloxy group, a 2-naphthylmethyloxy group, a 1-naphthylethyloxy group, and a 2-naphthylethyloxy group.

The silyloxy group represented by $R_D^1$ or $R_D^{1a}$, $R_D^2$ or $R_D^{2a}$, and $R_D^3$ or $R_D^{3a}$ is, for example, a tert-butyldiphenylsiloxy group, a tert-butyldimethylsiloxy group, or the like.

The alkenyloxy group represented by $R_D^1$ or $R_D^{1a}$, $R_D^2$ or $R_D^{2a}$, and $R_D^3$ or $R_D^{3a}$ is defined as a group in which an oxygen atom is substituted with one "alkenyl group". The "alkenyl group" used here refers to a $C_{2-20}$ straight- or branched-chain hydrocarbon containing at least one carbon-carbon double bond, for example, a vinyl group, an allyl group, an isopropenyl group, a 1-propen-1-yl group, a 2-methylallyl group, a butenyl group, a pentenyl group, an isopentenyl group, a hexenyl group, a heptenyl group, an octenyl group, a palmitoleyl group, an oleyl group, or a linoleyl group. Preferable examples of the alkenyloxy group include $C_{2-6}$ alkenyloxy groups, and more preferable examples include an ethenyloxy group, a 1-propenyloxy group, 2-propenyloxy group, a 1-methylethenyloxy group, a 1-butenyloxy group, a 2-butenyloxy group, a 3-butenyloxy group, a 1-methyl-1-propenyloxy group, a 1-methyl-2-propenyloxy group, a 2-methyl-1-propenyloxy group, and a 2-methyl-2-propenyloxy group.

The alkynyloxy group represented by $R_D^1$ or $R_D^{1a}$, $R_D^2$ or $R_D^{2a}$, and $R_D^3$ or $R_D^{3a}$ is defined as a group in which an oxygen atom is substituted with one "alkynyl group". The "alkynyl group" used here refers to a $C_{2-20}$ straight- or branched-chain hydrocarbon containing at least one carbon-carbon triple bond, for example, an ethynyl group, a 1-propynyl group, a 2-propynyl group, a butynyl group, a pentynyl group, a hexynyl group, a heptynyl group, or an octynyl group. Preferable examples of the alkynyloxy group include $C_{3-6}$ alkynyloxy groups, and more preferable examples include a 2-propynyloxy group, a 1-methyl-2-propynyloxy group, a 1,1-dimethyl-2-propynyloxy group, a 2-butynyloxy group, a 3-butynyloxy group, a 1-pentynyloxy group, a 2-pentynyloxy group, a 3-pentynyloxy group, and a 4-pentynyloxy group.

Examples of the hydrocarbon group represented by $R^1$, $R^2$, $R^4$, $R^5$, and $R^6$ in —$R^1$—OH, —$OR^2$—OH, —$R^4$—$NH_2$, —$R^5$—SH, and —$R^6$—NCO represented by $R_D^1$ or $R_D^{1a}$, $R_D^2$ or $R_D^{2a}$, and $R_D^3$ or $R_D^{3a}$ include aliphatic groups {e.g., alkylene groups [e.g., $C_{1-10}$ alkylene groups (e.g., a methylene group, an ethylene group, a propylene group, a butylene group, etc.), preferably $C_{1-4}$ alkylene groups etc.]} and aromatic groups [e.g., $C_{6-20}$ aromatic groups (e.g., a phenylene group, a benzylene group, etc.) etc.]. Particularly preferred are $C_{1-10}$ alkylene groups and $C_{6-20}$ aromatic groups.

Specific examples of —$R^1$—OH include hydroxyalkyl groups (e.g., hydroxy $C_{1-10}$ alkyl groups such as a hydroxymethyl group, a hydroxyethyl group, a hydroxypropyl group, a hydroxybutyl group, etc.), hydroxyaryl groups (e.g., hydroxy $C_{6-10}$ aryl groups such as a hydroxyphenyl group etc.), and hydroxyaralkyl groups (e.g., hydroxy $C_{6-10}$ aryl $C_{1-4}$ alkyl groups such as a hydroxybenzyl group etc.).

Specific examples of —$OR^2$—OH include hydroxyalkoxy groups (e.g., hydroxy $C_{1-10}$ alkoxy groups such as a hydroxymethoxy group, a hydroxyethoxy group, a hydroxypropoxy group, a hydroxybutoxy group, etc.), hydroxyaryloxy groups (e.g., hydroxy $C_{6-10}$ aryloxy groups such as a hydroxyphenoxy group etc.), and hydroxyaralkyloxy groups (e.g., hydroxy $C_{6-10}$ aryl $C_{1-4}$ alkyloxy groups such as a hydroxybenzyloxy group etc.).

Specific examples of —$R^4$—$NH_2$ include aminoalkyl groups (e.g., amino $C_{1-10}$ alkyl groups such as an aminomethyl group, an aminoethyl group, an aminopropyl group, an aminobutyl group, etc.).

Specific examples of —$R^5$—SH include mercaptoalkyl groups (e.g., mercapto $C_{1-10}$ alkyl groups such as a mercaptomethyl group, a mercaptoethyl group, a mercaptopropyl group, a mercaptobutyl group, etc.).

Specific examples of —$R^6$—NCO include isocyanatoalkyl groups (e.g., isocyanato $C_{1-10}$ alkyl groups such as an isocyanatomethyl group, an isocyanatoethyl group, an isocyanatopropyl group, an isocyanatobutyl group, etc.).

Examples of the hydrocarbon group represented by $R^3$ in —OC(=O) $R^3$ represented by $R_D^1$ or $R_D^{1a}$, $R_D^2$ or $R_D^{2a}$, and $R_D^3$ or $R_D^{3a}$ include aliphatic groups [e.g., $C_{1-10}$ alkyl groups (e.g., a methyl group, an ethyl group, a propyl group, a butyl group, etc.), $C_{2-10}$ alkenyl groups (e.g., an ethenyl group, a propenyl group, a butenyl group, etc.), preferably $C_{1-6}$ alkyl groups, $C_{2-6}$ alkenyl groups, etc.]; alicyclic groups [e.g., $C_{3-12}$ cycloalkyl groups (e.g., a cyclopropyl group, a cyclobutyl group, a cyclopentyl group, a cyclohexyl group, etc.), preferably $C_{3-7}$ cycloalkyl groups etc.]; and aromatic groups {e.g., $C_{6-20}$ aromatic groups [e.g., $C_{6-20}$ aryl groups (e.g., a phenyl group, a tolyl group, a xylyl group, a naphthyl group, etc.), $C_{7-20}$ aralkyl groups (e.g., a benzyl group etc.), etc.]}. Among these, preferred are aliphatic groups, and more preferred are $C_{2-10}$ alkenyl groups.

Any one of $R_D^1$, $R_D^2$ and $R_D^3$ and any one of $R_D^{1a}$, $R_D^{2a}$ and $R_D^{3a}$ are preferably an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(=O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group).

$R_D^{4a}$ and $R_D^{5a}$ in the formula (1) correspond to $R_D^4$ and $R_D^5$ in the formula (D-1), respectively, and independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group), or —$R^6$—NCO (wherein $R^6$ is a hydrocarbon group). In addition, $R_D^{4a}$ and $R_D^{5a}$ each may have one or more identical or different substituents.

Examples of the alkyl group represented by $R_D^4$ or $R_D^{4a}$ and $R_D^5$ or $R_D^{5a}$ include those listed above for the alkyl group represented by $R_D^1$ or $R_D^{1a}$, $R_D^2$ or $R_D^{2a}$, and $R_D^3$ or $R_D^{3a}$. Preferable examples include $C_{1-6}$ alkyl groups. More preferable examples include a methyl group, an ethyl group, a n-propyl group, an isopropyl group, a n-butyl group, an isobutyl group, a sec-butyl group, a tert-butyl group, a pentyl group, an isopentyl group, a hexyl group, and an isohexyl group.

The haloalkyl group represented by $R_D^4$ or $R_D^{4a}$ and $R_D^5$ or $R_D^5$a is, for example, a group in which an "alkyl group" as described above is substituted with one or more identical or different halogen atoms (e.g., fluorine atoms, chlorine atoms, bromine atoms, iodine atoms, etc.). Preferable examples of the haloalkyl group include halo $C_{1-6}$ alkyl groups, and more preferable examples include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, a 2-bromoethyl group, a 1-bromopropyl group, a 2-bromopropyl group, a 3-bromopropyl group, and an iodomethyl group.

The acyloxyalkyl group represented by $R_D^4$ or $R_D^{4a}$ and $R_D^5$ or $R_D^{5a}$ is, for example, a straight- or branched-chain $C_{1-20}$ alkyl group substituted with one or more identical or different acyloxy groups.

The silyloxyalkyl group represented by $R_D^4$ or $R_D^{4a}$ and $R_D^5$ or $R_D^{5a}$ is, for example, a straight- or branched-chain $C_{1-20}$ alkyl group substituted with at least one silyloxy group.

The aryl group represented by $R_D^4$ or $R_D^{4a}$ and $R_D^5$ or $R_D^{5a}$ is, for example, a monocyclic aryl group, a polycyclic aryl group, or the like.

The hydrocarbon group in —$R^1$—OH, —$R^4$—$NH_2$, —$R^5$—SH, and —$R^6$—NCO represented by $R_D^4$ or $R_D^{4a}$ and $R_D^5$ or $R_D^{5a}$ is not particularly limited as long as the hydrocarbon group is the same as the hydrocarbon group defined above. Specific examples of the hydrocarbon group are the same as those listed above for —$R^1$—OH, —$R^4$—$NH_2$, —$R^5$—SH, and —$R^6$—NCO represented by $R_D^1$ or $R_D^{1a}$, $R_D^2$ or $R_D^{2a}$, and $R_D^3$ or $R_D^{3a}$, including hydroxyalkyl groups (e.g., hydroxy $C_{1-10}$ alkyl groups such as a hydroxymethyl group, a hydroxyethyl group, a hydroxypropyl group, a hydroxybutyl group, etc.), hydroxyaryl groups (e.g., hydroxy $C_{6-10}$ aryl groups such as a hydroxyphenyl group etc.), and hydroxyaralkyl groups (e.g., hydroxy $C_{6-10}$ aryl $C_{1-4}$ alkyl groups such as a hydroxybenzyl group etc.).

The π-electron donor used in the present invention can have a structure having the substituents described above, for example. The EO molecule used in the present invention is capable of binding to the base polymer via $R_D^1$ or $R_D^{1a}$, $R_D^2$ or $R_D^{2a}$, $R_D^3$ or $R_D^{3a}$, $R_D^4$ or $R_D^{4a}$, and/or $R_D^5$ or $R_D^{5a}$.

X in the formula (1) represents a linking group and forms a π-conjugation bridge in the present invention.

The linking group is not particularly limited as long as it is a known π-conjugation bridge, for example, a group represented by the following formula (B-I):

[Chem. 9]

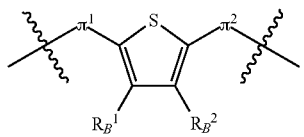

(B-I)

wherein
  $\pi^1$ and $\pi^2$, which may be the same or different, independently represent a carbon-carbon conjugated π-bond, and $\pi^1$ and $\pi^2$ each may have one or more identical or different substituents; and
  $R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group), $R_B^1$ and $R_B^2$ each may have one or more identical or different substituents, and $R_B^1$ and $R_B^2$ may form a ring together with the two carbon atoms to which they are bound.

Examples of $\pi^1$ and $\pi^2$ in the formula (B-I) include a structure represented by the following formula (B-IV):

[Chem. 10]

(B-IV)

wherein n represents an integer of 1 to 5.

$R_B^1$ and $R_B^2$ in the formula (B-I) independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group). In addition, $R_B^1$ and $R_B^2$ each may have one or more identical or different substituents, and $R_B^1$ and $R_B^2$ may form a ring together with the two carbon atoms to which they are bound. $R_B^1$, $R_B^2$, or both in the formula (B-I) serve to link the base polymer to the EO molecule.

Examples of the alkyl group represented by $R_B^1$ and $R_B^2$ include those listed above for the alkyl group represented by $R_D^4$ or $R_D^{4a}$ and $R_D^5$ or $R_D^{5a}$. Preferably, the alkyl group is, for example, a methyl group, an ethyl group, a propyl group, an isopropyl group, a n-butyl group, an isobutyl group, a sec-butyl group, a tert-butyl group, a pentyl group, an isopentyl group, a hexyl group, an isohexyl group, a heptyl group, or the like. The alkyl group may be an alkyl group of 1 to 5 carbon atoms, for example, a methyl group, an ethyl group, a propyl group, an isopropyl group, a n-butyl group, an isobutyl group, a sec-butyl group, a tert-butyl group, a pentyl group, or the like.

Examples of the alkoxy group represented by $R_B^1$ and $R_B^2$ include those listed above for the alkoxy group represented by represented by $R_D^1$ or $R_D^{1a}$, $R_D^2$ or $R_D^{2a}$, and $R_D^3$ or $R_D^{3a}$. Specific examples of the alkoxy group include a methoxy group, an ethoxy group, a n-propoxy group, an isopropoxy group, a n-butoxy group, an isobutoxy group, a sec-butoxy group, and a tert-butoxy group. Preferred are a methoxy group and the like.

Examples of the aryl group represented by $R_B^1$ and $R_B^2$ include those listed above for the aryl group represented by $R_D^4$ or $R_D^{4a}$ and $R_D^5$ or $R_D^{5a}$. Specific examples of the aryl group include a phenyl group, and a naphthyl group. Preferred are a phenyl group and the like.

Examples of the alkenyl group represented by $R_B^1$ and $R_B^2$ include those listed above for the alkenyl group in the definition of the alkenyloxy group represented by $R_D^1$ or $R_D^{1a}$, $R_D^2$ or $R_D^{2a}$, and $R_D^3$ or $R_D^{3a}$. Specific examples of the alkenyl group include an ethenyl group, a propenyl group, a butenyl group, a pentenyl group, and hexenyl group.

Examples of the cycloalkyl group represented by $R_B^1$ and $R_B^2$ include $C_{3-15}$ monocyclic or polycyclic saturated aliphatic groups. Specific examples of the cycloalkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group. Preferred are a cyclohexyl group and the like.

Examples of the cycloalkenyl group represented by $R_B^1$ and $R_B^2$ include $C_{3-15}$ monocyclic or polycyclic unsaturated aliphatic groups. Specific examples of the cycloalkenyl group include a cyclopropenyl group, a cyclopentenyl group, a cyclohexenyl group, a cycloheptynyl group, a cyclooctenyl group, a cyclopentadienyl group, a cyclohexadienyl group, a cycloheptadienyl group, and a cyclooctadienyl group.

Examples of the haloalkyl group represented by $R_B^1$ and $R_B^2$ include those listed above for the haloalkyl group represented by $R_D^4$ or $R_D^{4a}$ and $R_D^5$ or $R_D^{5a}$. Specific examples of the haloalkyl group include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group. Preferred are a trifluoromethyl group and the like.

The aralkyl group represented by $R_B^1$ and $R_B^2$ is, for example, an alkyl group substituted with at least one aryl group. Examples of the aryl group include those listed above for the aryl group represented by $R_D^4$ or $R_D^{4a}$ and $R_D^5$ or $R_D^{5a}$. Examples of the alkyl group include those listed above for the alkyl group represented by $R_D^4$ or $R_D^{4a}$ and $R_D^5$ or $R_{Da}$. Specific examples of the aralkyl group include a benzyl group, a 1-phenylethyl group, a phenethyl group, a 1-naphthylmethyl group, a 2-naphthylmethyl group, a 1-naphthylethyl group, and a 2-naphthylethyl group. Preferred are a benzyl group and the like.

Examples of the aryloxy group represented by $R_B^1$ and $R_B^2$ include those listed above for the aryloxy group represented by $R_D^1$ or $R_D^{1a}$, $R_D^2$ or $R_D^{2a}$, and $R_D^3$ or $R_D^{3a}$. Specific examples of the aryloxy group include a phenoxy group and a naphthyloxy group. Preferred are a phenoxy group and the like.

Examples of the aralkyloxy group represented by $R_B^1$ and $R_B^2$ include those listed above for the aralkyloxy group represented by $R_D^1$ or $R_D^{1a}$, $R_D^2$ or $R_D^{2a}$, and $R_D^3$ or $R_D^{3a}$. Specific examples of the aralkyloxy group include a benzyloxy group, a phenethyloxy group, a 1-naphthylmethoxy group, and a 2-naphthylmethoxy group. Preferred are a benzyloxy group and the like.

The hydrocarbon group in —$R^1$—OH, —O$R^2$—OH, —$R^4$—NH$_2$, —$R^5$—SH, and —$R^6$—NCO represented by $R_B^1$ and $R_B^2$ is not particularly limited as long as the hydrocarbon group is the same as the hydrocarbon group defined above. Specific examples of the hydrocarbon group are the same as those listed above for —$R^1$—OH, —$R^4$—NH$_2$, —$R^5$—SH, and —$R^6$—NCO represented by $R_D^1$ or $R_D^{1a}$, $R_D^2$ or $R_D^{2a}$, and $R_D^3$ or $R_D^{3a}$, including hydroxyalkyl groups (e.g., hydroxy $C_{1-10}$ alkyl groups such as a hydroxymethyl group, a hydroxyethyl group, a hydroxypropyl group, a hydroxybutyl group, etc.) and hydroxyalkoxy groups (e.g., hydroxy $C_{1-10}$ alkoxy groups such as a hydroxymethoxy group, a hydroxyethoxy group, a hydroxypropoxy group, a hydroxybutoxy group, etc.).

Examples of the hydrocarbon group represented by $R^1$, $R^2$, $R^4$, $R^5$, and $R^6$ in the definition of $R_B^1$ and $R_B^2$ in the formula (B-I) include those listed above for the hydrocarbon group represented by $R^1$, $R^2$, $R^4$, $R^5$, and $R^6$ in the definition of the formula (1) shown above.

The ring that may be formed from $R_B^1$ and $R_B^2$ in the formula (B-I) is not particularly limited and is, for example, a structure represented by the following:

[Chem. 11]

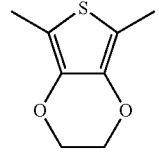

or the like.

$R_A^{1a}$ and $R_A^{2a}$ in the formula (1) correspond to $R_A^1$ and $R_A^2$ in the formula (A-1), respectively, and independently represent a hydrogen atom, an alkyl group, an alkenyl group, a cycloalkyl group, a cycloalkenyl group, an alkoxy group, an aryl group, a hydroxy group, —$R^1$—OH (wherein $R^1$ is a hydrocarbon group), —O$R^2$—OH (wherein $R^2$ is a hydrocarbon group), an amino group, —$R^4$—NH$_2$ (wherein $R^4$ is a hydrocarbon group), a thiol group, —$R^5$—SH (wherein $R^5$ is a hydrocarbon group), —NCO, or —$R^6$—NCO (wherein $R^6$ is a hydrocarbon group). In addition, $R_A^{1a}$ and $R_A^{2a}$ each may have one or more identical or different substituents. $R_A^{1a}$, $R_A^{2a}$ or both in the formula (1) and $R_A^1$, $R_A^2$ or both in the formula (A-1) serve to link the base polymer to the EO molecule.

Examples of the alkyl group represented by $R_A^1$ or $R_A^{1a}$ and $R_A^2$ or $R_A^{2a}$ include those listed above for the alkyl group represented by $R_D^4$ or $R_D^{4a}$ and $R_D^5$ or $R_D^{5a}$.

Examples of the alkenyl group represented by $R_A^1$ or $R_A^{1a}$ and $R_A^2$ or $R_A^{2a}$ include those listed above for the alkenyl group represented by $R_B^1$ and $R_B^2$.

Examples of the cycloalkyl group represented by $R_A^1$ or $R_A^{1a}$ and $R_A^2$ or $R_A^{2a}$ include those listed above for the cycloalkyl group represented by $R_B^1$ and $R_B^2$.

Examples of the cycloalkenyl group represented by $R_A^1$ or $R_A^{1a}$ and $R_A^2$ or $R_A^{2a}$ include those listed above for the cycloalkenyl group represented by $R_B^1$ and $R_B^2$.

Examples of the alkoxy group represented by $R_A^1$ or $R_A^{1a}$ and $R_A^2$ or $R_A^{2a}$ include those listed above for the alkoxy group represented by $R_D^1$ or $R_D^{1a}$, $R_D^2$ or $R_D^{2a}$, and $R_D^3$ or $R_D^{3a}$.

Examples of the aryl group represented by $R_A^1$ or $R_A^{1a}$ and $R_A^2$ or $R_A^{2a}$ include those listed above for the aryl group represented by $R_D^4$ or $R_D^{4a}$ and $R_D^5$ or $R_D^{5a}$.

Examples of the hydrocarbon group represented by $R^1$, $R^2$, $R^4$, $R^5$, and $R^6$ in the definition of $R_A^1$ or $R_A^{1a}$ and $R_A^2$ or $R_A^{2a}$ include those listed above for the hydrocarbon group represented by $R^1$, $R^2$, $R^4$, $R^5$, and $R^6$ in the definition of $R_D^1$ or $R_D^{1a}$, $R_D^2$ or $R_D^{2a}$, and $R_D^3$ or $R_D^{3a}$.

Examples of the "substituent" that $R_D^1$ or $R_D^{1a}$, $R_D^2$ or $R_D^{2a}$, $R_D^3$ or $R_D^{3a}$, $R_D^4$ or $R_D^{4a}$, $R_D^5$ or $R_D^{5a}$, $R_B^1$, $R_B^2$, $R_A^1$ or $R_A^{1a}$, and $R_A^2$ or $R_A^{2a}$ may have include an alkyl group, a haloalkyl group, a cycloalkyl group, an aryl group, an alkenyl group, an alkynyl group, an alkoxy group, a hydroxy group, an oxiranyl group, a mercapto group, an amino group, a carbamoyl group, a sulfamoyl group, a carboxy group, an alkoxycarbonyl group, a sulfo group, a sulfino group, a phosphono group, a nitro group, a cyano group, an amidino group, an imino group, a dihydroborono group, a halogen atom (fluorine, chlorine, bromine and iodine atoms, etc.), a sulfinyl group, a sulfonyl group, an acyl group, an oxo group, and a thioxo group. $R_D^1$ or $R_D^{1a}$, $R_D^2$ or $R_D^{2a}$, $R_D^3$ or $R_D^{3a}$, $R_D^4$ or $R_D^{4a}$, $R_D^5$ or $R_D^{5a}$, $R_B^1$, $R_B^2$, $R_A^1$ or $R_A^{1a}$, and $R_A^2$ or $R_A^{2a}$ may have a single substituent or two or more identical or different substituents.

In particular, the "substituent" that $R_A^1$ or $R_A^{1a}$ and $R_A^2$ or $R_A^{2a}$ may have is preferably a halogen atom or an aryl group, and the number of the halogen atom or the aryl group is, for example, 1 to 5.

The halogen atom that $R_A^1$ or $R_A^{1a}$ and $R_A^2$ or $R_A^{2a}$ may have is a fluorine, chlorine, bromine or iodine atom. Preferably, the halogen atom is one or more kinds selected from the group consisting of fluorine, chlorine, and bromine.

In preferable embodiments of $R_A^1$ or $R_A^{1a}$ and $R_A^2$ or $R_A^{2a}$, at least one of $R_A^1$ and $R_A^2$ and at least one of $R_A^{1a}$ and $R_A^{2a}$ are an aryl group having a halogen atom, an aryl group having a haloalkyl group, an aryl group having a cycloalkyl group, or an aryl group having an aryl group optionally having a halogen atom. Specifically, at least one of $R_A^1$ and $R_A^2$ and at least one of $R_A^{1a}$ and $R_A^{2a}$ are, for example, a fluorochlorophenyl group, a trifluoromethyl chlorophenyl group, a trifluoromethylphenyl group, a trifluorophenyl group, a bromophenyl group, a dichlorophenyl group, a difluorophenyl group, a fluorophenyl group, a pentafluorophenyl group, a cyclohexylphenyl group, or a biphenyl group. Specific examples of the combination of $R_A^1$ or $R_A^{1a}$ and $R_A^2$ or $R_A^{2a}$ include cases where $R_A^1$ is an alkyl group and $R_A^2$ is an aryl group having a halogen atom, an aryl group having a haloalkyl group, an aryl group having a cycloalkyl group, or an aryl group having an aryl group optionally having a halogen atom. In these embodiments, the position where the aryl group has a substituent is not particularly limited and may be an ortho, para, or meta position.

The π-electron acceptor used in the present invention can have a structure having the substituents described above, for example. Specific examples of the π-electron acceptor include the structures illustrated below. Accordingly, the EO molecule used in the present invention is exemplified by EO molecules having any of the acceptor moieties illustrated below.

[Chem. 12]

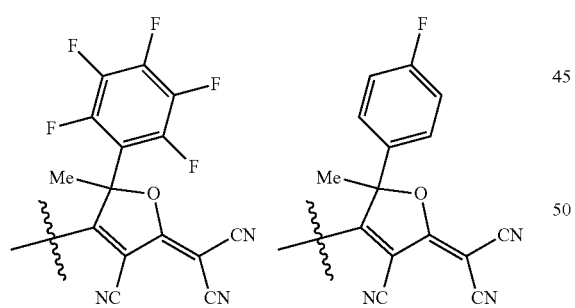

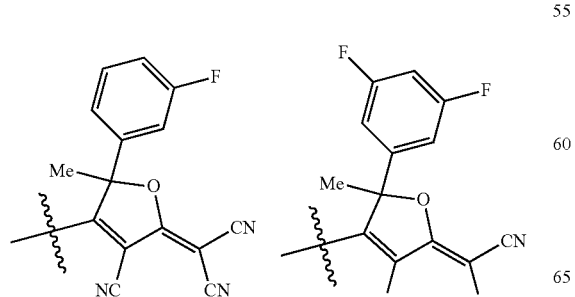

-continued

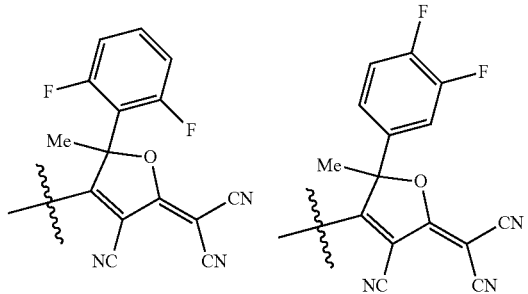

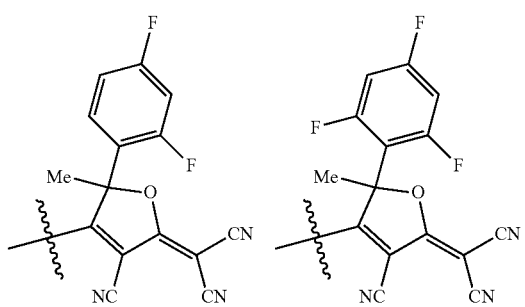

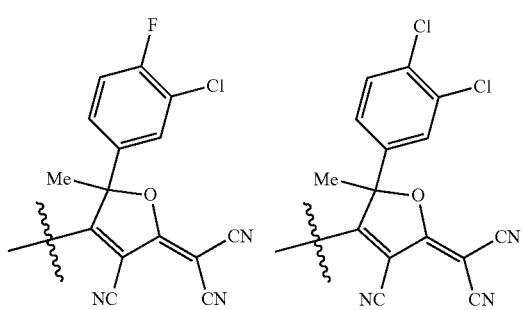

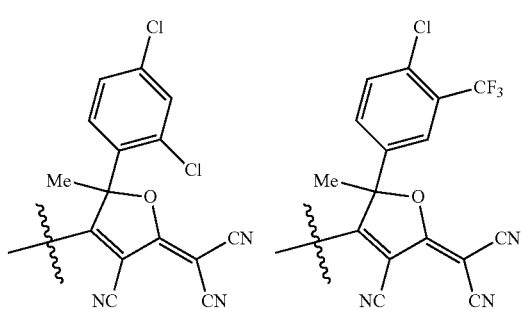

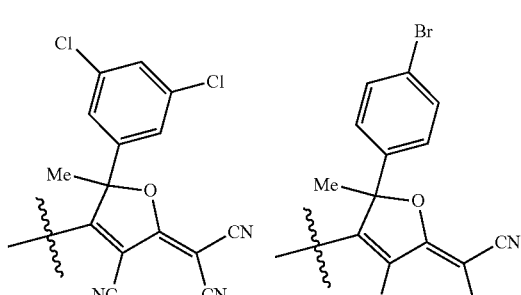

-continued

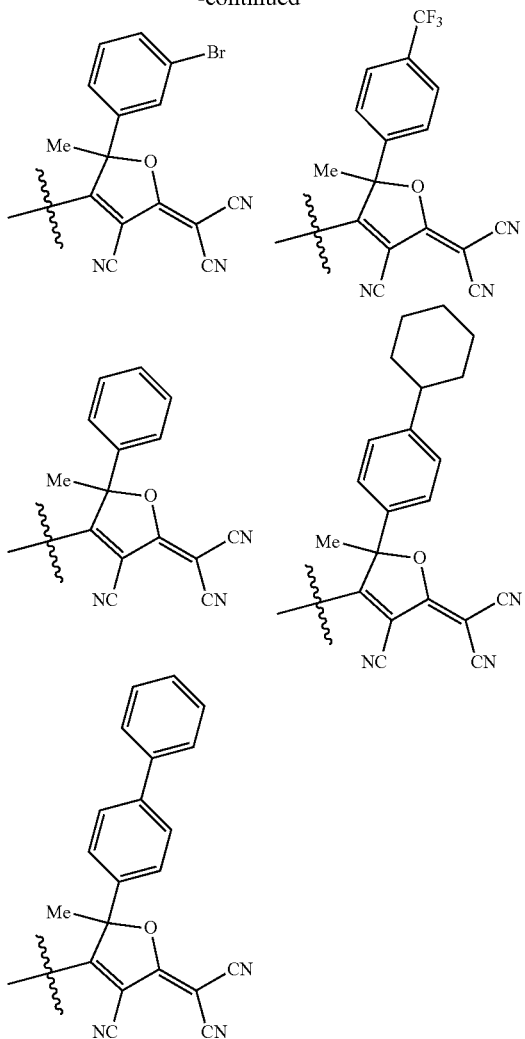

The EO molecule used in the present invention may be obtained commercially or produced by a method known per se. The EO molecule can be produced by various methods, for example, methods described in Ann., 580, 44 (1953); Angew. Chem., 92, 671 (1980); Chem. Ber., 95, 581 (1962); Macromolecules, 2001, 34, 253; Chem. Mater., 2007, 19, 1154; Org. Synth., VI, 901 (1980); Chem. Mater., 2002, 14, 2393; J. Mater. Sci., 39, 2335 (2004); "Preparative Organic Chemistry", John Wiley (1975), p. 217; J. Org. Chem., 42, 353 (1977); J. Org. Chem., 33, 3382 (1968); Synthesis, 1981, 165; WO 2011/024774, etc., appropriately modified methods thereof, combinations thereof, etc.

The EO molecule obtained or produced as above can improve the FOM of an EO polymer produced by mixing the EO molecule with a base polymer. For this reason, such an EO molecule can be used also as an FOM improving material for EO polymers.

The amount of the EO molecule contained in the EO polymer is preferably 10 wt % or more, more preferably 15 wt % or more, still more preferably 20 wt % or more to provide a desired value of the EO coefficient. In addition, the amount of the EO molecule contained in the EO polymer is preferably 60 wt % or less, more preferably 55 wt % or less, still more preferably 50 wt % or less to prevent EO molecule aggregation. In the Examples described later, EO polymers each having an EO molecule in an amount of 30 wt % are evaluated by calculating their EO coefficients and FOMs. The value 30 wt % is merely an example for convenience, and the amount of the EO molecule contained in the EO polymer of the present invention is not limited to this value.

Base Polymer

The base polymer used in the present invention may contain a compound having a hydroxyl group, a thiol group, an amino group, or other functional groups. Examples of such a compound include polyols {e.g., diols [e.g., aliphatic diols (e.g., $C_{2-10}$ alkylene glycols such as ethylene glycol), aromatic diols (e.g., dihydroxy arenes such as resorcinol, bisphenol A, etc.), etc.], triols [e.g., aliphatic triols (glycerol, trimethylolpropane, etc.) etc.], tetraols [e.g., aliphatic tetraols (e.g., pentaerythritol) etc.], etc.}; polythiols {e.g., dithiols [e.g., aliphatic dithiols (e.g., ethanedithiol etc.) etc.], tetrathiols [e.g., pentaerythritol tetrakis(3-mercaptobutyrate) etc.], etc.}; and polyamines {e.g., diamines [e.g., aliphatic diamines (e.g., $C_{2-10}$ alkanediamines such as ethylenediamine and butane-1,4-diamine) etc.] etc.}. In addition, optical-grade polymeric materials can also be used as the base polymer, for example, polyurethane, acrylic polymers (e.g., polymers containing a (meth)acrylate optionally containing an iso(thio)cyanato group), vinyl polymers, polyester, polycarbonate, poly(alkyl siloxane), epoxy resins, etc. One of these compounds and materials alone or a combination of two or more of them may be used as the base polymer.

The amount of the base polymer contained in the EO polymer is preferably 40 wt % or more, more preferably 45 wt % or more, still more preferably 50 wt % or more to achieve the object of the present invention. In addition, the amount of the base polymer contained in the EO polymer is preferably 90 wt % or less, more preferably 85 wt % or less, still more preferably 80 wt % or less in consideration of other components contained in the EO polymer.

The EO polymer of the present invention can also contain an additional component in such an amount that the additional component does not impair the effects of the present invention. Examples of such an additional component include polymerization initiators, polymerization promoters, flame retardants, ultraviolet absorbers, antistatic agents, anti-fog agents, light stabilizers, fungicides, antimicrobial agents, and foaming agents. The EO polymer of the present invention can also contain another polymeric material or another EO polymeric composition in such an amount that such a component does not impair the effects of the present invention.

The EO polymer of the present invention can be prepared by mixing all materials including the base polymer and the EO molecule, and if needed, other components as described above, using a known kneading machine. The thus-prepared mixture may be dried and pulverized into a powder, if needed.

The glass transition temperature (Tg) of the EO polymer of the present invention is not particularly limited and is usually about 105 to 230° C., preferably about 120 to 200° C. As used herein, Tg can be measured by the method described in the Examples described later.

The EO polymer of the present invention can preferably be used to form parts of optical control devices, for example, optical elements, by various processing methods. That is, one aspect of the present invention is an optical element formed from the EO polymer of the present invention.

The present invention also provides an optical control device containing an optical element formed from the EO polymer of the present invention. The optical control device is not particularly limited as long as it is an optical control device known in the field concerned, for example, an optical modulator, an optical switch, an optical transceiver, an optical phased array, a LiDAR (light detection and ranging) device, an electric field sensor, a terahertz wave generator and detector, or the like.

EXAMPLES

Hereinafter, the present invention will be described in detail by examples, but the present invention is not limited thereto.

Base Polymer Synthesis Example 1 (Copolymer A-1)

12.0 g (119.86 mmol) of methyl methacrylate (MMA), 1.42 g (9.15 mmol) of 2-(isocyanatoethyl) methacrylate (MOI), and 635 mg (3.87 mmol) of azobisisobutyronitrile (AIBN) were dissolved in 22.4 mL of toluene. After purging with argon, the solution was stirred in an oil bath at 60° C. in a light-shielding condition for 2 hours. The reaction mixture was cooled and then poured into 560 mL of diisopropyl ether (IPE), and the precipitate was collected by filtration. The precipitate was washed with IPE and dried in vacuo with heating at 70° C. to give 8.31 g of a copolymer (A-1).

1.0 g of the copolymer (A-1) obtained above was dissolved in 35 mL of tetrahydrofuran (THF). To this, 3.0 mL of methanol and 40 µL of dibutyltin dilaurate (DBTDL) were added, and the mixture was stirred in an oil bath at 60° C. for 2 hours. The reaction mixture was cooled and then poured into 400 mL of IPE, and the mixture was stirred. The precipitated powder was collected by filtration, washed with IPE, and dried in vacuo with heating at 70° C. to give 0.93 g of a methyl carbamate derivative of the copolymer (A-1) as a colorless powder.

Base Polymer Synthesis Examples 2 to 25 (Copolymers A-2 to A-25)

Copolymers (A-2) to (A-25) and their methyl carbamate derivatives were obtained in the same manner as described in Synthesis Example 1 based on the feed ratios of MMA and MOI shown in Table 1.

The glass transition temperatures (Tgs), weight-average molecular weights (Mws), and number-average molecular weights (Mns) of the obtained methyl carbamate derivatives of the copolymers were measured according to the methods described below. The results are shown in Table 1.

Glass Transition Temperature (Tg)

Glass transition temperatures were determined with a differential scanning calorimeter (Rigaku Thermo plus DSC8230, manufactured by Rigaku Corporation) in the following conditions: sample weight: 10 mg, reference: empty aluminum (Al) pan, atmosphere: nitrogen, heating rate: 10° C./minute.

Weight-Average Molecular Weight (Mw) and Number-Average Molecular Weight (Mn)

Molecular weights were measured by GPC using Alliance e2695 (manufactured by Nihon Waters K.K.) (column: Shodex GPC KF-804L (8 mmID×300 mm), developing solvent: THF, column temperature: 40° C.).

TABLE 1

| Copolymer | MMA/MOI (molar ratio) | Tg (° C.) | Mw | Mn |
| --- | --- | --- | --- | --- |
| A-1 | 13.096/1 | 112 | 49,600 | 27,500 |
| A-2 | 14.328/1 | 112 | 46,600 | 28,200 |
| A-3 | 5.960/1 | 104 | 44,500 | 24,300 |
| A-4 | 6.505/1 | 104 | 59,400 | 29,500 |
| A-5 | 12.228/1 | 110 | 48,800 | 28,900 |
| A-6 | 12.851/1 | 112 | 50,100 | 27,300 |
| A-7 | 13.041/1 | 113 | 52,400 | 27,300 |
| A-8 | 11.905/1 | 111 | 54,300 | 28,700 |
| A-9 | 12.809/1 | 112 | 51,654 | 27,775 |
| A-10 | 11.265/1 | 109 | 52,600 | 28,900 |
| A-11 | 12.565/1 | 112 | 54,600 | 27,760 |
| A-12 | 11.571/1 | 111 | 57,240 | 27,510 |
| A-13 | 14.066/1 | 112 | 50,200 | 30,100 |
| A-14 | 5.835/1 | 103 | 70,800 | 41,400 |
| A-15 | 6.377/1 | 102 | 59,200 | 30,600 |
| A-16 | 5.364/1 | 102 | 59,500 | 29,200 |
| A-17 | 3.999/1 | 98 | 75,240 | 33,550 |
| A-18 | 11.260/1 | 110 | 51,460 | 27,390 |
| A-19 | 12.246/1 | 110 | 50,210 | 29,050 |
| A-20 | 9.100/1 | 108 | 28,148 | 16,901 |
| A-21 | 12.535/1 | 111 | 55,900 | 29,600 |
| A-22 | 11.905/1 | 110 | 52,400 | 26,500 |
| A-23 | 13.041/1 | 113 | 55,800 | 29,600 |
| A-24 | 12.228/1 | 113 | 44,800 | 24,400 |
| A-25 | 12.851/1 | 112 | 54,000 | 29,000 |

EO Molecule Synthesis Example 1: 2-[4-[(E)-2-[5-[(E)-2-(benzyloxy)-4-[butyl(4-hydroxybutyl)amino] styryl]thiophen-2-yl]vinyl]-3-cyano-5-methyl-5-(perfluorophenyl)furan-2 (5H)-ylidene]malononitrile (EO-1)

(1) 3-Hydroxy-3-(perfluorophenyl)-2-butanone [3a]

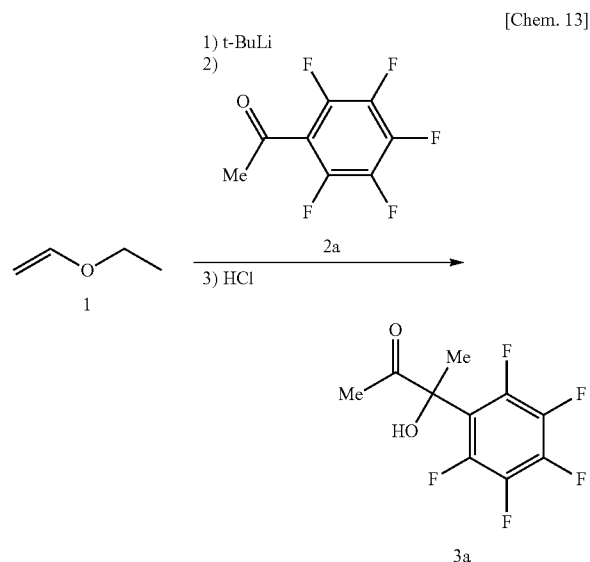

13.7 g (0.19 mol) of ethyl vinyl ether [1] was dissolved in 85 mL of THF under an argon atmosphere. To this, 100 mL (0.19 mol) of tert-butyllithium (1.9 mol solution in pentane) was added dropwise with cooling in a dry ice/acetone bath. The resulting yellow slurry was stirred for 50 minutes, the bath was removed, and the reaction mixture was heated to 0° C. Immediately thereafter, this was cooled again to −70° C., and 40 mL of a solution of 25.07 g (0.119 mol) of 2',3',4', 5',6'-pentafluoroacetophenone [2a] in THF was added dropwise over 30 minutes. After about 2 hours of stirring, the reaction mixture was slowly heated to room temperature and stirred at room temperature overnight. A mixed solution of methanol/water/concentrated hydrochloric acid (6/2/2) was added dropwise under ice cooling to render the mixture faintly acidic, followed by stirring at room temperature for 2.5 hours. The reaction mixture was subjected to concentration and subsequent ether extraction. The organic layer was washed successively with a saturated aqueous sodium chloride solution, a saturated aqueous sodium hydrogen carbonate solution, and a saturated aqueous sodium chloride solution. The washed organic layer was dehydrated over anhydrous magnesium sulfate and then concentrated. The residue was purified by silica gel column chromatography (ethylacetate/hexane=1/3) to give 16.6 g of the desired compound [3a] as a colorless oil (yield: 54.7%).

Compound 3a $^1$H-NMR (600 MHz, CDCl$_3$) δ ppm: 1.84 (3H, t), 2.23 (3H, s), 4.57 (1H, s)

$^{13}$C-NMR (150 MHz, CDCl$_3$) δ ppm: 23.46, 25.27, 78.04, 115.18, 137.92, 140.38, 145.87, 206.13

(2) 2-[3-Cyano-4,5-dimethyl-5-(perfluorophenyl)furan-2 (5H)-ylidene]malononitrile [4a]

[Chem. 14]

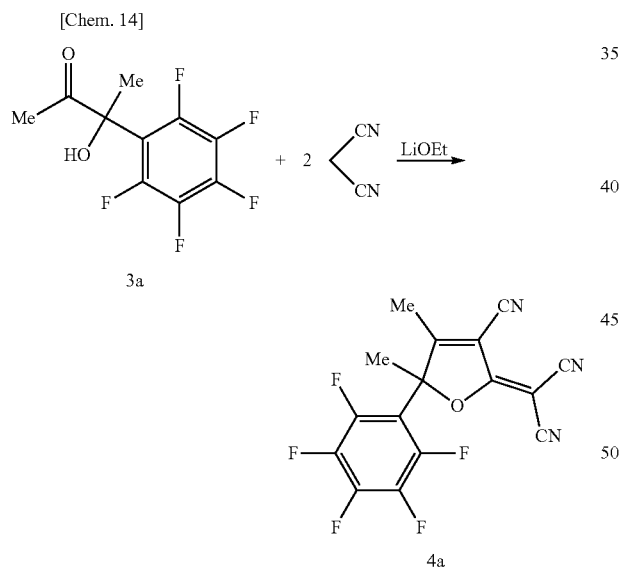

14.7 g (57.8 mmol) of 3-hydroxy-3-(perfluorophenyl)-2-butanone [3a] and 8.06 g (122.0 mmol) of malononitrile were dissolved in 60 mL of ethanol. To this, 3.1 mL of lithium ethoxide (1 mol solution in ethanol) was added, and the mixture was stirred in an oil bath at 70° C. for 16 hours. The ethanol was evaporated off in vacuo, and the residue was purified by silica gel column chromatography (chloroform/methanol=20/1). The purified product was dissolved in ethyl acetate/hexane (1/2) and then cooled. The precipitated crystals were collected by filtration to give 1.40 g of the desired compound [4a] as colorless crystals (yield: 6.9%).

Compound 4a $^1$H-NMR (600 MHz, CDCl$_3$) δ ppm: 2.13 (3H, t), 2.34 (3H, s)

$^{13}$C-NMR (150 MHz, CDCl$_3$) δ ppm: 14.18, 24.92, 61.11, 97.25, 106.14, 108.36, 109.51, 110.10, 137.55, 139.25, 144.90, 146.63, 174.30, 177.39.

(3) 2-[4-[(E)-2-[5-[(E)-2-(benzyloxy)-4-[butyl(4-hydroxybutyl)amino]styryl]thiophen-2-yl]vinyl]-3-cyano-5-methyl-5-(perfluorophenyl)furan-2 (5H)-ylidene]malononitrile [EO-1]

[Chem. 18]

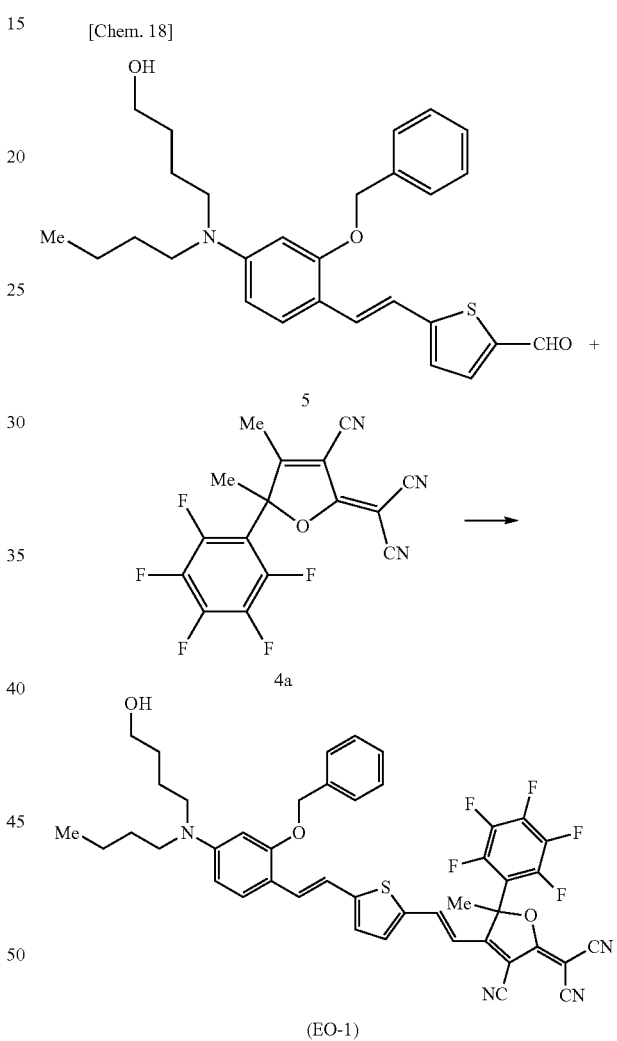

1.84 g (3.97 mmol) of 5-[(E)-2-[2-benzyloxy-4-[butyl(4-hydroxybutyl)amino]phenyl]vinyl]thiophene-2-carbaldehyde [5] and 1.4 g (3.99 mmol) of 2-[3-cyano-4,5-dimethyl-5-(perfluorophenyl)furan-2 (5H)-ylidene]malononitrile [4a] were suspended in 30 mL of ethanol and 10 mL of THF. The suspension was stirred at room temperature for 23 hours and further stirred in an oil bath at 50° C. for 17 hours. The precipitated crystals were collected by filtration and purified by silica gel column chromatography (chloroform/methanol=20/1). The purified product was crystallized from methanol, and the crystals were collected by filtration to give 2.13 g of the desired compound [EO-1] as dark brown crystals (yield: 67.4%, mp: 215 to 216° C.).

EO-1

$^1$H-NMR (600 MHz, CDCl$_3$) δ ppm: 0.93 (3H, t, J=7.6 Hz), 1.28-1.34 (2H, m), 1.48-1.64 (6H, m), 2.16 (3H, s), 3.26 (2H, t, J=7.6 Hz), 3.30 (2H, t, J=7.6 Hz), 3.62 (2H, q, J=6.2 Hz), 5.21 (2H, s), 6.11 (1H, d, J=2.7 Hz), 6.28 (1H, dd, J=2.0 Hz, 9.0 Hz), 6.47 (1H, d, J=15.1 Hz), 6.93 (1H, d, J=4.1 Hz), 7.13 (1H, d, J=15.8 Hz), 7.27 (1H, d, J=4.1 Hz), 7.34-7.45 (7H, m), 7.50 (1H, d, J=15.8 Hz).

$^{13}$C-NMR (150 MHz, CDCl$_3$) δ ppm: 13.95, 20.27, 23.81, 27.47, 29.49, 29.97, 50.95, 51.01, 56.86, 62.53, 70.38, 93.94, 96.17, 107.34, 110.30, 110.89, 111.17, 111.88, 112.85, 116.03, 126.90, 128.08, 128.74, 129.69, 131.96, 136.86, 136.98, 139.14, 139.29, 150.62, 158.23, 158.97, 169.23, 175.51.

EO Molecule Synthesis Examples 2 to 17: (EO-2 to EO-17)

EO molecules (EO-2 to EO-17) were synthesized in the same manner as in EO Molecule Synthesis Example 1 (1) to (3). The NMR measurement results of the intermediate compounds obtained in the same manner as in Synthesis Example 1 (1) are shown in Table 2. The NMR measurement results of the intermediate compounds obtained in the same manner as in Synthesis Example 1 (2) are shown in Table 3. The NMR measurement results of the obtained EO molecules (EO-2 to EO-17) are shown in Tables 4 to 7.

TABLE 2

| Structure | NMR Data |
|---|---|
| 3b | $^1$H-NMR (600 MHz, CDCl$_3$) δ ppm: 1.76 (3H, s), 2.14 (3H, s), 4.46 (1H, s), 6.83 (1H, m), 6.93 (1H, m), 7.54 (1H, m)<br>$^{13}$C-NMR (150 MHz, CDCl$_3$) δ ppm: 23.42, 24.13, 77.49, 104.79, 111.45, 125.08, 129.02, 160.12, 163.04, 208.39 |
| 3c | $^1$H-NMR (600 MHz, CDCl$_3$) δ ppm: 1.72 (3H, s), 2.09 (3H, s), 4.27 (1H, s), 7.32 (1H, dd, J = 2.0 Hz, 8.2 Hz), 7.41 (1H, d, J = 2.7 Hz), 7.58 (1H, d, J = 8.2 Hz)<br>$^{13}$C-NMR (150 MHz, CDCl$_3$) δ ppm: 24.02, 25.03, 79.23, 127.31, 129.21, 130.90, 134.30, 135.11, 137.44, 208.73 |
| 3d | $^1$H-NMR (600 MHz, CDCl$_3$) δ ppm: 1.76 (3H, s), 2.12 (3H, s), 4.51 (1H, s), 7.28 (1H, dd, J = 2.7 Hz, 8.2 Hz), 7.45 (1H, d, J = 8.2 Hz), 7.56 (1H, d, J = 2.7 Hz)<br>$^{13}$C-NMR (150 MHz, CDCl$_3$) δ ppm: 23.42, 24.24, 79.32, 125.53, 128.31, 130.63, 132.40, 132.99, 141.79, 208.48 |
| 3e | $^1$H-NMR (600 MHz, CDCl$_3$) δ ppm: 1.76 (3H, s), 2.09 (3H, s), 4.51 (1H, s), 7.33 (2H, d, J = 9.0 Hz), 7.51 (2H, d, J = 9.0 Hz)<br>$^{13}$C-NMR (150 MHz, CDCl$_3$) δ ppm: 23.38, 24.08, 79.59, 122.34, 127.84, 131.82, 140.52, 209.01 |
| 3f | $^1$H-NMR (600 MHz, CDCl$_3$) δ ppm: 1.77 (3H, s), 2.08 (3H, s), 4.55 (1H, s), 7.04-7.08 (2H, m), 7.40-7.44 (2H, m)<br>$^{13}$C-NMR (150 MHz, CDCl$_3$) δ ppm: 23.36, 24.22, 79.45, 115.57, 127.89, 137.26, 162.47, 209.38 |
| 3g | $^1$H-NMR (600 MHz, CDCl$_3$) δ ppm: 1.75 (3H, s), 2.13 (3H, s), 4.51 (1H, s), 6.77 (1H, m), 6.99 (2H, m)<br>$^{13}$C-NMR (150 MHz, CDCl$_3$) δ ppm: 23.37, 24.26, 79.51, 103.61, 109.31, 145.64, 163.18, 208.18 |
| 3h | $^1$H-NMR (600 MHz, CDCl$_3$) δ ppm: 1.81 (3H, s), 2.11 (3H, s), 4.54 (1H, s), 7.59 (2H, d, J = 8.2 Hz), 7.65 (2H, d, J = 8.2 Hz)<br>$^{13}$C-NMR (150 MHz, CDCl$_3$) δ ppm: 23.47, 24.30, 79.80, 123.94, 125.66, 126.51, 130.35, 145.42, 208.68 |
| 3i | $^1$H-NMR (600 MHz, CDCl$_3$) δ ppm: 1.79 (3H, s), 2.12 (3H, s), 4.52 (1H, s), 7.52 (1H, d, J = 8.2 Hz), 7.58 (1H, dd, J = 2.0 Hz, 8.2 Hz), 7.80 (1H, d, J = 2.0 Hz)<br>$^{13}$C-NMR (150 MHz, CDCl$_3$) δ ppm: 23.44, 24.44, 79.45, 122.67, 125.27, 128.70, 130.60, 131.79, 132.23, 140.84, 208.30 |
| 3j | $^1$H-NMR (600 MHz, CDCl$_3$) δ ppm: 1.81 (3H, t, J = 3.4 Hz), 2.20 (3H, se), 4.53 (1H, s), 6.69 (3H, m)<br>$^{13}$C-NMR (150 MHz, CDCl$_3$) δ ppm: 23.45, 25.35, 101.26, 114.06, 161.05, 161.89, 162.72, 163.34 |
| 3k | $^1$H-NMR (600 MHz, CDCl$_3$) δ ppm: 1.79 (3H, s), 2.09 (3H, s), 4.55 (1H, s), 7.30-7.33 (1H, m), 7.37-7.39 (2H, m), 7.43-7.45 (2H, m)<br>$^{13}$C-NMR (150 MHz, CDCl$_3$) δ ppm: 23.46, 24.01, 79.86, 126.00, 128.08, 128,71, 141.36, 209.65 |

TABLE 3

| | | |
|---|---|---|
| 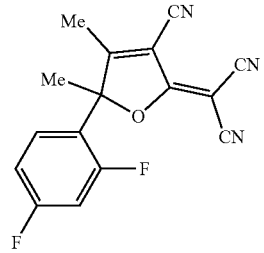 4b | <sup>1</sup>H-NMR (600 MHz, CDCl<sub>3</sub>) δ ppm: 2.03 (3H, s), 2.26 (3H, s), 6.94 (1H, m), 7.04 (1H, m), 7.42 (1H, m) <sup>13</sup>C-NMR (150 MHz, CDCl<sub>3</sub>) δ ppm: 14.25, 23.29, 59.75, 98.40, 105.67, 105.80, 105.97, 106.15, 108.80, 110.01, 110.64, 112.65, 112.79, 175.22, 179.98 | |
| 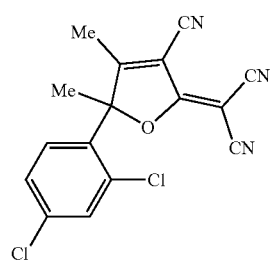 4c | <sup>1</sup>H-NMR (600 MHz, CDCl<sub>3</sub>) δ ppm: 2.04 (3H, s), 2.20 (3H, s), 7.42 (1H, dd, J = 2.1 Hz, 8.3 Hz), 7.49 (1H, d, J = 8.3 Hz), 7.50 (1H, d, J = 2.1 Hz) <sup>13</sup>C-NMR (150 MHz, CDCl<sub>3</sub>) δ ppm: 14.30, 25.37, 60.35, 99.27, 107.14, 108.80, 110.02, 110.58, 128.14, 128.38, 130.23, 132.36, 134.88, 138.23, 175.77, 179.96 | |
| 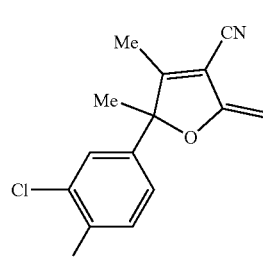 4d | <sup>1</sup>H-NMR (600 MHz, CDCl<sub>3</sub>) δ ppm: 2.01 (3H, s), 2.26 (3H, s), 7.06 (1H, dd, J = 2.1 Hz, 8.2 Hz), 7.32 (1H, d, J = 2.1 Hz), 7.57 (1H, d, J = 8.2 Hz) <sup>13</sup>C-NMR (150 MHz, CDCl<sub>3</sub>) δ ppm: 14.44, 23.64, 60.26, 99.89, 105.52, 108.61, 109.77, 110.38, 124.37, 127.31, 131.73, 134.08, 134.35, 135.42, 174.84, 180.15 | |
| 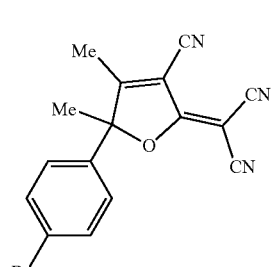 4e | <sup>1</sup>H-NMR (600 MHz, CDCl<sub>3</sub>) δ ppm: 2.01 (3H, s), 2.24 (3H, s), 7.10 (2H, d, J = 8.2 Hz), 7.62 (2H, d, J = 8.9 Hz) <sup>13</sup>C-NMR (150 MHz, CDCl<sub>3</sub>) δ ppm: 14.42, 22.51, 59.76, 100.71, 105.17, 108.73, 109.93, 110.53, 125.15, 126.71, 132.97, 133.02, 175.14, 180.94 | |
| 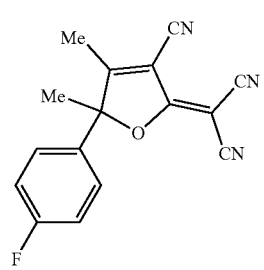 4f | <sup>1</sup>H-NMR (600 MHz, CDCl<sub>3</sub>) δ ppm: 2.02 (3H, s), 2.24 (3H, s), 7.16-7.20 (2H, m), 7.21-7.24 (2H, m) <sup>13</sup>C-NMR (150 MHz, CDCl<sub>3</sub>) δ ppm: 14.46, 22.64, 59.60, 100.78, 105.08, 108.81, 110.01, 110.62, 116.90, 127.34, 129.83, 163.72, 175.19, 181.30 | |
| 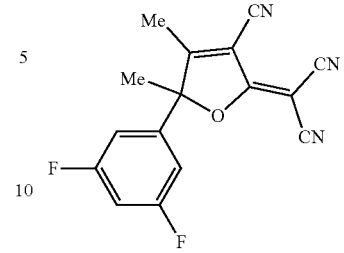 4g | <sup>1</sup>H-NMR (600 MHz, CDCl<sub>3</sub>) δ ppm: 2.00 (3H, s), 2.28 (3H, s), 6.78 (2H, m), 6.95 (1H, m) <sup>13</sup>C-NMR (150 MHz, CDCl<sub>3</sub>) δ ppm: 14.44, 22.73, 60.41, 99.73, 105.56, 106.22, 108.67, 108.70, 10.69, 110.31, 137.88, 163.57, 174.78, 179.87 | |
| 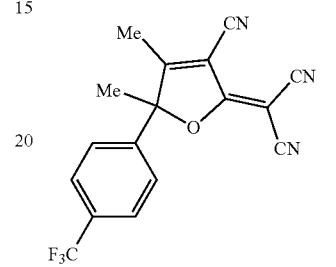 4h | <sup>1</sup>H-NMR (600 MHz, CDCl<sub>3</sub>) δ ppm: 2.06 (3H, s), 2.27 (3H, s), 7.39 (2H, d, J = 8.2 Hz), 7.76 (2H, d, J = 8.9 Hz) <sup>13</sup>C-NMR (150 MHz, CDCl<sub>3</sub>) δ ppm: 14.45, 22.80, 60.14, 100.40, 105.45, 108.63, 109.80, 110.41, 123.29, 125.62, 126.79, 132.80, 138.03, 175.04, 180.43 | |
| 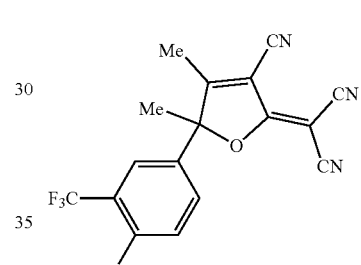 4i | <sup>1</sup>H-NMR (600 MHz, CDCl<sub>3</sub>) δ ppm: 2.05 (3H, s), 2.27 (3H, s), 7.33 (1H, dd, J = 2.1 Hz, 8.3 Hz), 7.55 (1H, d, J = 2.1 Hz), 7.65 (1H, d, J = 8.3 Hz) <sup>13</sup>C-NMR (150 MHz, CDCl<sub>3</sub>) δ ppm: 14.46, 22.79, 60.49, 99.84, 105.78, 108.57, 109.71, 110.27, 122.08, 124.31, 129.63, 129.95, 133.07, 133.35, 135.27, 174.73, 179.79 | |
| 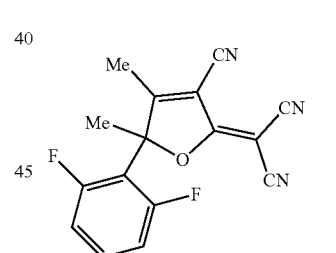 4j | <sup>1</sup>H-NMR (600 MHz, CDCl<sub>3</sub>) δ ppm: 2.09 (3H, t, J = 3.5 Hz), 2.31 (3H, s), 6.80 (2H, m) <sup>13</sup>C-NMR (150 MHz, CDCl<sub>3</sub>) δ ppm: 14.21, 24.99, 60.04, 97.77, 102.51, 105.44, 106.33, 108.71, 109.93, 110.52, 161.64, 164.12, 174.92, 179.36 | |
| 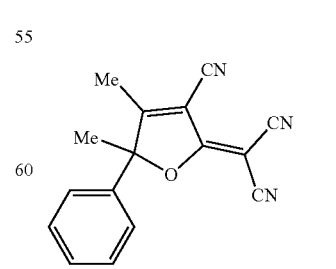 4k | <sup>1</sup>H-NMR (600 MHz, CDCl<sub>3</sub>) δ ppm: 2.03 (3H, s), 2.24 (3H, s), 7.21-7.23 (2H, m), 7.47-7.48 (3H, m) <sup>13</sup>C-NMR (150 MHz, CDCl<sub>3</sub>) δ ppm: 14.51, 22.45, 59.20, 101.42, 104.83, 108.92, 110.18, 110.75, 125.02, 129.73, 130.56, 133.93, 175.55, 181.96 | |

TABLE 4

| Structure | NMR Data |
|---|---|
| [EO-2] | ¹H-NMR (600 MHz, CDCl₃) δ ppm: 0.94 (3H, t, J = 7.60), 1.21 (1H, s), 1.29-1.35 (2H, m), 1.50-1,57 (4H, m), 1.61-1.66 (2H, m), 2.15 (3H, s), 3.27 (2H, t, J = 7.6 Hz), 3.31 (2H, t, J = 7.6 Hz), 3.65 (2H, t, J = 6.2 H), 4.25 (2H, t, J = 4.2 Hz), 4.36 (2H, q, J = 4.2 Hz), 5.17 (2H, s), 6.14 (1H, d, J = 2.1 Hz), 6.28 (1H, dd, J = 2.1 Hz, 8.9 Hz), 6.38 (1H, br), 7.10 (1H, d, J = 15.8 Hz), 7.32-7.45 (7H, m), 7.50 (1H, d, J = 16.5 Hz) ¹³C-NMR (150 MHz, CDCl₃) δ ppm: 13.95, 20.27, 23.84, 27.69, 29.51, 29.95, 46.25, 50.96, 51.01, 62.50, 64.44, 65.98, 70.33, 93.34, 96.05, 105.47, 111.92, 112.25, 112.67, 113.22, 126.91, 127.99, 128.68, 129.80, 136.84, 136.95, 150.79, 159.14, 175.97 |
| [EO-3] | ¹H-NMR (600 MHz, CDCl₃) δ ppm: 1.35 (2H, s), 1.52-1.65 (8H, m), 2.19 (3H, s), 3.31 (4H, t, J = 7.6 Hz), 3.65 (4H, t, J = 6.2 Hz), 5.21 (2H, s), 6.13 (1H, s), 6.29 (1H, dd, J = 2.1 Hz, 8.9 Hz), 6.47 (1H, d, J = 15.1 Hz), 6.93 (1H, d, J = 4.2 Hz), 7.13 (1H, d, J = 15.8 Hz), 7.27 (1H, d), 7.34-7.46 (7H, m), 7.50 (1H, d, J = 15.8 Hz) ¹³C-NMR (150 MHz, CDCl₃) δ ppm: 23.83, 27.44, 29.93, 50.98, 56.88, 62.49, 70.38, 93.96, 96.34, 105.43, 110.36, 110.87, 111.15, 111.86, 113.03, 116.18, 126.91, 126.97, 128.06, 128.74, 129.70, 131.85, 136.91, 137.02, 139.12, 139.31, 150.63, 158.10, 158.95, 169.25, 175.50 |
| [EO-4] | ¹H-NMR (600 MHz, CDCl₃) δ ppm: 1.23 (2H, s), 1.53-1,59 (4H, m), 1.62-1.67 (4H, m), 2.16 (3H, s), 3.32 (4H, t, J = 7.6 Hz), 3.65 (4H, t, J = 6.2 Hz), 4.24-4.28 (2H, m), 4.33-4.39 (2H, m), 5.18 (2H, s), 6.16 (1H, d, J = 2.0 Hz), 6.30 (1H, dd, J = 2.8 Hz, 9.0 Hz), 6.39 (1H, br), 7.10 (1H, d, J = 16.5 Hz), 7.32-7.45 (7H, m), 7.50 (1H, d, J = 15.8 Hz) ¹³C-NMR (150 MHz, CDCl₃) δ ppm: 23.86, 29.91, 50.99, 54.90, 62.48, 64.45, 65.98, 70.34, 93.36, 96.24, 105.53, 111.88, 112.41, 112.63, 113.40, 126.92, 127.97, 128.69, 129.80, 136.61, 137.01, 150.70, 159.11, 168.95, 175.97 |

TABLE 4-continued

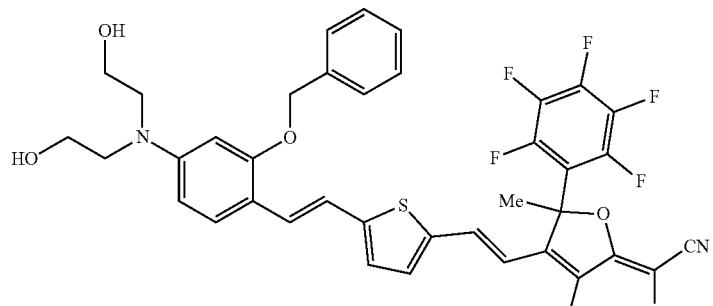

[EO-5]

¹H-NMR (600 MHz, CDCl₃) δ ppm: 2.19 (3H, s), 2.79 (2H, s), 3.59 (4H, t, J = 4.8 Hz), 3.80 (4H, t, J = 4.8 Hz), 5.20 (2H, s), 6.19 (1H, d, J = 2.0 Hz), 6.33 (1H, dd, J = 2.0 Hz, 9.0 Hz), 6.50 (1H, d, J = 15.1 Hz), 6.95 (1H, d, J = 4.2 Hz), 7.16 (1H, d, J = 15.8 Hz), 7.27 (1H, d, J = 4.2 Hz), 7.35-7.46 (7H, m, Ph), 7.48 (1H, d, J = 15.8 Hz)
¹³C-NMR (150 MHz, CDCl₃) δ ppm: 27.42, 55.06, 57.33, 60.61, 70.59, 94.05, 95.51, 97.52, 105.96, 110.69, 110.77, 111.01, 111.71, 114.17, 117.03, 127.05, 127.17, 128.24, 128.81, 129.43, 131.17, 136.85, 137.14, 138.81, 139.36, 150.43, 157.23, 158.55, 169.34, 175.38

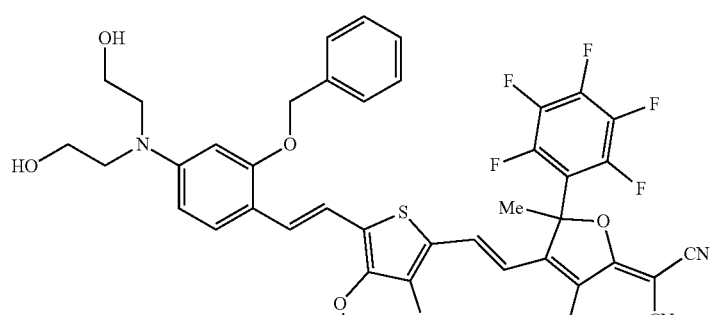

[EO-6]

¹H-NMR (600 MHz, CDCl₃) δ ppm: 2.15 (3H, s), 2.37 (2H, s), 3.58 (4H, t, J = 5.2 Hz), 3.80 (4H, t, J = 5.2 Hz), 4.26-4.27 (2H, m), 4.36-4.37 (2H, m), 5.17 (2H, s), 6.24 (1H, s), 6.34 (1H, d, J = 9.0 Hz), 6.41 (1H, bd), 7.12 (1H, d, J = 15.8 Hz), 7.33-7.45 (7H, m), 7.48 (1H, d, J = 15.8 Hz)
¹³C-NMR (150 MHz, CDCl₃) δ ppm: 27.69, 45.08, 54.86, 60.69, 64.58, 66.05, 70.89, 93.64, 98.02, 106.35, 111.14, 111.47, 112.23, 113.56, 114.37, 115.01, 127.20, 128.19, 128.78, 129.50, 130.73, 135.00, 137.03, 138.78, 150.83, 158.88, 169.25, 175.76

TABLE 5

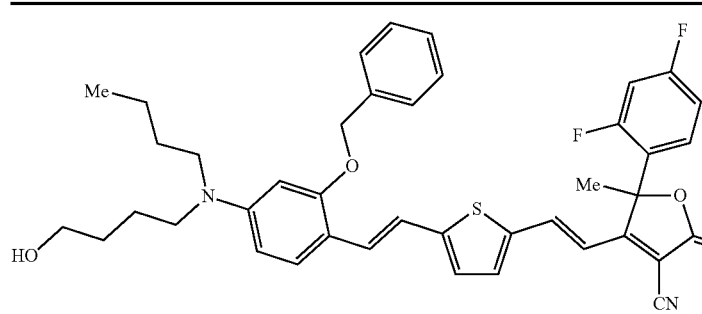

[EO-7]

¹H-NMR (600 MHz, CDCl₃) δ ppm: 0.93 (3H, t, J = 7.6 Hz), 1.27-1.33 (2H, m), 1.47-1.63 (6H, m), 2.11 (3H, s), 3.25 (2H, t, J = 7.6 Hz), 3.29 (2H, t, J = 7.6 Hz), 3.65 (2H, bs), 5.20 (2H, s), 6.11 (1H, d, J = 2.0 Hz), 6.27 (1H, dd, J = 2.7 Hz, 8.9 Hz), 6.52 (1H, d, J = 15.1 Hz), 6.88 (1H, d, J = 4.1 Hz), 6.88-6.92 (1H, m), 7.02-7.05 (1H, m), 7.10 (1H, m), 7.14 (1H, d, J = 15.8 Hz), 7.14 (1H, d, J = 4.1 Hz), 7.27 (1H, d, J = 15.8 Hz), 7.34-7.47 (7H, m), 7.50-7.54 (1H, m)
¹³C-NMR (150 MHz, CDCl₃) δ ppm: 13.96, 20.27, 23.80, 25.63, 29.48, 29.99, 50.92, 50.99, 56.09, 62.54, 70.37, 94.88, 96.27, 105.26, 106.11, 111.07, 111.21, 111.58, 112.10, 112.24, 112.87, 116.10, 119.73, 126.57, 126.89, 128.02, 128.72, 128.84, 129.43, 131.12, 136.92, 137.07, 138.14, 139.31, 150.37, 156.91, 158.76, 171.23, 176.08

TABLE 5-continued

| Compound | NMR Data |
|---|---|
| [EO-8] | ¹H-NMR (600 MHz, CDCl₃) δ ppm: 0.93 (3H, t, J = 7.6 Hz), 1.27-1.33 (2H, m), 1.47-1.63 (6H, m), 2.11 (3H, s), 3.25 (2H, t, J = 7.6 Hz), 3.29 (2H, t, J = 7.6 Hz), 3.65 (2H, q, J = 6.2 Hz), 5.20 (2H, s), 6.10 (1H, d, J = 2.8 Hz), 6.27 (1H, dd, J = 2.1 Hz, 8.9 Hz), 6.51 (1H, d, J = 15.8 Hz), 6.87 (1H, d, J = 4.2 Hz), 7.08-7.11 (2H, m), 7.17 (1H, d, J = 15.1 Hz), 7.31-7.48 (9H, m), 7.64 ( d, J = 8.9 Hz) <br> ¹³C-NMR (150 MHz, CDCl₃) δ ppm: 13.95, 20.27, 23.80, 27.63, 29.48, 29.99, 50.92, 50.99, 56.41, 62.54, 70.37, 95.82, 96.27, 105.28, 111.12, 111.28, 111.62, 112.2, 112.89, 116.09, 126.60, 126.89, 127.71, 128.03, 128.72, 129.47, 129.60, 131.25, 132.44, 136.01, 136.93, 137.05, 137.69, 138.29, 139.09, 150.41 157.17, 158.79, 171.42, 176.65 |
| [EO-9] | ¹H-NMR (600 MHz, CDCl₃) δ ppm: 0.93 (3H, t, J = 7.6 Hz), 1.27-1.34 (2H, m), 1.47-1.64 (6H, m), 2.09 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.7 Hz), 6.28 (1H, dd, J = 2.7 Hz, 8.9 Hz), 6.49 (1H, d, J = 15.1 Hz), 6.90 (1H, d, J = 4.1 Hz), 7.12 (1H, d, J = 15.8 Hz), 7.17 (1H, dd, J = 2.7 Hz), 7.20 (1H, d, J = 4.2 Hz), 7.32-7.46 (8H, m), 7.48 (1H, d, J = 15.8 Hz), 7.54 (1H, d, J = 9.0 Hz) <br> ¹³C-NMR (150 MHz, CDCl₃) δ ppm: 13.96, 20.28, 23.81, 24.63, 29.48, 29.98, 50.94, 51.00, 56.17, 62.53, 70.37, 96.22, 96.72, 105.31, 110.05, 111.05, 111.43. 112.07, 112.86, 116.08, 125.47, 126.83, 126.90, 128.05, 128.20, 128.74, 129.60, 131.55, 131.62, 134.01, 135.14, 136.13, 136.96, 137.02, 138.85, 140.44, 150.52, 157.71, 158.87, 170.50, 175.54 |
| [EO-10] | ¹H-NMR (600 MHz, CDCl₃) δ ppm: 0.93 (3H, t, J = 7.6 Hz), 1.29-1.34 (2H, m), 1.48-1.64 (6H, m), 2.09 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.0 Hz), 6.27 (1H, dd, J = 2.0 Hz, 8.9 Hz), 6.52 (1H, d, J = 15.1 Hz), 6.89 (1H, d, J = 4.1 Hz), 7.11 (1H, d, J = 15.8 Hz), 7.17 (1H, d, J = 4.1 Hz), 7.23 (2H, d, J = 8.9 Hz), 7.31 (1H, d, J = 15.2 Hz), 7.34-7.48 (7H, m), 7.60 (2H, d, J = 8.2 Hz) <br> ¹³C-NMR (150 MHz, CDCl₃) δ ppm: 13.96, 20.28, 23.80, 24.66, 29.48, 29.99, 50.93, 51.00, 55.97, 62.54, 70.37, 96.26, 97.55, 105.28, 111.06, 111.25, 111.54, 111.16, 112.88, 116.10, 125.00, 126.70, 126.89, 127.74, 128.04, 128.73, 129.49, 131.32, 132.75, 135.05, 136.96, 137.06, 138.48, 140.41, 150.43, 157.23, 158.81, 171.32, 175.75 |

TABLE 6

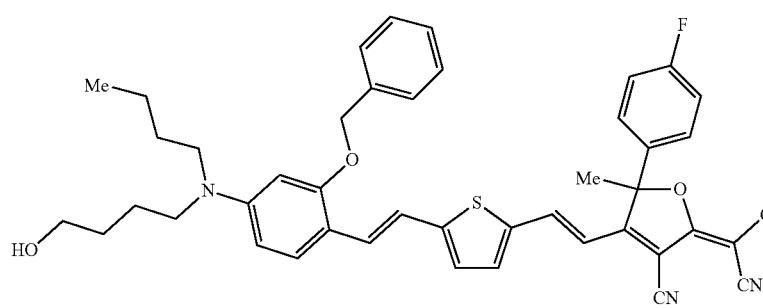

[EO-11]

¹H-NMR (600 MHz, CDCl₃) δ ppm: 0.93 (3H, t, J = 7.6 Hz), 1.27-1.34 (2H, m), 1.47-1.63 (6H, m), 2.11 (3H, s), 3.25 (2H, t, J = 7.6 Hz), 3.29 (2H, t, J = 7.6 Hz), 3.65 (2H, q, J = 6.2 Hz), 5.20 (2H, s), 6.11 (1H, d, J = 2.7 Hz), 6.27 (1H, dd, J = 2.0 Hz, 9.0 Hz), 6.53 (1H, d, J = 15.8 Hz), 6.88 (1H, d, J = 4.1 Hz), 7.10 (1H, d, J = 15.8 Hz), 7.14-7.17 (3H, m), 7.28 (1H, d, J = 15.8 Hz), 7.34-7.44 (8H, m), 7.46 (1H, d, J = 15.8 Hz)
¹³C-NMR (150 MHz, CDCl₃) δ ppm: 13.96, 20.28, 23.80, 24.88, 29.48, 29.99, 50.93, 50.99, 55.90, 62.54, 70.37, 95.70, 96.27, 97.61, 105.28, 111.07, 111.37, 111.58, 112.23, 112.87, 116.09, 116.57, 116.73, 126.66, 126.89, 128.02, 128.27, 128.33, 128.72, 131.22, 131.96, 136.96, 137.06, 140.41, 150.41, 157.93, 171.68, 175.75

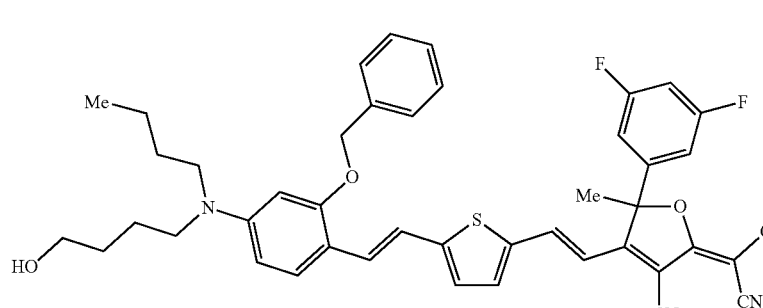

[EO-12]

¹H-NMR (600 MHz, CDCl₃) δ ppm: 0.93 (3H, t, J = 7.6 Hz), 1.28-1.34 (2H, m), 1.48-1.64 (6H, m), 2.08 (3H, s), 3.26 (2H, t, J = 7.6 Hz), 3.30 (2H, t, J = 7.6 Hz), 3.65 (2H, q, J = 5.8 Hz), 5.21 (2H, s), 6.11 (1H, d, J = 2.1 Hz), 6.28 (1H, dd, J = 2.0 Hz, 9.0 Hz), 6.43 (1H, d, J = 15.2 Hz), 6.88-6.95 (4H, m), 7.12 (1H, d, J = 15.8 Hz), 7.21 (1H, d, J = 4.2 Hz), 7.34-7.45 (7H, m), 7.46 (1H, d, J = 15.8 Hz)
¹³C-NMR (150 MHz, CDCl₃) δ ppm: 13.96, 20.28, 23.82, 24.55, 29.50, 29.99, 50.95, 51.01, 56.29, 62.54, 70.38, 95.25, 96.24, 96.49, 105.33, 106.15, 109.62, 110.88, 111.02, 111.36, 112.04, 112.88, 116.09, 126.85, 126.91, 128.06, 128.74, 129.63, 131.67, 137.00, 137.03, 138.88, 139.82, 140.44, 150.54, 157.79, 158.90, 163.44, 170.30, 175.55

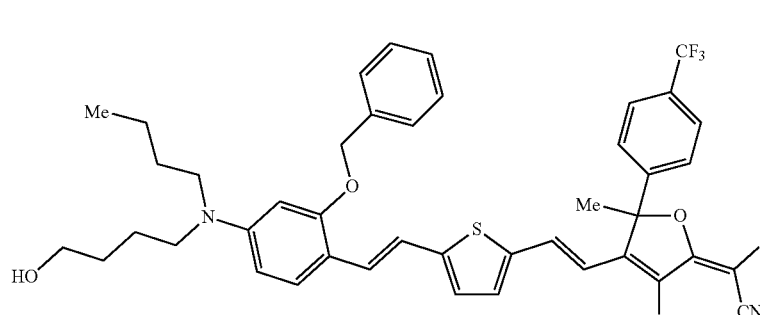

[EO-13]

¹H-NMR (600 MHz, CDCl₃) δ ppm: 0.93 (3H, t, J = 7.6 Hz), 1.28-1.34 (2H, m), 1.48-1.64 (6H, m), 2.14 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.7 Hz), 6.27 (1H, dd, J = 2.7 Hz, 9.0 Hz), 6.51 (1H, d, J = 15.1 Hz), 6.89 (1H, d, J = 4.1 Hz), 7.11 (1H, d, J = 15.8 Hz), 7.18 (1H, d, J = 4.1 Hz), 7.34-7.51 (11H, m), 7.74 (1H, d, J = 8.2 Hz)
¹³C-NMR (150 MHz, CDCl₃) δ ppm: 13.96, 20.28, 23.82, 24.73, 29.49, 29.99, 50.94, 51.01, 56.16, 62.54, 70.38, 96.25, 97.20, 105.32, 111.04, 111.44, 112.07, 112.87, 116.08, 126.58, 126.80, 126.91, 128.04, 128.73, 129.58, 131.55, 136.96, 137.04, 138.75, 139.94, 140.46, 150.52, 157.57, 158.87, 170.84, 175.74

TABLE 6-continued

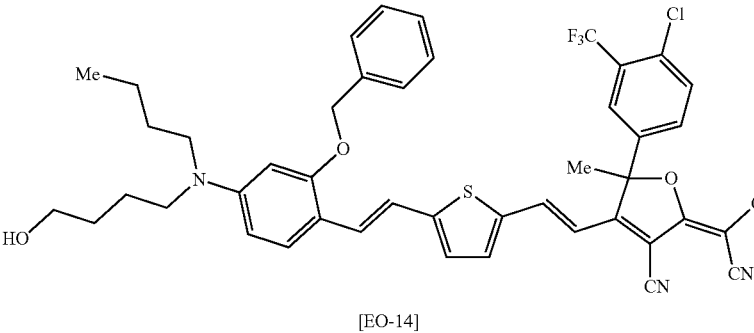

[EO-14]

¹H-NMR (600 MHz, CDCl₃) δ ppm: 0.93 (3H, t, J = 7.6 Hz), 1.27-1.34 (2H, m), 1.47-1.64 (6H, m), 2.13 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.7 Hz), 6.27 (1H, dd, J = 2.1 Hz, 8.9 Hz), 6.48 (1H, d, J = 15.2 Hz), 6.91 (1H, d, J = 4.1 Hz), 7.12 (1H, d, J = 15.8 Hz), 7.21 (1H, d, J = 4.1 Hz), 7.34-7.45 (8H, m), 7.49 (1H, d, J = 15.8 Hz), 7.62 (1H, d, J = 8.2 Hz), 7.71 (1H, d, J = 2.1 Hz)
¹³C-NMR (150 MHz, CDCl₃) δ ppm: 13.96, 20.28, 23.82, 24.78, 29.50, 29.98, 50.95, 51.01, 56.36, 62.54, 70.38, 96.21, 96.58, 105.33, 110.76, 111.05, 111.35, 112.00, 112.88, 116.08, 125.10, 126.91, 128.07, 128.74, 129.69, 130.77, 131.85, 132.88, 134.99, 135.39, 136.93, 137.01, 139.03, 140.44, 150.58, 158.03, 158.94, 170.04, 175.43

TABLE 7

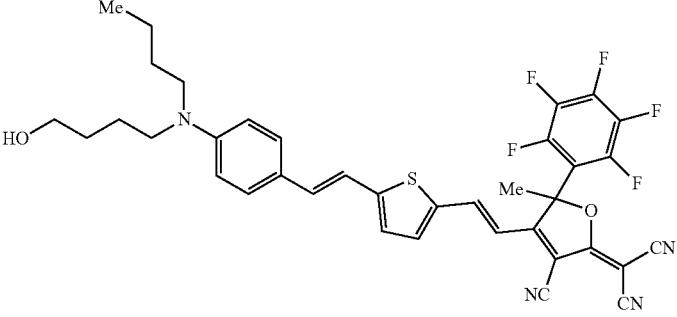

[EO-15]

¹H-NMR (600 MHz, CDCl₃) δ ppm: 0.97 (3H, t, J = 7.2 Hz), 1.33-1.40 (2H, m), 1.58-1.64 (4H, m), 1.68-1.73 (2H, m), 2.20 (3H, s), 3.33 (2H, t, J = 7.6 Hz₂), 3.38 (2H, t, J = 7.6 Hz), 3.70 (2H, q, J = 6.2 Hz), 6.51 (1H, d, J = 15.8 Hz), 6.64 (2H, d, J = 9.0 Hz), 6.96 (1H, d, J = 15.8 Hz), 7.00 (1H, d, J = 4.1 Hz), 7.10 (1H, d, J = 15.8 Hz), 7.30 (1H, d, J = 4.2 Hz), 7.37 (2H, d, J = 9.0 Hz), 7.44 (1H, d, J = 15.1 Hz)
¹³C-NMR (150 MHz, CDCl₃) δ ppm: 13.98, 20.30, 23.83, 27.45, 29.44, 30.07, 50.83, 50.87, 57.40, 62.63, 94.06, 95.55, 110.69, 110.81, 110.99, 111.69, 111.80, 115.28, 122.76, 127.10, 129.32, 135.96, 137.09, 138.80, 139.34, 149.25, 156.39, 169.36, 175.37

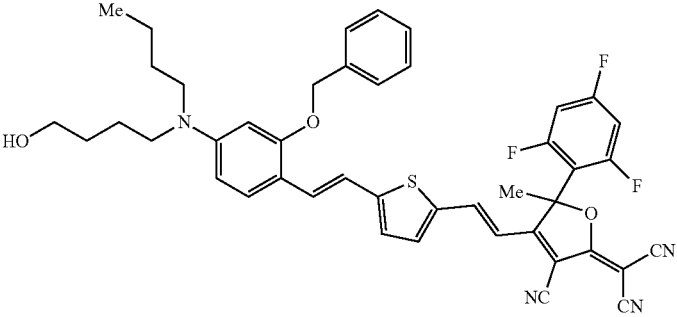

[EO-16]

¹H-NMR (600 MHz, CDCl₃) δ ppm: 0.93 (3H, t, J = 7.6 Hz), 1.27-1.34 (2H, m), 1.48-1.63 (6H, m), 2.16 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.0 Hz), 6.27 (1H, dd, J = 2.0 Hz, 8.9 Hz), 6.54 (1H, d, J = 15.1 Hz), 6.79 (2H, dd, J = 8.3 Hz, 2.7 Hz), 6.90 (1H, d, J = 4.1 Hz), 7.11 (1H, d, J = 15.8 Hz), 7.20 (1H, d, J = 4.1 Hz), 7.33-7.45 (7H, m), 7.47 (1H, d, J = 15.8 Hz)
¹³C-NMR (150 MHz, CDCl₃) δ ppm: 13.96, 20.28, 23.80, 27.64, 29.48, 29.99, 50.93, 50.99, 56.36, 62.54, 70.38, 94.44, 95.39, 96.27, 102.31, 105.28, 110.94, 111.00, 111.48, 112.15, 112.88, 116.08, 126.63, 126.89, 128.03, 128.72, 129.49, 131.31, 136.88, 137.06, 138.36, 139.10, 150.42, 157.21, 158.81, 171.15, 175.89

TABLE 7-continued

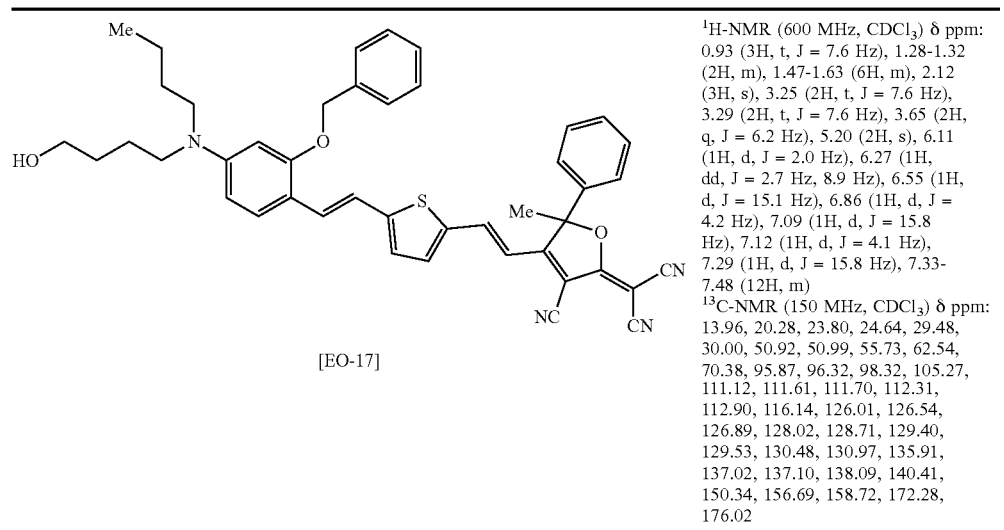

[EO-17]

¹H-NMR (600 MHz, CDCl₃) δ ppm: 0.93 (3H, t, J = 7.6 Hz), 1.28-1.32 (2H, m), 1.47-1.63 (6H, m), 2.12 (3H, s), 3.25 (2H, t, J = 7.6 Hz), 3.29 (2H, t, J = 7.6 Hz), 3.65 (2H, q, J = 6.2 Hz), 5.20 (2H, s), 6.11 (1H, d, J = 2.0 Hz), 6.27 (1H, dd, J = 2.7 Hz, 8.9 Hz), 6.55 (1H, d, J = 15.1 Hz), 6.86 (1H, d, J = 4.2 Hz), 7.09 (1H, d, J = 15.8 Hz), 7.12 (1H, d, J = 4.1 Hz), 7.29 (1H, d, J = 15.8 Hz), 7.33-7.48 (12H, m)
¹³C-NMR (150 MHz, CDCl₃) δ ppm: 13.96, 20.28, 23.80, 24.64, 29.48, 30.00, 50.92, 50.99, 55.73, 62.54, 70.38, 95.87, 96.32, 98.32, 105.27, 111.12, 111.61, 111.70, 112.31, 112.90, 116.14, 126.01, 126.54, 126.89, 128.02, 128.71, 129.40, 129.53, 130.48, 130.97, 135.91, 137.02, 137.10, 138.09, 140.41, 150.34, 156.69, 158.72, 172.28, 176.02

EO Molecule Synthesis Example 18

2-[5-[1,1'-(4-Biphenyl)]-4-[(E)-2-[5-[(E)-2-(benzyloxy)-4-[butyl(4-hydroxybutyl)amino]styryl]thiophen-2-yl]vinyl]-3-cyano-5-methylfuran-2 (5H)-ylidene]malononitrile (EO-18)

(1) 3-[1,1'-(4-Biphenyl)]-3-hydroxy-2-butanone [31]

[Chem. 16]

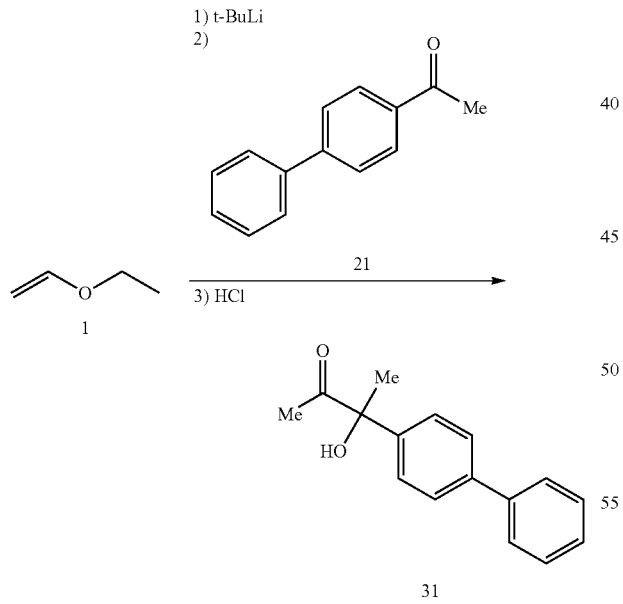

13.7 g (0.19 mol) of ethyl vinyl ether [1] was dissolved in 85 mL of THF under an argon atmosphere. To this, 100 mL (0.19 mol) of tert-butyllithium (1.9 mol solution in pentane) was added dropwise with cooling in a dry ice/acetone bath. The resulting yellow slurry was stirred for 30 minutes, the cooling bath was removed, and the reaction mixture was heated to 0° C. Immediately thereafter, this was cooled again to −73° C., and 135 mL of a solution of 25.18 g (0.128 mol) of 4-acetylbiphenyl [21] in THF was added dropwise. After 1.5 hours of stirring, the reaction mixture was slowly heated to room temperature and stirred at room temperature overnight. A mixed solution of methanol/water/concentrated hydrochloric acid (6/2/2) was added dropwise under ice cooling to render the mixture faintly acidic, followed by stirring at room temperature for 2.5 hours. The reaction mixture was subjected to vacuum concentration and subsequent ether extraction. The extract was washed successively with a saturated aqueous sodium chloride solution, a saturated aqueous sodium hydrogen carbonate solution, and a saturated aqueous sodium chloride solution. The washed extract was dehydrated over anhydrous magnesium sulfate and then concentrated. The residue was crystallized from ethyl acetate/hexane (1/10) to give 17.05 g of the desired compound [31] as colorless crystals (yield: 55.3%, mp: 92 to 95° C.).

Compound 31

¹H-NMR (600 MHz, CDCl₃) δ ppm: 1.83 (3H, s), 2.14 (3H, s), 4.57 (1H, s), 7.36 (1H, t, J=7.6 Hz), 7.45 (2H, t, J=7.6 Hz), 7.51 (2H, d, J=8.2 Hz), 7.58-7.62 (4H, m).
¹³C-NMR (150 MHz, CDCl₃) δ ppm: 23.53, 24.09, 79.77, 126.47, 127.10, 127.41, 127.53, 128.83, 140.39, 140.98, 209.55.

(2) 2-[5-[1,1'-(4-Biphenyl)]-3-cyano-4,5-dimethylfuran-2 (5H)-ylidene]malononitrile [41]

[Chem. 17]

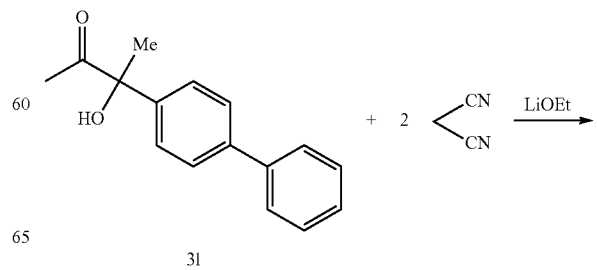

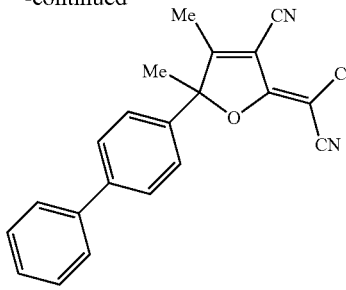

41

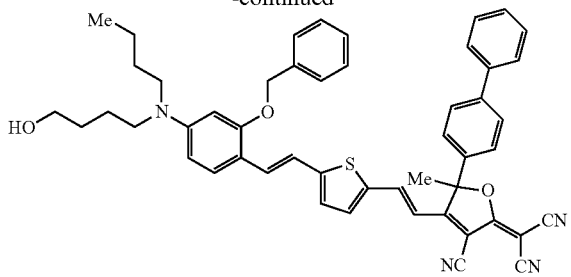

(EO-18)

10.6 g (44.1 mmol) of 3-[1,1'-(4-biphenyl)]-3-hydroxy-2-butanone [31] and 6.36 g (96.3 mmol) of malononitrile were dissolved in 45 mL of ethanol. To this, 2.4 mL of lithium ethoxide (1 mol solution in ethanol) was added, and the mixture was stirred in an oil bath at 70° C. for 4 hours. The ethanol was evaporated off in vacuo, and the residue was purified by silica gel column chromatography (chloroform/methanol=30/1). The purified product was recrystallized from ethyl acetate/hexane to give 5.76 g of the desired compound [41] as white crystals (yield: 38.7%, mp: 205 to 206° C.).

Compound 41

$^1$H-NMR (600 MHz, CDCl$_3$) δ ppm: 2.06 (3H, s), 2.28 (3H, s), 7.28 (2H, d, J=9.0 Hz), 7.40-7.43 (1H, m), 7.47-7.49 (2H, m), 7.57-7.59 (2H, m), 7.68 (2H, d, J=9.0 Hz).

$^{13}$C-NMR (150 MHz, CDCl$_3$) δ ppm: 14.53, 22.49, 59.34, 101.32, 104.93, 108.91, 110.15, 110.74, 125.54, 127.15, 128.28, 128.33, 129.06, 132.60, 139.36, 143.61, 175.47, 181.76.

(3) 2-[5-[1,1'-(4-Biphenyl)]-4-[(E)-2-[5-[(E)-2-(benzyloxy)-4-[butyl(4-hydroxybutyl)amino]styryl]thiophen-2-yl]vinyl]-3-cyano-5-methylfuran-2 (5H)-ylidene]malononitrile [EO-18]

[Chem. 18]

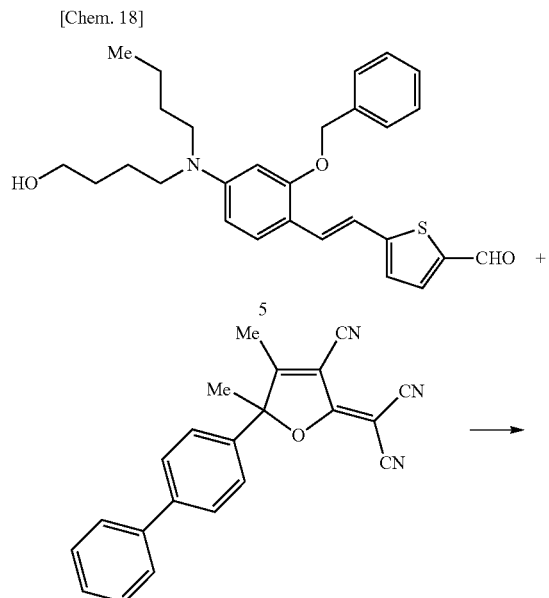

2.5 g (5.39 mmol) of 5-[(E)-2-[2-benzyloxy-4-[butyl(4-hydroxybutyl)amino]phenyl]vinyl]thiophene-2-carbaldehyde [5] and 2.0 g (5.93 mmol) of 2-[5-[1,1'-(4-biphenyl)]-3-cyano-4,5-dimethylfuran-2 (5H)-ylidene]malononitrile [41] were dissolved in 45 mL of ethanol and 20 mL of THF with heating at 50° C. The solution was stirred at the same temperature for 3.5 hours and then concentrated to dryness. The residue was crystallized from methanol. The crystals were collected by filtration and purified by silica gel column chromatography (chloroform/methanol=20/1). The purified product was crystallized from methanol, and the crystals were collected by filtration to give 2.77 g of the desired compound (EO-18) as dark brown crystals (yield: 65.5%, mp: 161 to 163° C.).

EO-18

$^1$H-NMR (600 MHz, CDCl$_3$) δ ppm: 0.93 (6H, t, J=7.6 Hz), 1.26-1.33 (2H, m), 1.47-1.63 (6H, m), 2.15 (3H, s), 3.24 (2H, t, J=7.6 Hz), 3.29 (2H, t, J=6.2 Hz), 3.64 (2H, t, J=6.2 Hz), 5.19 (2H, s), 6.10 (1H, d, J=2.1 Hz), 6.27 (1H, dd, J=2.8 Hz, 9.0 Hz), 6.58 (1H, d, J=15.8 Hz), 6.86 (1H, d, J=4.1 Hz), 7.09 (1H, d, J=15.8 Hz), 7.15 (1H, d, J=4.1 Hz), 7.31-7.48 (13H, m), 7.59 (2H, d, J=7.6 Hz), 7.67 (2H, d, J=8.3 Hz).

$^{13}$C-NMR (150 MHz, CDCl$_3$) δ ppm: 13.96, 20.28, 23.81, 24.71, 29.48, 30.01, 50.93, 50.99, 55.75, 62.54, 70.38, 95.85, 96.32, 98.26, 105.28, 111.16, 111.63, 111.72, 112.33, 112.91, 116.15, 126.52, 126.58, 126.89, 127.18, 128.02, 128.12, 128.71, 128.98, 129.41, 131.01, 134.66, 137.04, 137.09, 138.18, 139.58, 140.46, 143.34, 150.36, 156.76, 158.74, 172.13, 175.99.

EO Molecule Synthesis Examples 19 to 23: (EO-19 to EO-23)

EO molecules (EO-19 to EO-23) were synthesized in the same manner as in EO Molecule Synthesis Example 18 (1) to (3). The NMR measurement results of the obtained EO molecules (EO-19 to EO-23) are shown in Table 8.

TABLE 8

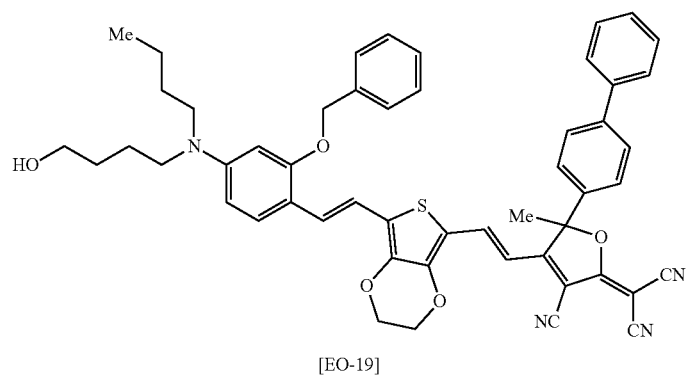 [SMILES: CCCCN(CCCCO)c1ccc(/C=C/c2sc(/C=C/C3=C(C#N)C(=C(C#N)C#N)OC3(C)c3ccc(-c4ccccc4)cc3)c3c2OCCO3)c(OCc2ccccc2)c1]

[EO-19]

¹H-NMR (600 MHz, CDCl₃) δ ppm: 0.93 (3H, t, J = 7.60), 1.28-1.33 (3H, m), 1.47-1.63 (6H, m), 2.13 (3H, s), 3.25 (2H, t, J = 7.6 Hz), 3.29 (2H, t, J = 7.6 Hz), 3.65 (2H, q, J = 6.2 Hz), 4.23 (2H, bs), 4.31 (2H, bs), 5.20 (2H, s), 6.09 (1H, d, J = 2.1 Hz), 6.26 (1H, dd, J = 2.1 Hz, 8.9 Hz), 6.50 (1H, br), 7.08 (1H, d, J = 15.9 Hz), 7.30-7.48 (12H, m), 7.60 (2H, d, J = 7.6 Hz), 7.66 (2H, d, J = 8.2 Hz)
¹³C-NMR (150 MHz, CDCl₃) δ ppm: 13.95, 20.27, 23.81, 24.94, 29.49, 29.99, 50.92, 50.99, 51.95, 62.54, 64.38, 65.75, 70.31, 96.21, 97.62, 105.33, 111.80, 112.33, 112.99, 113.27, 126.47, 126.88, 127.16, 127.90, 127.95, 128.01, 128.65, 128.95, 129.41, 134.67, 135.44, 137.08, 139.78, 142.92, 150.41, 158.82, 171.80, 176.47

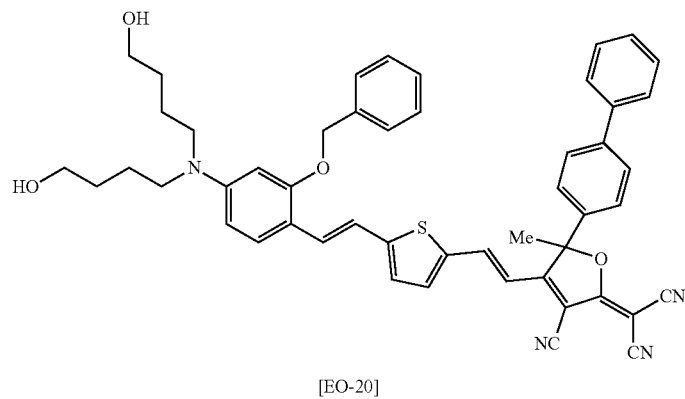 [SMILES: CC1(c2ccc(-c3ccccc3)cc2)OC(=C(C#N)C#N)C(C#N)=C1/C=C/c1ccc(/C=C/c2ccc(N(CCCCO)CCCCO)cc2OCc2ccccc2)s1]

[EO-20]

¹H-NMR (600 MHz, CDCl₃) δ ppm: 1.32 (2H, t, J = 4.5 Hz), 1.52-1.64 (8H, m), 2.15 (3H, s), 3.30 (4H, t, J = 7.1 Hz), 3.65 (4H, q, J = 6.0 Hz), 5.21 (2H, s), 6.12 (1H, d, J = 2.7 Hz), 6.28 (1H, dd, J = 2.7 Hz, 8.9 Hz), 6.59 (1H, d, J = 15.1 Hz), 6.87 (1H, d, J = 4.2 Hz), 7.10 (1H, d, J = 15.8 Hz), 7.15 (1H, d, J = 4.2 Hz), 7.32-7.48 (13H, m), 7.60 (2H, d, J = 7.6 Hz), 7.68 (2H, d, J = 8.2 Hz)
¹³C-NMR (150 MHz, CDCl₃) δ ppm: 23.79, 24.71, 29.94, 50.95, 55.81, 62.50, 70.35, 95.96, 96.45, 98.26, 105.32, 111.13, 111.70, 112.30, 113.07, 116.30, 126.52, 126.62, 126.87, 127.18, 127.98, 128.12, 128.71, 128.98, 129.40, 130.88, 134.60, 137.08, 137.12, 138.15, 139.57, 140.45, 143.34, 150.22, 156.60, 158.69, 172.15, 175.98

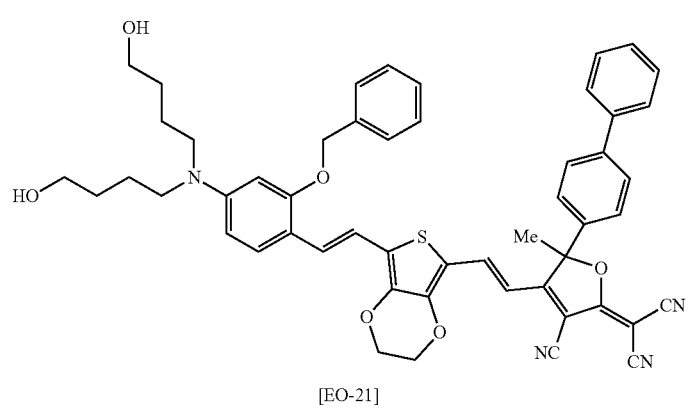 [SMILES: CC1(c2ccc(-c3ccccc3)cc2)OC(=C(C#N)C#N)C(C#N)=C1/C=C/c1sc(/C=C/c2ccc(N(CCCCO)CCCCO)cc2OCc2ccccc2)c2c1OCCO2]

[EO-21]

¹H-NMR (600 MHz, CDCl₃) δ ppm: 1.35 (2H, s), 1.51-1.64 (8H, m), 2.12 (3H, s), 3.30 (4H, t, J = 7.6 Hz), 3.64 (4H, d, J = 6.2 Hz), 4.24 (2H, bs), 4.30 (2H, bs), 5.19 (2H, s), 6.12 (1H, d, J = 2.0 Hz), 6.27 (1H, dd, J = 2.1 Hz, 8.9 Hz), 6.49 (1H, br), 7.08 (1H, d, J = 15.8 Hz), 7.30-7.48 (13H, m), 7.60 (2H, d, J = 9.6 Hz), 7.66 (2H, d, J = 8.9 Hz)
¹³C-NMR (150 MHz, CDCl₃) δ ppm: 23.83, 24.94, 29.95, 50.97, 53.85, 62.50, 64.39, 65.90, 70.31, 96.37, 97.66, 105.42, 111.80, 112.37, 113.00, 113.44, 125.47, 126.48, 126.89, 127.17, 127.98, 128.65, 128.97, 129.41, 134.55, 135.42, 137.14, 139.77, 142.94, 150.34, 158.81, 160.13, 171.84, 176.49

TABLE 8-continued

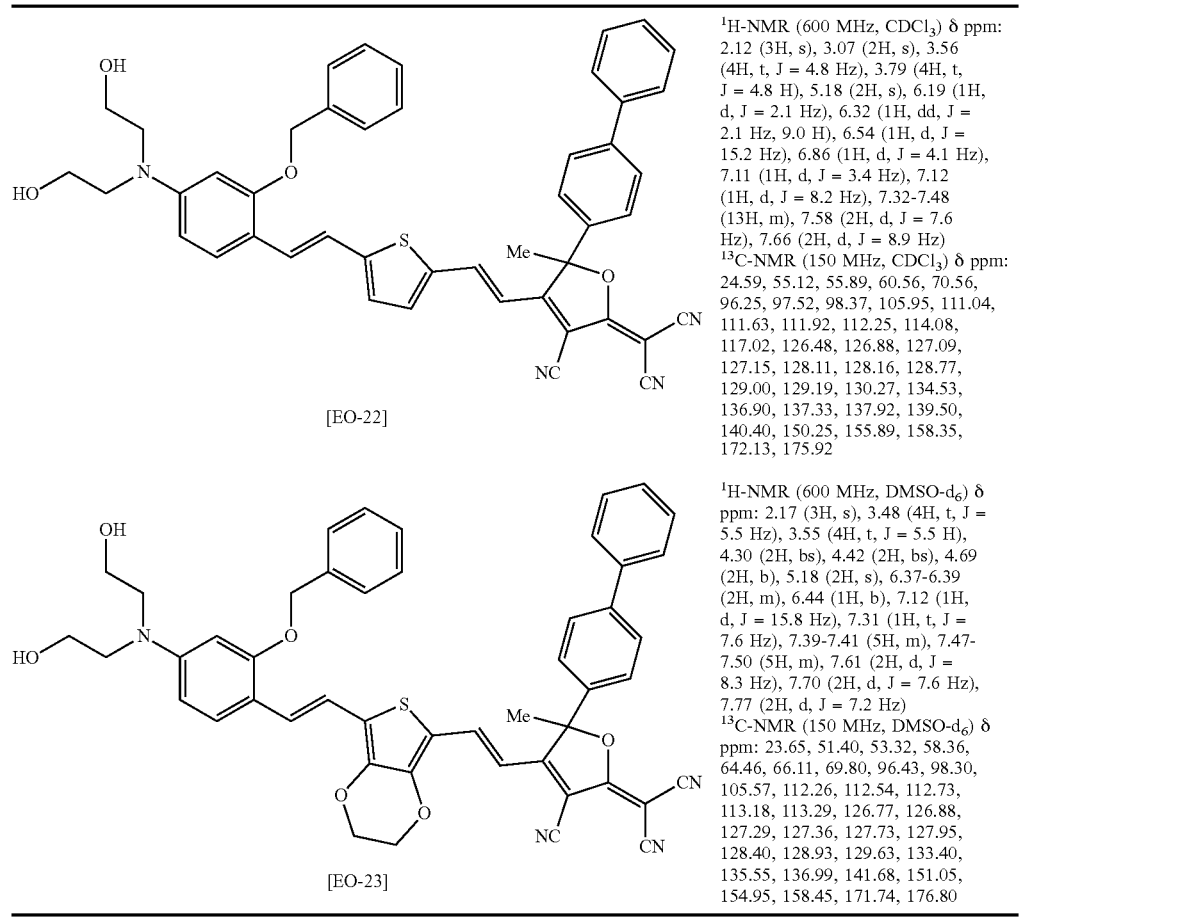

[EO-22]

$^{1}$H-NMR (600 MHz, CDCl$_{3}$) δ ppm: 2.12 (3H, s), 3.07 (2H, s), 3.56 (4H, t, J = 4.8 Hz), 3.79 (4H, t, J = 4.8 H), 5.18 (2H, s), 6.19 (1H, d, J = 2.1 Hz), 6.32 (1H, dd, J = 2.1 Hz, 9.0 H), 6.54 (1H, d, J = 15.2 Hz), 6.86 (1H, d, J = 4.1 Hz), 7.11 (1H, d, J = 3.4 Hz), 7.12 (1H, d, J = 8.2 Hz), 7.32-7.48 (13H, m), 7.58 (2H, d, J = 7.6 Hz), 7.66 (2H, d, J = 8.9 Hz)
$^{13}$C-NMR (150 MHz, CDCl$_{3}$) δ ppm: 24.59, 55.12, 55.89, 60.56, 70.56, 96.25, 97.52, 98.37, 105.95, 111.04, 111.63, 111.92, 112.25, 114.08, 117.02, 126.48, 126.88, 127.09, 127.15, 128.11, 128.16, 128.77, 129.00, 129.19, 130.27, 134.53, 136.90, 137.33, 137.92, 139.50, 140.40, 150.25, 155.89, 158.35, 172.13, 175.92

[EO-23]

$^{1}$H-NMR (600 MHz, DMSO-d$_{6}$) δ ppm: 2.17 (3H, s), 3.48 (4H, t, J = 5.5 Hz), 3.55 (4H, t, J = 5.5 H), 4.30 (2H, bs), 4.42 (2H, bs), 4.69 (2H, b), 5.18 (2H, s), 6.37-6.39 (2H, m), 6.44 (1H, b), 7.12 (1H, d, J = 15.8 Hz), 7.31 (1H, t, J = 7.6 Hz), 7.39-7.41 (5H, m), 7.47-7.50 (5H, m), 7.61 (2H, d, J = 8.3 Hz), 7.70 (2H, d, J = 7.6 Hz), 7.77 (2H, d, J = 7.2 Hz)
$^{13}$C-NMR (150 MHz, DMSO-d$_{6}$) δ ppm: 23.65, 51.40, 53.32, 58.36, 64.46, 66.11, 69.80, 96.43, 98.30, 105.57, 112.26, 112.54, 112.73, 113.18, 113.29, 126.77, 126.88, 127.29, 127.36, 127.73, 127.95, 128.40, 128.93, 129.63, 133.40, 135.55, 136.99, 141.68, 151.05, 154.95, 158.45, 171.74, 176.80

EO Molecule Synthesis Examples 24 to 28: (EO-24 to EO-28)

With reference to EO molecule Synthesis Example 1 (1) to (3), intermediate compounds and the desired EO molecules were synthesized. The NMR measurement results of the intermediate compounds obtained in the same manner as in Synthesis Example 1 (1) are shown in Table 9. The NMR measurement results of the intermediate compounds obtained in the same manner as in Synthesis Example 1 (2) are shown in Table 10. The NMR measurement results of the obtained EO molecules (EO-24 to EO-28) are shown in Tables 11 and 12.

TABLE 9

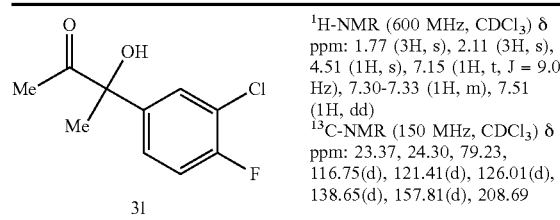

3l $^{1}$H-NMR (600 MHz, CDCl$_{3}$) δ ppm: 1.77 (3H, s), 2.11 (3H, s), 4.51 (1H, s), 7.15 (1H, t, J = 9.0 Hz), 7.30-7.33 (1H, m), 7.51 (1H, dd)
$^{13}$C-NMR (150 MHz, CDCl$_{3}$) δ ppm: 23.37, 24.30, 79.23, 116.75(d), 121.41(d), 126.01(d), 138.65(d), 157.81(d), 208.69

TABLE 9-continued

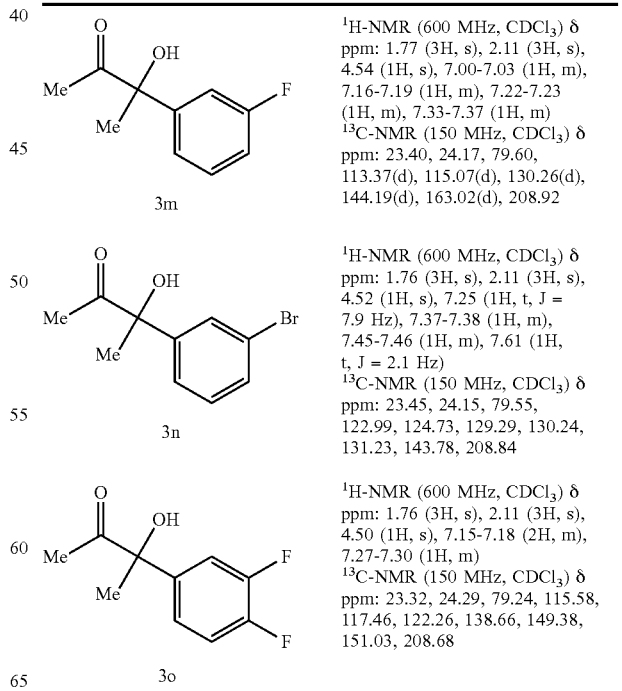

3m $^{1}$H-NMR (600 MHz, CDCl$_{3}$) δ ppm: 1.77 (3H, s), 2.11 (3H, s), 4.54 (1H, s), 7.00-7.03 (1H, m), 7.16-7.19 (1H, m), 7.22-7.23 (1H, m), 7.33-7.37 (1H, m)
$^{13}$C-NMR (150 MHz, CDCl$_{3}$) δ ppm: 23.40, 24.17, 79.60, 113.37(d), 115.07(d), 130.26(d), 144.19(d), 163.02(d), 208.92

3n $^{1}$H-NMR (600 MHz, CDCl$_{3}$) δ ppm: 1.76 (3H, s), 2.11 (3H, s), 4.52 (1H, s), 7.25 (1H, t, J = 7.9 Hz), 7.37-7.38 (1H, m), 7.45-7.46 (1H, m), 7.61 (1H, t, J = 2.1 Hz)
$^{13}$C-NMR (150 MHz, CDCl$_{3}$) δ ppm: 23.45, 24.15, 79.55, 122.99, 124.73, 129.29, 130.24, 131.23, 143.78, 208.84

3o $^{1}$H-NMR (600 MHz, CDCl$_{3}$) δ ppm: 1.76 (3H, s), 2.11 (3H, s), 4.50 (1H, s), 7.15-7.18 (2H, m), 7.27-7.30 (1H, m)
$^{13}$C-NMR (150 MHz, CDCl$_{3}$) δ ppm: 23.32, 24.29, 79.24, 115.58, 117.46, 122.26, 138.66, 149.38, 151.03, 208.68

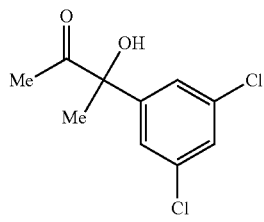
3p
¹H-NMR (600 MHz, CDCl₃) δ ppm: 1.75 (3H, s), 2.13 (3H, s), 4.49 (1H, s), 7.33 (1H, t, J = 2.0 Hz), 7.34 (2H, d, J = 2.0 Hz)
¹³C-NMR (150 MHz, CDCl₃) δ ppm: 23.46, 24.26, 79.43, 124.85, 128.32, 135.45, 144.98, 208.14
TABLE 10
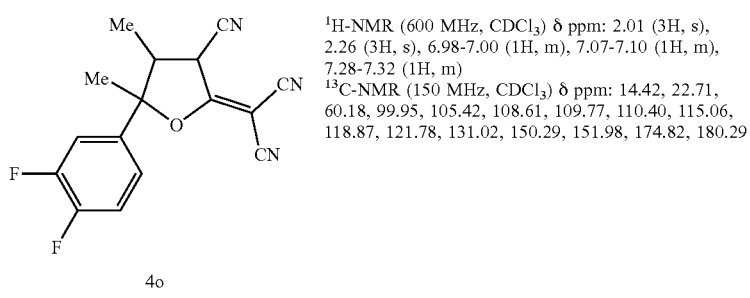
4l
¹H-NMR (600 MHz, DMSO-d₆) δ ppm: 2.05 (3H, s), 2.20 (3H, s), 7.54-7.55 (2H, m), 7.79-7.81 (1H, m)
¹³C-NMR (150 MHz, DMSO-d₆) δ ppm: 14.47, 21.16, 56.60, 100.93, 105.28, 109.85, 111.27, 111.92, 117.46(d), 120.46(d), 127.46(d), 128.93, 131.93, 157.97(d), 177.34, 181.68
4m
¹H-NMR (600 MHz, CDCl₃) δ ppm: 2.02 (3H, s), 2.26 (3H, s), 6.94-6.97 (1H, m), 7.00-7.02 (1H, m), 7.18-7.21 (1H, m), 7.46-7.50 (1H, m)
¹³C-NMR (150 MHz, CDCl₃) δ ppm: 14.48, 22.61, 59.79, 100.49, 105.20, 108.75, 109.95, 110.55, 112.65, 117.69(d), 120.76, 131.56, 136.12(d), 163.12, 175.19, 180.96
4n
¹H-NMR (600 MHz, CDCl₃) δ ppm: 2.01 (3H, s), 2.25 (3H, s), 7.14-7.15 (1H, m), 7.35-7.38 (2H, m), 7.62-7.63 (1H, m)
¹³C-NMR (150 MHz, CDCl₃) δ ppm: 14.49, 22.61, 59.94, 100.36, 105.30, 108.70, 109.90, 110.51, 123.69, 123.90, 128.25, 131.25, 133.78, 136.16, 175.08, 180.76
4o
¹H-NMR (600 MHz, CDCl₃) δ ppm: 2.01 (3H, s), 2.26 (3H, s), 6.98-7.00 (1H, m), 7.07-7.10 (1H, m), 7.28-7.32 (1H, m)
¹³C-NMR (150 MHz, CDCl₃) δ ppm: 14.42, 22.71, 60.18, 99.95, 105.42, 108.61, 109.77, 110.40, 115.06, 118.87, 121.78, 131.02, 150.29, 151.98, 174.82, 180.29

TABLE 10-continued
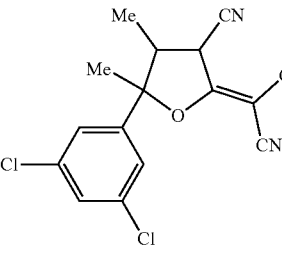
4p
¹H-NMR (600 MHz, CDCl₃) δ ppm: 2.00 (3H, s), 2.27 (3H, s), 7.09 (2H, d, J = 1.4 Hz), 7.49 (1H, d, J = 1.4 Hz)
¹³C-NMR (150 MHz, CDCl₃) δ ppm: 14.49, 22.69, 60.47, 99.67, 105.68, 108.57, 109.72, 110.35, 123.79, 130.83, 136.71, 137.35, 174.75, 179.85
TABLE 11
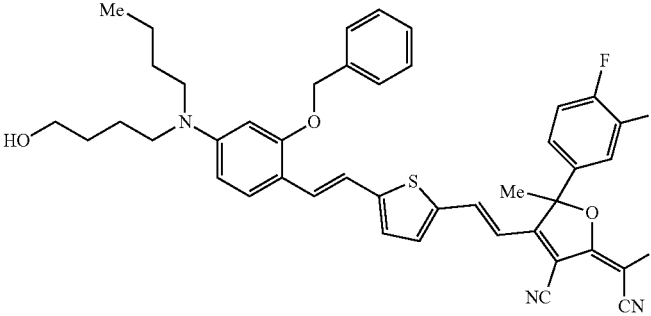
[EO-24]
¹H-NMR (600 MHz, CDCl₃) δ ppm: 0.93 (3H, t, J = 7.6 Hz), 1.27-1.34 (2H, m), 1.47-1.66 (6H, m), 2.10 (3H, s), 3.25 (2H, t, J = 7.6 Hz), 3.30 (2H, t, J = 7.6 Hz), 3.65 (2H, t, J = 5.8 Hz), 5.20 (2H, s), 6.11 (1H, d, J = 2.1 Hz), 6.27 (1H, dd, J = 2.1 Hz, 8.9 Hz), 6.50 (1H, d, J = 15.8 Hz), 6.90 (1H, d, J = 4.1 Hz), 7.11 (1H, d, J = 15.8 Hz), 7.19 (1H, d, J = 4.1 Hz), 7.23-7.45 (10H, m), 7.48 (1H, d, J = 15.8 Hz)
¹³C-NMR (150 MHz, CDCl₃) δ ppm: 13.96, 20.28, 23.82, 24.79, 29.49, 29.99, 50.94, 51.01, 56.21, 62.55, 70.38, 96.25, 96.79, 105.31, 111.04, 111.44, 112.10, 112.88, 116.09, 117.69, 117.84, 122.65, 126.35, 126.40, 126.79, 126.90, 128.05, 128.74, 128.86, 129.59, 131.57, 133.25, 136.96, 137.04, 138.72, 140.44, 150.51, 157.61, 158.87, 170.68, 175.51
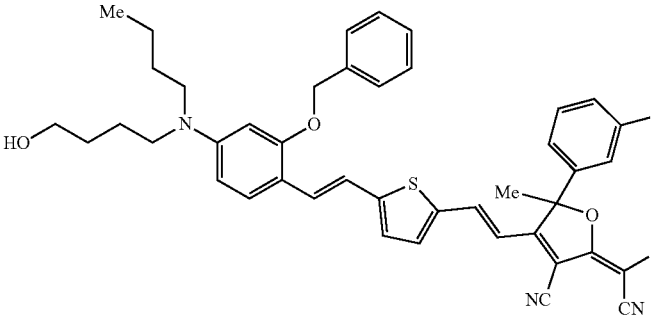
[EO-25]
¹H-NMR (600 MHz, CDCl₃) δ ppm: 0.93 (3H, t, J = 7.6 Hz), 1.27-1.34 (2H, m), 1.48-1.64 (6H, m), 2.10 (3H, s), 3.25 (2H, t, J = 7.6 Hz), 3.29 (2H, t, J = 7.6 Hz), 3.65 (2H, q, J = 6.2 Hz), 5.20 (2H, s), 6.11 (1H, d, J = 2.1 Hz), 6.27 (1H, dd, J = 2.1 Hz, 8.9 Hz), 6.52 (1H, d, J = 15.8 Hz), 6.89 (1H, d, J = 4.1 Hz), 7.07-7.19 (5H, m), 7.32-7.48 (9H, m)
¹³C-NMR (150 MHz, CDCl₃) δ ppm: 13.95, 20.27, 23.81, 24.62, 29.48, 29.99, 50.93, 50.99, 56.01, 62.54, 70.38, 111.05, 111.25, 111.52, 112.17, 112.88, 113.38, 113.53, 116.11, 117.52, 117.66, 121.85, 126.68, 126.90, 128.03, 128.72, 129.51, 131.31, 137.02, 138.47, 140.42, 150.43, 157.23, 158.81, 163.03, 171.29, 175.78

TABLE 11-continued

| Structure | NMR |
|---|---|
| [EO-26] 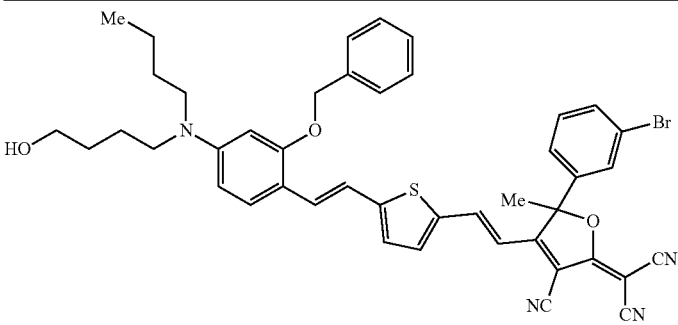 | $^1$H-NMR (600 MHz, CDCl$_3$) δ ppm: 0.93 (3H, t, J = 7.6 Hz), 1.27-1.33 (2H, m), 1.48-1.64 (6H, m), 2.10 (3H, s), 3.25 (2H, t, J = 7.6 Hz), 3.29 (2H, t, J = 7.6 Hz), 3.65 (2H, q, J = 6.2 Hz), 5.20 (2H, s), 6.11 (1H, d, J = 2.1 Hz), 6.27 (1H, dd, J = 2.1 Hz, 8.9 Hz), 6.52 (1H, d, J = 15.1 Hz), 6.89 (1H, d, J = 4.2 Hz), 7.11 (1H, d, J = 15.8 Hz), 7.18 (1H, d, J = 4.2 Hz), 7.25-7.51 (11H, m), 7.60 (1H, d, J = 8.9 Hz) $^{13}$C-NMR (150 MHz, CDCl$_3$) δ ppm: 13.95, 20.27, 23.81, 24.58, 29.48, 29.99, 50.93, 50.99, 56.05, 62.53, 70.38, 95.60, 96.27, 97.25, 105.29, 111.06, 111.21, 111.52, 112.17, 112.88, 116.11, 123.64, 124.79, 126.70, 126.90, 128.03, 128.73, 129.14, 129.54, 131.07, 131.37, 133.66, 137.00, 137.05, 138.15, 138.55, 140.43, 150.45, 157.31, 158.82, 171.16, 175.73 |
| [EO-27] 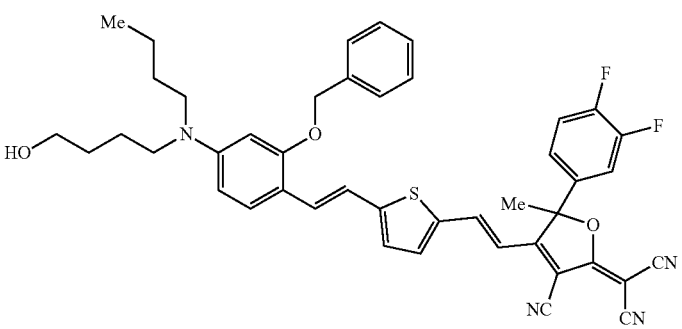 | $^1$H-NMR (600 MHz, CDCl$_3$) δ ppm: 0.93 (3H, t, J = 7.6 Hz), 1.27-1.34 (2H, m), 1.48-1.64 (6H, m), 2.09 (3H, s), 3.25 (2H, t, J = 7.6 Hz), 3.30 (2H, t, J = 7.6 Hz), 3.65 (2H, q, J = 6.2 Hz), 5.20 (2H, s), 6.11 (1H, d, J = 2.1 Hz), 6.27 (1H, dd, J = 2.1 Hz, 8.9 Hz), 6.50 (1H, d, J = 15.1 Hz), 6.90 (1H, d, J = 4.2 Hz), 7.08-7.13 (2H, m), 7.19-7.45 (10H, m), 7.48 (1H, d, J = 15.8 Hz) $^{13}$C-NMR (150 MHz, CDCl$_3$) δ ppm: 13.96, 20.28, 23.82, 24.80, 29.49, 29.99, 50.94, 51.01, 56.19, 62.54, 70.38, 96.25, 96.81, 105.31, 111.04, 111.43, 112.08, 112.88, 115.82, 115.95, 116.09, 118.52, 118.64, 122.81, 126.79, 126.90, 128.05, 128.74, 129.58, 131.56, 133.14, 137.00, 138.71, 140.43, 150.51, 157.59, 158.87, 170.70, 175.53 |

TABLE 12

| Structure | NMR |
|---|---|
| [EO-28] 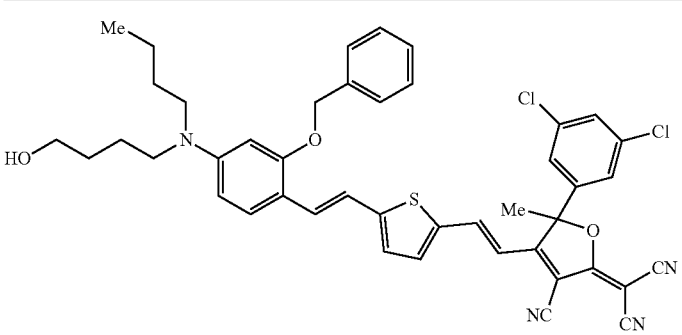 | $^1$H-NMR (600 MHz, CDCl$_3$) δ ppm: 0.93 (3H, t, J = 7.6 Hz), 1.28-1.34 (2H, m), 1.48-1.64 (6H, m), 2.08 (3H, s), 3.25 (2H, t, J = 7.6 Hz), 3.30 (2H, t, J = 7.6 Hz), 3.65 (2H, q, J = 6.2 Hz), 5.21 (2H, s), 6.11 (1H, d, J = 2.0 Hz), 6.27 (1H, dd, J= 2.8 Hz, 8.9 Hz), 6.48 (1H, d, J = 15.8 Hz), 6.91 (1H, d, J = 4.1 Hz), 7.12 (1H, d, J = 15.8 Hz), 7.22-7.23 (3H, m), 7.34-7.47 (8H, m), 7.49 (1H, d, J = 15.8 Hz) $^{13}$C-NMR (150 MHz, CDCl$_3$) δ ppm: 13.96, 20.28, 23.82, 24.52, 29.49, 29.99, 50.94, 51.01, 56.37, 62.54, 70.38, 95.34, 96.24, 96.46, 105.32, 110.85, 111.03, 111.36, 112.05, 112.90, 116.11, 124.75, 126.86, 126.91, 128.06, 128.75, 129.66, 130.74, 131.73, 136.41, 137.00, 137.02, 138.95, 139.32, 140.45, 150.54, 157.89, 158.91, 170.16, 175.49 |

Example 1: Production of Electro-Optic Polymer (EOP-1)

1.74 g of a base polymer (copolymer A-1) was dissolved in 65 mL of tetrahydrofuran (THF). To this, 0.75 g of an EO molecule (EO-1) and 45 µL of dibutyltin dilaurate (DBTDL) were added, and the mixture was stirred in an oil bath at 60° C. for 3 hours. Subsequently, 3 mL of methanol and 20 µL of DBTDL were added, and the mixture was stirred for 45 minutes. The reaction mixture was cooled and then poured into 790 mL of diisopropyl ether (IPE), and the mixture was stirred. The precipitated powder was collected by filtration and washed with 100 mL of a THF/IPE (1/9) mixture and subsequently with IPE. This was dried in vacuo with heating at 70° C. to give 2.17 g of an electro-optic polymer (EOP-1) as a black powder.

Examples 2 to 14: Production of Electro-Optic Polymers (EOP-2 to EOP-14)

Electro-optic polymers (EOP-2 to EOP-14) were obtained as described in Example 1 based on the combinations of base polymers and EO molecules shown in Table 13 and the amounts of the EO molecules shown in Table 13.

The glass transition temperatures (Tgs) of the obtained electro-optic polymers were measured in the same manner as described above for the base polymers. The results are shown in Table 13.

TABLE 13

| Example | Base polymer | EO molecule | | Tg |
|---|---|---|---|---|
| (EO polymer) | (Copolymer) | Type | Content (wt %) | (° C.) |
| 1 | EOP-1 | A-1 | EO-1 | 30 | 128 |
| 2 | EOP-2 | A-2 | EO-2 | 30 | 134 |
| 3 | EOP-3 | A-3 | EO-3 | 30 | 144 |
| 4 | EOP-4 | A-4 | EO-4 | 30 | 149 |
| 5 | EOP-5 | A-5 | EO-7 | 30 | 128 |
| 6 | EOP-6 | A-6 | EO-8 | 30 | 131 |
| 7 | EOP-7 | A-6 | EO-9 | 30 | 129 |
| 8 | EOP-8 | A-7 | EO-10 | 30 | 129 |
| 9 | EOP-9 | A-8 | EO-11 | 30 | 128 |
| 10 | EOP-10 | A-5 | EO-12 | 30 | 128 |
| 11 | EOP-11 | A-9 | EO-13 | 30 | 133 |
| 12 | EOP-12 | A-10 | EO-15 | 30 | 137 |
| 13 | EOP-13 | A-11 | EO-16 | 30 | 129 |
| 14 | EOP-14 | A-12 | EO-17 | 30 | 128 |

The results show that the obtained electro-optic polymers have high glass transition temperatures (Tgs) than those of the corresponding base polymers. This clearly indicates the binding of the base polymers to the EO molecules in the obtained polymers.

Example 15: Production of Electro-Optic Polymer (EOP-15)

1.9 g of a base polymer (copolymer A-1) was dissolved in 70 mL of tetrahydrofuran (THF). To this, 0.818 g of an EO molecule (EO-18) and 50 µL of DBTDL were added, and the mixture was stirred in an oil bath at 60° C. for 3 hours. Subsequently, 3 mL of methanol and 20 µL of DBTDL were added, and the mixture was stirred for 45 minutes. The reaction mixture was cooled and then poured into 850 mL of diisopropyl ether (IPE), and the mixture was stirred. The precipitated powder was collected by filtration and washed with 100 mL of a THF/IPE (1/9) mixture and subsequently with IPE. This was dried in vacuo with heating at 70° C. to give 2.39 g of an electro-optic polymer (EOP-15) as a black powder.

Examples 16 to 19: Production of Electro-Optic Polymers (EOP-16 to EOP-19)

Electro-optic polymers (EOP-16 to EOP-19) were obtained as described in Example 15 based on the combinations of base polymers and EO molecules shown in Table 14 and the amounts of the EO molecules shown in Table 14.

The glass transition temperatures (Tgs) of the obtained electro-optic polymers were measured in the same manner as described above. The results are shown in Table 14.

TABLE 14

| Example | Base polymer | EO molecule | | Tg |
|---|---|---|---|---|
| (EO polymer) | (Copolymer) | Type | Content (wt %) | (° C.) |
| 15 | EOP-15 | A-1 | EO-18 | 30 | 132 |
| 16 | EOP-16 | A-13 | EO-19 | 30 | 134 |
| 17 | EOP-17 | A-14 | EO-20 | 30 | 148 |
| 18 | EOP-18 | A-15 | EO-21 | 30 | 148 |
| 19 | EOP-19 | A-16 | EO-22 | 30 | 156 |

Examples 20 to 24: Production of Electro-Optic Polymers (EOP-20 to EOP-24)

Electro-optic polymers (EOP-20 to EOP-24) were obtained as described in Example 1 based on the combinations of base polymers and EO molecules shown in Table 15 and the amounts of the EO molecules shown in Table 15.

The glass transition temperatures (Tgs) of the obtained electro-optic polymers were measured in the same manner as described above. The results are shown in Table 15.

TABLE 15

| Example | Base polymer | EO molecule | | Tg |
|---|---|---|---|---|
| (EO polymer) | (Copolymer) | Type | Content (wt %) | (° C.) |
| 20 | EOP-20 | A-21 | EO-24 | 30 | 128 |
| 21 | EOP-21 | A-22 | EO-25 | 30 | 127 |
| 22 | EOP-22 | A-23 | EO-26 | 30 | 124 |
| 23 | EOP-23 | A-24 | EO-27 | 30 | 126 |
| 24 | EOP-24 | A-25 | EO-28 | 30 | 129 |

In addition, we confirmed that electro-optic polymers other than the above electro-optic polymers are also producible from the EO molecules synthesized here.

Comparative Examples 1 to 4: Production of Electro-Optic Polymers

Electro-optic polymers were obtained as described in Example 15 based on the combinations of base polymers and EO molecules shown in Table 16 and the amounts of the EO molecules shown in Table 16. The EO molecules shown in Table 16 were synthesized with reference to EO-1.

The glass transition temperatures (Tgs) of the obtained electro-optic polymers were measured in the same manner as described above. The results are shown in Table 16.

TABLE 16

| Comparative Example | Base polymer (Copolymer) | EO molecule Type | Content (wt %) | Tg (° C.) |
|---|---|---|---|---|
| 1 | A-17 | | 35 | 143 |
| 2 | A-18 | 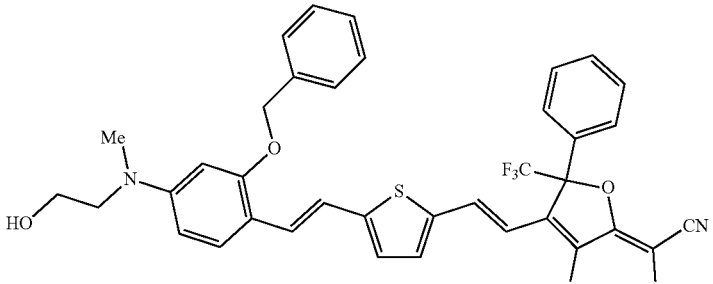 | 30 | 133 |
| 3 | A-19 | 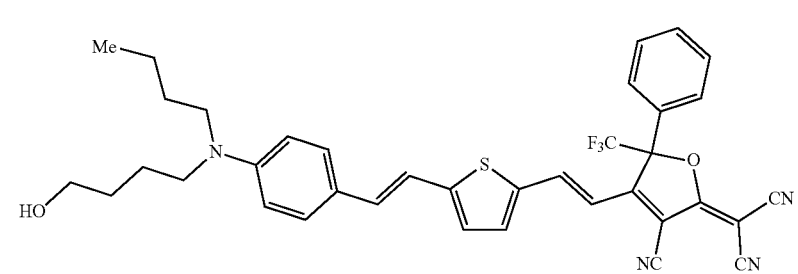 [SMILES: CCCCN(CCCCO)c1ccc(/C=C/c2ccc(/C=C/C3=C(C#N)C(=C(C#N)C#N)OC3(c3ccccc3)C(F)(F)F)s2)cc1] | 30 | 130 |
| 4 | A-20 | 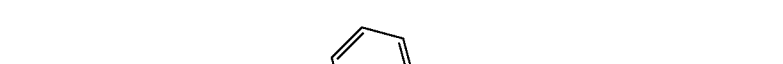 | 30 | 128 |

Test Example 1

Figure 2:
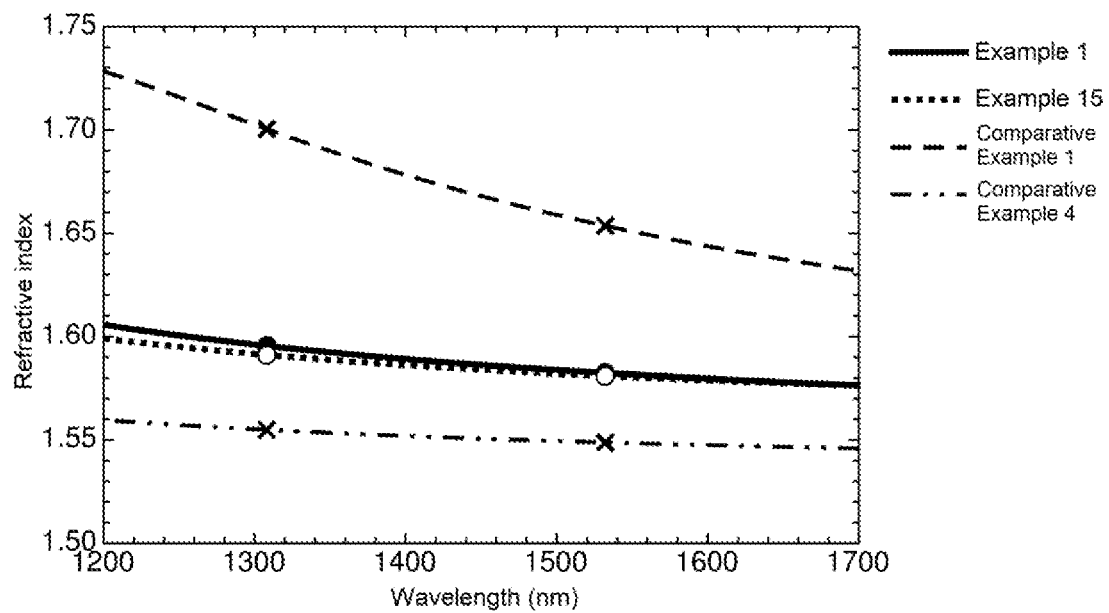
FIG. 2 shows a plot of the refractive index calculated based on the measured values versus wavelength in the entire wavelength range for optical communications.
Figure 3:
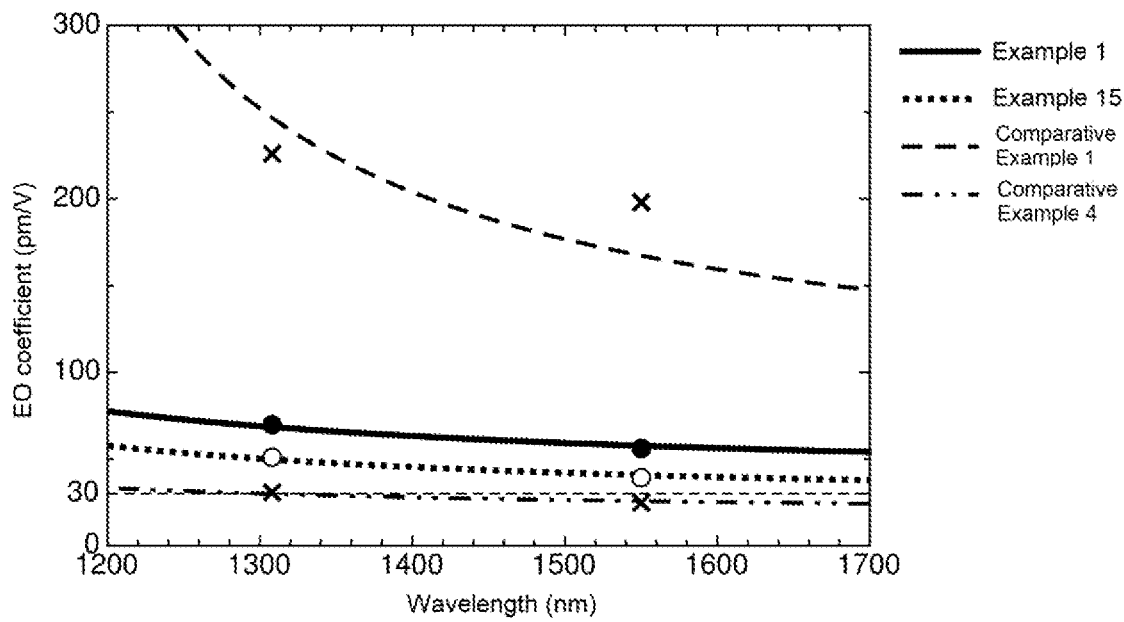
FIG. 3 shows a plot of the EO coefficient calculated based on the measured values versus wavelength in the entire wavelength range for optical communications.
Figure 4:
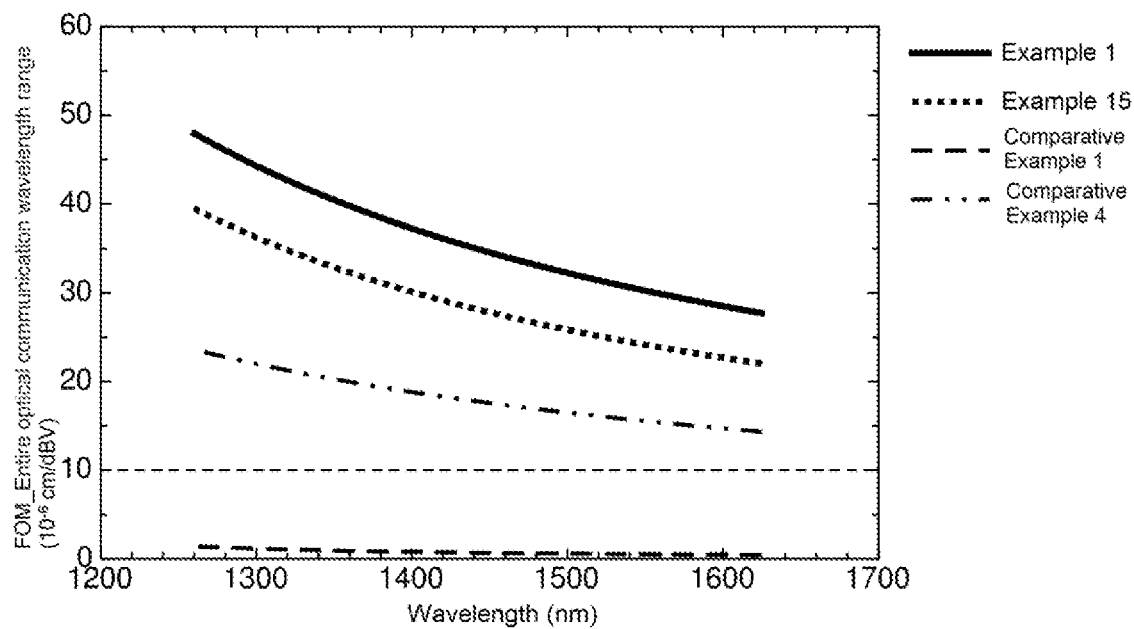
FIG. 4 shows a plot of the calculated figure of merit (FOM) versus wavelength in the entire wavelength range for optical communications.
Figure 5:
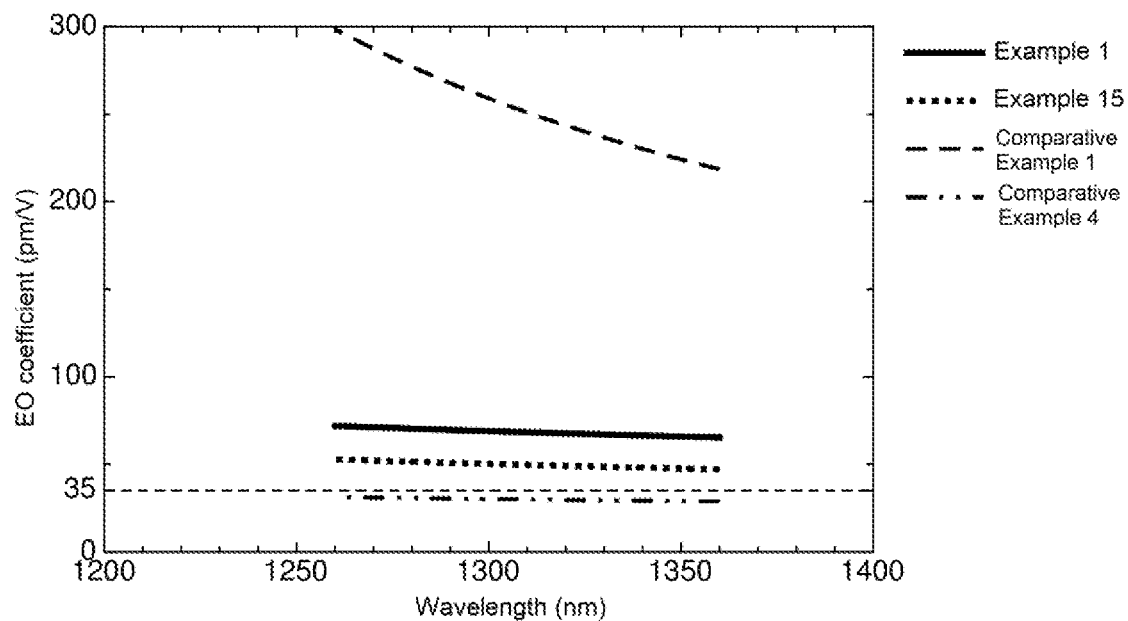
FIG. 5 shows a plot of the EO coefficient calculated based on the measured values versus wavelength in the O-band.
Figure 6:
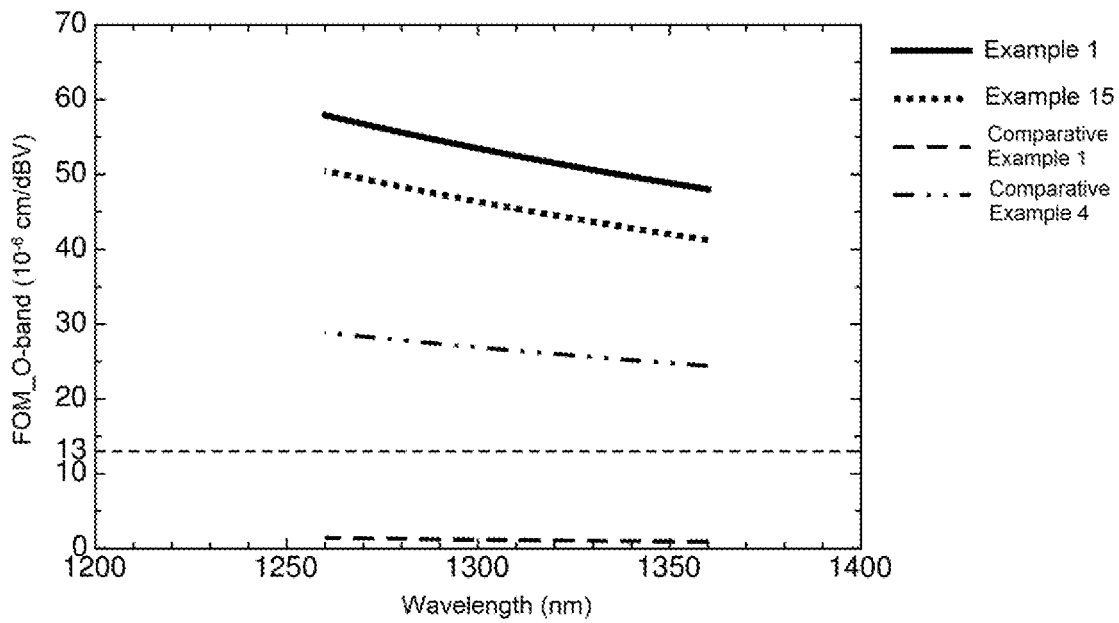
FIG. 6 shows a plot of the calculated FOM versus wavelength in the O-band.
Figure 7:
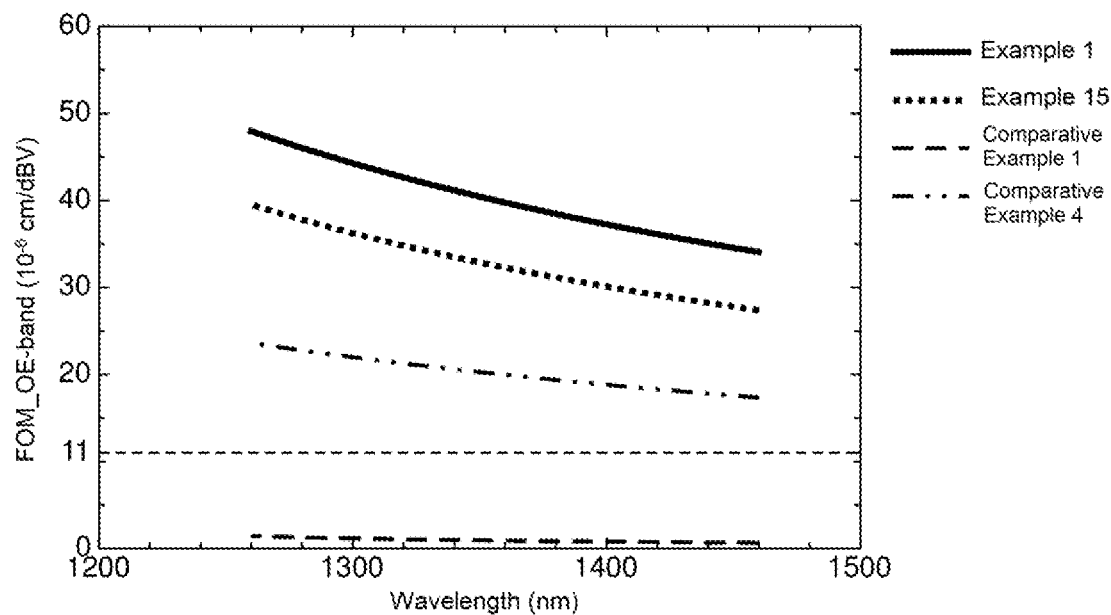
FIG. 7 shows a plot of the calculated FOM versus wavelength in the OE-band.
Figure 8:
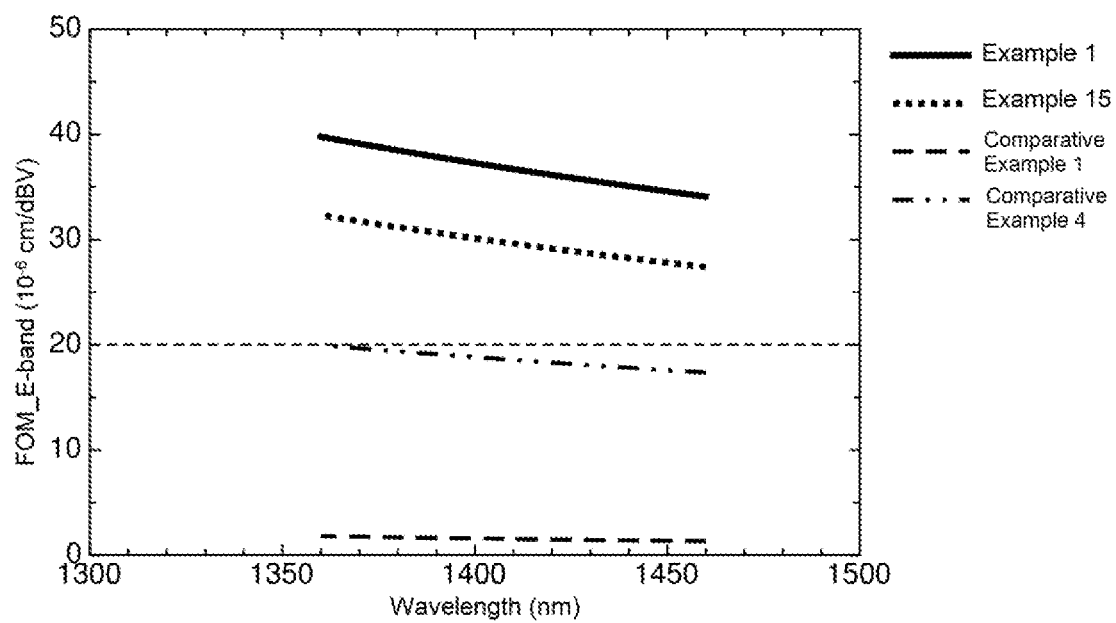
FIG. 8 shows a plot of the calculated FOM versus wavelength in the E-band.
Figure 9:
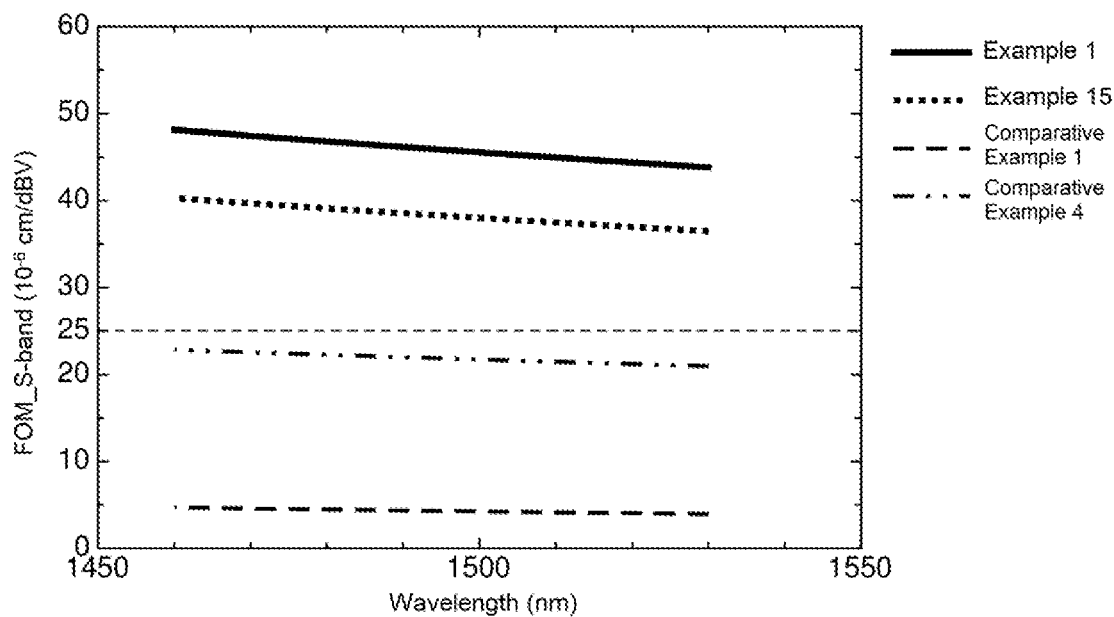
FIG. 9 shows a plot of the calculated FOM versus wavelength in the S-band.
Figure 10:
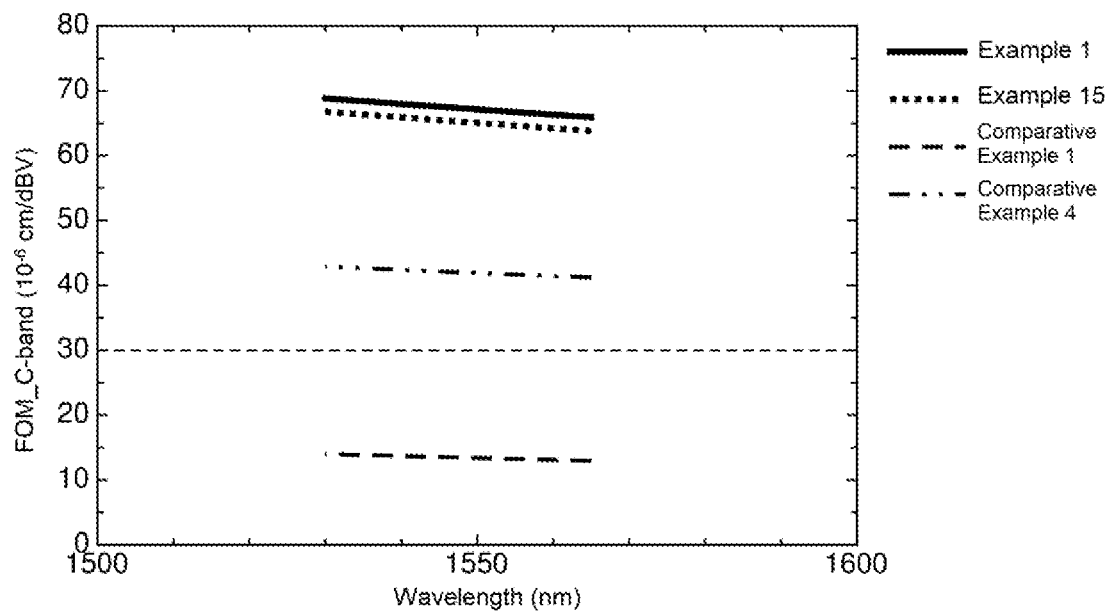
FIG. 10 shows a plot of the calculated FOM versus wavelength in the C-band.
Figure 11:
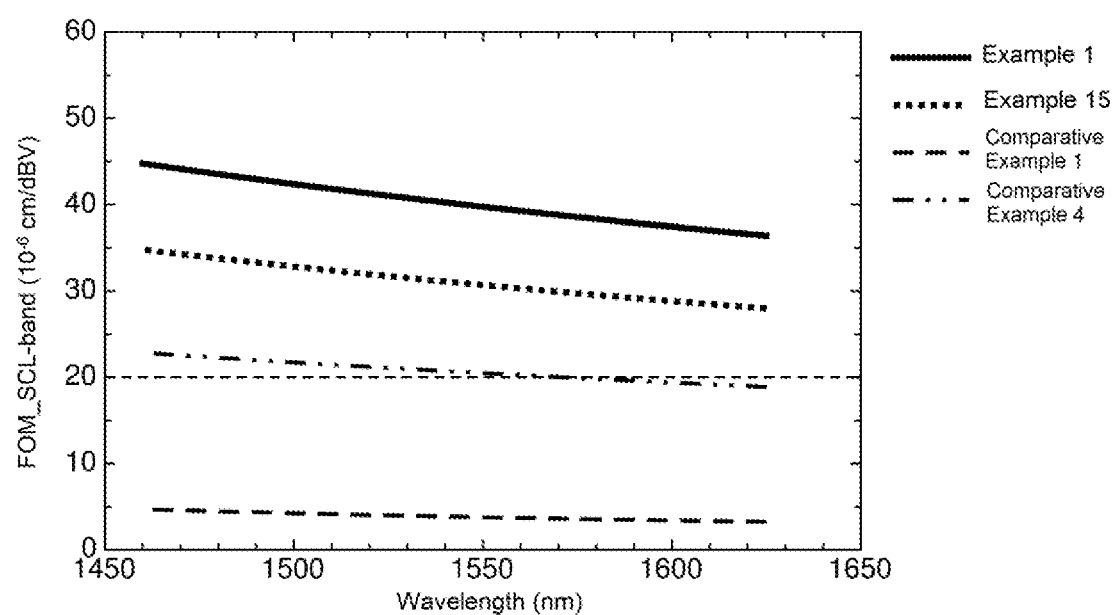
FIG. 11 shows a plot of the calculated FOM versus wavelength in the SCL-band.

The absorption coefficients, refractive indices, and EO coefficients of the electro-optic polymers of Examples 1 and 15 and Comparative Examples 1 and 4 were determined according to the methods described below, and their EO coefficients and FOM were calculated (for the entire optical communication wavelength range and for each band) according to the methods described below. The results are shown in FIGS. 1 to 11. The EO coefficients for the entire optical communication wavelength range and for the O-band are shown as representatives. Before the measurement of the properties of each electro-optic polymer, a film was prepared from each electro-optic polymer according to the method described below and used for such measurement.

Film-Forming Method for Electro-Optic Polymers (EO Polymers)

The polymer obtained in each Example or Comparative Example was dissolved in cyclohexanone to prepare a 1 to 20 wt % solution. The solution was applied on a cleaned substrate (silicon, glass, quarts glass) using a spin coater 1H-DX2 manufactured by MIKASA, CO., LTD. at 500 to 6000 rpm. The coated substrate was vacuum dried around at the glass transition temperature (Tg) for 1 hour. The concentration of the polymer solution and the rotational speed of the spin coater were determined as appropriate for each polymer to provide the desired film thickness.

Absorption Spectra of EO Polymer Thin-Films

The absorption spectrum of an about 0.15-μm-thick thin-film of each EO polymer on the quarts-glass substrate was measured using the spectrophotometer U-4000 manufactured by Hitachi High-Tech Corporation. The measured values were substituted into the Lorentz dispersion formula given below. The intensity coefficient ($A_a$), resonance wavelength ($\lambda_0$), and attenuation coefficient ($\gamma$) were determined by the least-squares method.

$$a(\lambda) = \frac{1}{n(\lambda)} \frac{A_a \gamma / \lambda^2}{(1/\lambda_0^2 - 1/\lambda^2)^2 + \gamma^2/\lambda^2} \quad \text{[Math. 3]}$$

Refractive Indices of EO Polymers

The refractive index (n) of each EO polymer was measured on an about 3-μm-thick film of the EO polymer on the quarts glass substrate, using the prism coupler 2010/M manufactured by Metricon Corporation. The measured values at wavelengths of 1308 nm and 1532 nm were substituted into the Lorentz dispersion formula given below. The intensity coefficient ($A_n$) and background refractive index ($n_b$) were determined by the least-squares method. As the refractive index at a particular wavelength, a calculated value based on the following Lorentz dispersion formula was used.

$$n(\lambda) = \left[ n_b^2 + \frac{A_a(1/\lambda_0^2 - 1/\lambda^2)}{(1/\lambda_0^2 - 1/\lambda^2)^2 + \gamma^2/\lambda^2} \right]^{1/2} \quad \text{[Math. 4]}$$

Absorption Coefficients of EO Polymer Thick-Films

Dents of three different depths ranging from 40 to 350 μm were formed in a quarts-glass substrate. The dents were filled with an EO polymer, and the surfaces were polished. Thus, EO polymer thick-films of three different thicknesses were produced. The absorption spectra of the differently thick EO polymer films were measured using the spectrophotometer U-4000 manufactured by Hitachi High-Tech Corporation. The absorbance vs film thickness graph at each wavelength was fitted with linear regression to estimate the slope, and based on the slope, the absorption coefficient was calculated.

EO Coefficient Measurement Method for EO Polymers

EO coefficients were measured as described in the reference ("Transmission ellipsometric method without an aperture for simple and reliable evaluation of electro-optic properties", Toshiki Yamada and Akira Otomo, Optics Express, vol. 21, pages 29240-48 (2013)). The laser used as alight source was DFB laser 81663A manufactured by Agilent Technologies (wavelengths: 1308 nm and 1550 nm).

The measured values at wavelengths of 1308 nm and 1550 nm were substituted into the two-state model dispersion formula given below. The intensity coefficient ($A_r$) was determined by the least-squares method. As the EO coefficient at a particular wavelength, a calculated value based on the following two-state model dispersion formula was used.

$$r(\lambda) = \frac{A_r}{n^4(\lambda)} \frac{3/\lambda_0^2 - 1/\lambda^2}{(1/\lambda_0^2 - 1/\lambda^2)^2} \quad \text{[Math. 5]}$$

FOM Calculation Method for EO Polymers

The FOMs are calculated by the following formula:

$$FOM = \frac{n^3 r}{a_{max}\lambda}[10^{-6} \text{ cm/dBV}] \quad \text{[Math. 6]}$$

wherein n indicates a refractive index, r indicates an EO coefficient, $a_{max}$ indicates a maximum absorption coefficient in a wavelength range of interest, and λ indicates a wavelength.

Test Example 2

The absorption coefficients, refractive indices, and EO coefficients of the EO polymers of Examples 5 to 11, 13, and 14 and Comparative Examples 1 to 4 were determined according to the methods described in Test Example 1, and their EO coefficients and FOM were calculated (for the entire optical communication wavelength range, for the O-band, and for the OE-band) according to the methods described in Test Example 1. The results are shown in Table 17. The results of Examples 1 and 15 obtained in Test Example 1 are also shown for reference.

TABLE 17

| | Entire optical communication wavelength range | | O band | | OE band | |
|---|---|---|---|---|---|---|
| | Minimum EO coefficient (pm/V) | Minimum FOM (×10⁻⁶ cm/dBV) | Minimum EO coefficient (pm/V) | Minimum FOM (×10⁻⁶ cm/dBV) | Minimum EO coefficient (pm/V) | Minimum FOM (×10⁻⁶ cm/dBV) |
| Example 1 | 55.7 | 27.7 | 65.3 | 48.0 | 60.8 | 34.1 |
| Example 5 | 47.1 | 30.0 | 55.6 | 63.5 | 51.5 | 37.0 |
| Example 6 | 40.1 | 18.6 | 47.7 | 33.0 | 44.1 | 23.0 |
| Example 7 | 47.2 | 21.2 | 56.1 | 37.0 | 51.9 | 26.2 |
| Example 8 | 45.9 | 29.0 | 54.0 | 51.8 | 50.2 | 35.7 |
| Example 9 | 50.7 | 35.8 | 59.2 | 63.0 | 55.1 | 43.9 |
| Example 10 | 52.8 | 28.1 | 62.7 | 53.9 | 58.0 | 34.8 |
| Example 11 | 46.0 | 26.4 | 54.5 | 47.7 | 50.4 | 32.6 |
| Example 13 | 49.0 | 25.9 | 58.1 | 47.8 | 53.8 | 32.0 |
| Example 14 | 48.4 | 25.8 | 56.4 | 52.3 | 52.6 | 31.6 |
| Example 15 | 39.1 | 22.0 | 47.1 | 41.3 | 43.3 | 27.4 |
| Comparative Example 1 | 142 | 0.46 | 218 | 0.92 | 177 | 0.67 |
| Comparative Example 2 | 70.2 | 2.83 | 85.6 | 4.29 | 78.1 | 3.58 |
| Comparative Example 3 | 68.4 | 7.93 | 83.6 | 11.9 | 76.2 | 9.96 |
| Comparative Example 4 | 25.0 | 14.4 | 28.7 | 24.4 | 26.9 | 17.4 |

Test Example 3

The absorption coefficients, refractive indices, and EO coefficients of the EO polymers of Examples 5 to 11, 13, and 14 were determined according to the methods described in Test Example 1, and their EO coefficients and FOM were calculated (for the E-band, for the S-band, for the C-band, and for the SCL-band) according to the methods described in Test Example 1. The results are shown in Table 18. The results of Examples 1 and 15 obtained in Test Example 1 are also shown for reference.

TABLE 18

| | C band | | S band | | E band | | SCL band | |
|---|---|---|---|---|---|---|---|---|
| | Minimum EO coefficient (pm/V) | Minimum FOM (×10$^{-6}$ cm/dBV) | Minimum EO coefficient (pm/V) | Minimum FOM (×10$^{-6}$ cm/dBV) | Minimum EO coefficient (pm/V) | Minimum FOM (×10$^{-6}$ cm/dBV) | Minimum EO coefficient (pm/V) | Minimum FOM (×10$^{-6}$ cm/dBV) |
| Example 1 | 57.3 | 65.9 | 58.3 | 43.8 | 60.8 | 34.1 | 55.7 | 36.4 |
| Example 5 | 48.5 | 89.4 | 49.4 | 50.7 | 51.5 | 37.0 | 47.1 | 43.1 |
| Example 6 | 41.4 | 38.7 | 42.2 | 27.8 | 44.1 | 23.0 | 40.1 | 24.8 |
| Example 7 | 48.7 | 53.1 | 49.6 | 36.1 | 51.9 | 26.2 | 47.2 | 29.7 |
| Example 8 | 47.2 | 82.6 | 48.1 | 45.8 | 50.2 | 35.7 | 45.9 | 39.7 |
| Example 9 | 52.0 | 102.3 | 53.0 | 52.1 | 55.1 | 43.9 | 50.7 | 44.1 |
| Example 10 | 54.4 | 83.0 | 55.5 | 46.8 | 58.0 | 34.8 | 52.8 | 38.5 |
| Example 11 | 47.4 | 66.2 | 48.3 | 41.3 | 50.4 | 32.6 | 46.0 | 36.2 |
| Example 13 | 50.5 | 66.6 | 51.5 | 39.6 | 53.8 | 32.0 | 49.0 | 34.5 |
| Example 14 | 49.7 | 73.5 | 50.5 | 43.9 | 52.6 | 31.6 | 48.4 | 36.6 |
| Example 15 | 40.4 | 63.8 | 41.3 | 36.5 | 43.3 | 27.4 | 39.1 | 28.0 |

Test Example 4

The absorption coefficients, refractive indices, and EO coefficients of the EO polymers of Examples 20 to 24 were determined according to the methods described in Test Example 1, and their EO coefficients and FOM were calculated (for the entire optical communication wavelength range, for the O-band, for the OE-band, for the E-band, for the S-band, for the C-band, and for the SCL-band) according to the methods described in Test Example 1. The results are shown in Tables 19 and 20.

TABLE 19

| | Entire optical communication wavelength range | | O band | | OE band | |
|---|---|---|---|---|---|---|
| | Minimum EO coefficient (pm/V) | Minimum FOM (×10$^{-6}$ cm/dBV) | Minimum EO coefficient (pm/V) | Minimum FOM (×10$^{-6}$ cm/dBV) | Minimum EO coefficient (pm/V) | Minimum FOM (×10$^{-6}$ cm/dBV) |
| Example 20 | 49.6 | 23.8 | 58.5 | 44.3 | 54.3 | 29.3 |
| Example 21 | 53.6 | 28.0 | 62.8 | 53.9 | 58.4 | 34.4 |
| Example 22 | 45.4 | 24.0 | 53.6 | 42.9 | 49.7 | 29.5 |
| Example 23 | 44.3 | 25.9 | 52.6 | 50.5 | 48.6 | 31.9 |
| Example 24 | 53.1 | 25.7 | 63.0 | 47.9 | 58.3 | 31.8 |

TABLE 20

| | C band | | S band | | E band | | SCL band | |
|---|---|---|---|---|---|---|---|---|
| | Minimum EO coefficient (pm/V) | Minimum FOM (×10$^{-6}$ cm/dBV) | Minimum EO coefficient (pm/V) | Minimum FOM (×10$^{-6}$ cm/dBV) | Minimum EO coefficient (pm/V) | Minimum FOM (×10$^{-6}$ cm/dBV) | Minimum EO coefficient (pm/V) | Minimum FOM (×10$^{-6}$ cm/dBV) |
| Example 20 | 51.1 | 65.2 | 52.0 | 40.4 | 54.3 | 29.3 | 49.6 | 35.5 |
| Example 21 | 55.1 | 83.9 | 56.1 | 46.5 | 58.4 | 34.4 | 53.6 | 41.4 |
| Example 22 | 46.8 | 62.4 | 47.6 | 36.8 | 49.7 | 29.5 | 45.4 | 32.8 |

TABLE 20-continued

| | C band | | S band | | E band | | SCL band | |
|---|---|---|---|---|---|---|---|---|
| | Minimum EO coefficient (pm/V) | Minimum FOM (×10⁻⁶ cm/d BV) | Minimum EO coefficient (pm/V) | Minimum FOM (×10⁻⁶ cm/d BV) | Minimum EO coefficient (pm/V) | Minimum FOM (×10⁻⁶ cm/d BV) | Minimum EO coefficient (pm/V) | Minimum FOM (×10⁻⁶ cm/d BV) |
| Example 23 | 45.6 | 96.0 | 46.5 | 43.9 | 48.6 | 31.9 | 44.3 | 39.2 |
| Example 24 | 54.7 | 75.5 | 55.8 | 42.2 | 58.3 | 31.8 | 53.1 | 37.5 |

The results show that the EO polymers of Comparative Examples have a high EO coefficient and a low FOM or have a high FOM and a low EO coefficient, while the EO polymers of the present invention have a high EO coefficient and a high FOM.

INDUSTRIAL APPLICABILITY

The EO polymer of the present invention has good performance over the entire optical communication wavelength range and therefore can preferably be used for the production of optical modulators, optical switches, optical transceivers, optical phased arrays, LiDAR (light detection and ranging) devices, electric field sensors, terahertz wave generators and detectors, etc.

The invention claimed is:
1. An electro-optic polymer (EO polymer) comprising an electro-optic molecule (EO molecule) and a base polymer, the EO molecule having a structure in which a π-electron donor and a π-electron acceptor are conjugated via a π-conjugation bridge,
the EO polymer having an electro-optic coefficient (EO coefficient) of 30 pm/V or more and a figure of merit (FOM) of $10 \times 10^{-6}$ cm/dBV or more in an entire optical communication wavelength range of 1260 nm to 1625 nm,
the FOM being defined by the following formula:

$$FOM = \frac{n^3 r}{a_{max} \lambda} [10^{-6} \text{ cm}/dBV] \quad [\text{Math. 1}]$$

wherein n indicates a refractive index, r indicates an EO coefficient, $a_{max}$ indicates a maximum absorption coefficient in a wavelength range of interest, and λ indicates a wavelength,
wherein the EO molecule is a compound represented by the following formula (1):

[Chem. 1]

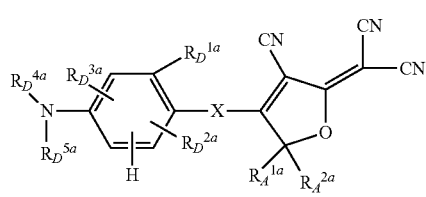
(1)

wherein
$R_D^{1a}$, $R_D^{2a}$, and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, —R¹—OH wherein R¹ is a hydrocarbon group, —OR²—OH wherein R² is a hydrocarbon group, —OC(=O)R³ wherein R³ is a hydrocarbon group, an amino group, —R⁴—NH₂ wherein R⁴ is a hydrocarbon group, a thiol group, —R⁵—SH wherein R⁵ is a hydrocarbon group, —NCO, or —R⁶—NCO wherein R⁶ is a hydrocarbon group, and $R_D^{1a}$, $R_D^{2a}$, and $R_D^{3a}$ each may have one or more identical or different substituents;
$R_D^{4a}$ and $R_D^{5a}$ independently represent a hydrogen atom, an alkyl group, a haloalkyl group, an acyloxyalkyl group, a silyloxyalkyl group, —R¹—OH wherein R¹ is a hydrocarbon group, —R⁴—NH₂ wherein R⁴ is a hydrocarbon group, an aryl group, —R⁵—SH wherein R⁵ is a hydrocarbon group, or —R⁶—NCO wherein R⁶ is a hydrocarbon group, and $R_D^{4a}$ and $R_D^{5a}$ each may have one or more identical or different substituents;
X represents a linking group;
$R_A^{1a}$ and $R_A^{2a}$ independently represent a hydrogen atom, an alkyl group, an alkenyl group, a cycloalkyl group, a cycloalkenyl group, an alkoxy group, an aryl group, a hydroxy group, —R¹—OH wherein R¹ is a hydrocarbon group, —OR²—OH wherein R² is a hydrocarbon group, an amino group, —R⁴—NH₂ wherein R⁴ is a hydrocarbon group, a thiol group, —R⁵—SH wherein R⁵ is a hydrocarbon group, —NCO, or —R⁶—NCO wherein R⁶ is a hydrocarbon group, and $R_A^{1a}$ and $R_A^{2a}$ each may have one or more identical or different substituents, and
at least one of $R_A^{1a}$ and $R_A^{2a}$ is a substituent selected from the group consisting of an aryl group having a halogen atom, an aryl group having a haloalkyl group, and an aryl group having an aryl group optionally having a halogen atom; and
wherein X in formula (1) is represented by the following formula (B-I)

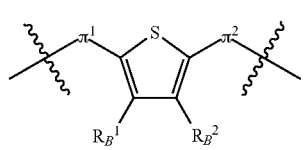
(B-I)

wherein
$R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, —$R^1$—OH wherein $R^1$ is a hydrocarbon group, —$OR^2$—OH wherein $R^2$ is a hydrocarbon group, an amino group, —$R^4$—$NH_2$ wherein $R^4$ is a hydrocarbon group, a thiol group, —$R^5$—SH wherein $R^5$ is a hydrocarbon group, —NCO, or —$R^6$—NCO wherein $R^6$ is a hydrocarbon group, $R_B^1$ and $R_B^2$ each may have one or more identical or different substituents, and $R_B^1$ and $R_B^2$ may form a ring together with the two carbon atoms to which they are bound, $\pi^1$ and $\pi^2$ are each a structure represented by the following formula (B-IV):

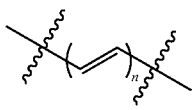

(B-IV)

wherein n represents an integer of 1.

2. The EO polymer according to claim 1, wherein the EO polymer has an EO coefficient of 35 pm/V or more and an FOM of $13 \times 10^{-6}$ cm/dBV or more in O-band ranging in wavelength from 1260 nm to 1360 nm.

3. The EO polymer according to claim 1, wherein the EO polymer has an EO coefficient of 32 pm/V or more and an FOM of $11 \times 10^{-6}$ cm/dBV or more in OE-band ranging in wavelength from 1260 nm to 1460 nm.

4. The EO polymer according to claim 1, wherein the EO polymer has an EO coefficient of 32 pm/V or more and an FOM of $20 \times 10^{-6}$ cm/dBV or more in E-band ranging in wavelength from 1360 nm to 1460 nm.

5. The EO polymer according to claim 1, wherein the EO polymer has an EO coefficient of 32 pm/V or more and an FOM of $25 \times 10^{-6}$ cm/dBV or more in S-band ranging in wavelength from 1460 nm to 1530 nm.

6. The EO polymer according to claim 1, wherein the EO polymer has an EO coefficient of 31 pm/V or more and an FOM of $30 \times 10^{-6}$ cm/dBV or more in C-band ranging in wavelength from 1530 nm to 1565 nm.

7. The EO polymer according to claim 1, wherein the EO polymer has an EO coefficient of 30 pm/V or more and an FOM of $20 \times 10^{-6}$ cm/dBV or more in SCL-band ranging in wavelength from 1460 nm to 1625 nm.

8. The EO polymer according to claim 1, wherein the number of the halogen atom is 1 to 5.

9. The EO polymer according to claim 1, wherein the halogen atom is one or more selected from the group consisting of fluorine, chlorine, and bromine.

10. The EO polymer according to claim 1, wherein the EO molecule is bound to the base polymer via the $R_D^{4a}$ and/or the $R_D^{5a}$ in formula (1).

11. A production method of an optical control device using the EO polymer according to claim 1.

12. The production method according to claim 11, wherein the optical control device is an optical modulator, an optical switch, an optical transceiver, an optical phased array, a LiDAR (light detection and ranging) device, an electric field sensor, or a terahertz wave generator and detector.

13. The EO polymer according to claim 1, wherein a combination of the $R_A^{1a}$ and the $R_A^{2a}$ is such that the $R_A^{1a}$ is an alkyl group and the $R_A^{2a}$ is an aryl group having a halogen atom, an aryl group having a haloalkyl group, or an aryl group having an aryl group optionally having a halogen atom.

14. An optical element formed from the EO polymer according to claim 1.

15. An optical control device comprising the optical element according to claim 14.

* * * * *